(12) United States Patent
Despa

(10) Patent No.: US 12,115,141 B2
(45) Date of Patent: Oct. 15, 2024

(54) DIAGNOSIS OF DIABETES BY DETECTING AGGREGATED AMYLIN IN ERYTHROCYTES

(71) Applicant: University of Kentucky Research Foundation, Lexington, KY (US)

(72) Inventor: Florin Despa, Lexington, KY (US)

(73) Assignee: University of Kentucky Research Foundation, Lexington, KY (US)

(*) Notice: Subject to any disclaimer, the term of this patent is extended or adjusted under 35 U.S.C. 154(b) by 575 days.

(21) Appl. No.: 16/684,439

(22) Filed: Nov. 14, 2019

(65) Prior Publication Data

US 2020/0147026 A1 May 14, 2020

Related U.S. Application Data

(60) Provisional application No. 62/883,992, filed on Aug. 7, 2019, provisional application No. 62/767,131, filed on Nov. 14, 2018.

(51) Int. Cl.
*A61K 31/202* (2006.01)
*G01N 33/74* (2006.01)

(52) U.S. Cl.
CPC .......... *A61K 31/202* (2013.01); *G01N 33/74* (2013.01); *G01N 2333/575* (2013.01); *G01N 2800/042* (2013.01)

(58) Field of Classification Search
CPC ............... A61K 31/202; G01N 33/74; G01N 2333/575; G01N 2800/042
See application file for complete search history.

(56) References Cited

U.S. PATENT DOCUMENTS

| | | |
|---|---|---|
| 6,399,314 B1 | 6/2002 | Krishnamurthy |
| 2002/0009440 A1 | 1/2002 | Terry et al. |
| 2005/0089852 A1 | 4/2005 | Lee et al. |
| 2008/0038761 A1 | 2/2008 | Beernink et al. |
| 2011/0046212 A1 | 2/2011 | Berti et al. |
| 2011/0124022 A1 | 5/2011 | Nagalla et al. |
| 2011/0200609 A1 | 8/2011 | Glabe et al. |
| 2013/0109581 A1 | 5/2013 | Salisbury et al. |
| 2013/0143804 A1 | 6/2013 | Despa et al. |
| 2013/0266930 A1 | 10/2013 | Dinges |
| 2015/0110777 A1 | 4/2015 | Barbour et al. |
| 2015/0191541 A1 | 7/2015 | Barbour et al. |
| 2015/0210759 A1 | 7/2015 | Grimm et al. |
| 2017/0205420 A1 | 7/2017 | Suonpaa et al. |

FOREIGN PATENT DOCUMENTS

| | | |
|---|---|---|
| WO | WO2006/088281 | 8/2006 |
| WO | WO2010/012004 A2 | 1/2010 |
| WO | WO2013/026060 | 2/2013 |

OTHER PUBLICATIONS

Giordano Oxygen, oxidative stress, hypoxia, and heart failure J Clin Invest. Mar. 1, 2005; 115(3): 500-508 (Year: 2005).*
Liu, et al., Concentration of Aggregated Amylin in Red Blood Cells Mediates Amylin Deposition in Cardiac Myocytes in Patients with Heart Failure and Type-2 Diabetes, 2016 AHA Late-Breaking Basic Science Abstracts, pp. e168.
Banks, et al., Permeability of the Blood Brain Barrier to Amylin, Life Sciences, 1995, vol. 57, No. 22, pp. 1993-2001.
Percy, et al., Development of sensitive immunoassays to detect amylin and amylin-like peptides in unextracted plasma, Clinical Chemistry, 1996, 42:4; ppl 576-585.
Zheng, et al., Serum levels of proamylin and amylin in normal subjects and patients with impaired glucose regulation and type 2 diabetes, Acta Diabetol (2010) 47:265-270.
Yoshimura, et al., Development of 99mTC-Labeled Pyridyl Benzofuran Derivatives to Detect Pancreatic Amylin in Islet Amyloid Model Mice, Bioconjugate Chem. 2016, 27, 1532-1539.
Martinez-Alvarez, et al., Molecular characterization of calcitonin gene-related peptide (CGRP) related peptides (CGRP, amylin, adrenomedullin and adrenomedullin-2/intermedin) in golfish (*Carassius auratus*) Cloning and distribution, Peptides 29 (2008) 15534-1543.
The Human Protein Atlas IAPP (https://www.proteinatlas.org/ENSG00000121351-IAPP/tissue#gene_information).
Martinez-Valbuena, et al., Amylin as a Potential Link between Type 2 Diabetes and Alzheimer Disease, ANNALS of Neurology, 2019, pp. 1-13.
Anguiano M, Nowak RJ, Lansbury PT, Jr. Protofibrillar islet amyloid polypeptide permeabilizes synthetic vesicles by a pore-like mechanism that may be relevant to type II diabetes. Biochemistry 41:11338-11343 (2002).
Barrett EJ, Liu Z, Khamaisi M, et al. Diabetic Microvascular Disease: An Endocrine Society Scientific Statement. J Clin Endocrinol Metab. 2017;102:4343-4410.
Biessels GJ, Despa F. Cognitive decline and dementia in diabetes mellitus: mechanisms and clinical implications. Nat. Rev. Endocrinol. 2018;14:591-604.
Butler AE, Jang J, Gurlo T, et al. Diabetes due to a progressive defect in beta-cell mass in rats transgenic for human islet amyloid polypeptide (HIP Rat): a new model for type 2 diabetes. Diabetes. 2004;53:1509-1516.
Collins JM, F Despa and RC. Lee Structural and Functional Recovery of Electropermeabilized Skeletal Muscle in-vivo after Treatment with Surfactant Poloxamer 188 Biochim. Biophys. Acta, 1768 1238-1246 (2007).
Degano P, Silvestre RA, Salas M, Peiro E, Marco J: Amylin inhibits glucose-induced insulin secretion in a dose-dependent manner: study in the perfused rat pancreas. Regul Pept 43:91-96, 1993.
Despa S, Margulies KB, Chen L, et al. Hyperamylinemia contributes to cardiac dysfunction in obesity and diabetes: A study in humans and rats. Circ. Res. 2012;110:598-608.

(Continued)

*Primary Examiner* — Jeffrey S Lundgren
*Assistant Examiner* — William Y Lee
(74) *Attorney, Agent, or Firm* — Stites & Harbison PLLC; Gary N. Stewart; Mandy Wilson Decker

(57) ABSTRACT

The presently-disclosed subject matter generally relates to methods for detecting the presence of amylin in a patient's erythrocytes, determining the risk for the development of prediabetes, type-2 diabetes or comorbidities thereof, and methods of treating said diseases and risks.

11 Claims, 51 Drawing Sheets

Specification includes a Sequence Listing.

(56) References Cited

OTHER PUBLICATIONS

Despa S, Sharma S, Harris TR, et al. Cardioprotection by controlling hyperamylinemia in a "humanized" diabetic rat model. J. Am. Heart. Assoc. 2014;3:pii: e001015.

Fawver JN, Ghiwot Y, Koola C, et al. Islet amyloid polypeptide (IAPP): A second amyloid in Alzheimer's disease. Curr. Alzheimer. Res. 2014;1:928-940.

Gurlo T, S Ryazantsev, CJ Huang, MW Yeh, HA Reber, OJ Hines, TD O'Brien, CG Glabe, PC Butler, Evidence for proteotoxicity in beta cells in type 2 diabetes: toxic islet amyloid polypeptide oligomers form intracellularly in the secretory pathway. Am J Pathol 176, 861-869 (2010).

Huang CJ, Haataja L, Gurlo T, et al. Induction of endoplasmic reticulum stress-induced beta-cell apoptosis and accumulation of polyubiquitinated proteins by human islet amyloid polypeptide. Am. J. Physiol. Endocrinol. Metab. 2007;293:E1656-E1662.

Imig JD. Epoxides and soluble epoxide hydrolase in cardiovascular physiology. Physiol Rev. 2012;92:101-130.

Imig JD. Epoxyeicosatrienoic Acids and 20-Hydroxyeicosatetraenoic Acid on Endothelial and Vascular Function. Adv Pharmacol. 2016 ; 77: 105-141.

Jackson K, Barisone GA, Diaz E, et al. Amylin deposition in the brain: A second amyloid in Alzheimer disease? Ann. Neurol. 2013;74:517-526.

Janciauskiene S., B. Ahren, Fibrilar islet amyloid polypeptide differentially affects oxidative mechanisms and lipoprotein uptake in correlation with cytotoxicity in two insulin-producing cell lines. Biochem Biophys Res Commun. 267:2 (2000) 619-625.

Janson J, Ashley RH, Harrison D, Mcintyre S, Butler PC. The mechanism of islet amyloid polypeptide toxicity is membrane disruption by intermediate-sized toxic amyloid particles. Diabetes 48:491-498 (1999).

Johnson KH, TD O'Brien, K Jordan P Westermark, Impaired glucose tolerance is associated with increased islet amyloid polypeptide (IAPP) immunoreactivity in pancreatic beta cells. Am. J. Pathol. 135, 245-250 (1989).

Jurgens CA, Toukatly MN, Fligner CL, Udayasankar J, Subramanian SL, Zraika S, Aston-Mourney K, Carr DB, Westermark P, Westermark GT, Kahn SE, Hull RL: β-cell loss and B-cell apoptosis in human type 2 diabetes are related to islet amyloid deposition. Am J Pathol 2011, 178(6):2632-2640.

Lee RC, Despa F, Tang X, Titushkin I, Cho M. Direct observations of the P188 mediated membrane sealing with atomic force microscopy. Molecular & Cellular Biomechanics, 3 185-186 (2006).

Leighton B, Cooper GJS: Pancreatic amylin and calcitonin gene-related peptide causes resistance to insulin in skeletal muscle in vitro. Nature 1988, 355(6191):632-635.

Liu M, Hoskins A, Verma N, et al. Amylin and diabetic cardiomyopathy—amylininduced sarcolemmal Ca2+ leak is independent of diabetic remodeling of myocardium. Biochim. Biophys. Acta. Mol. Basis Dis. 2018;1864:1923-1930.

Liu M, Verma N, Peng X, et al. Hyperamylinemia increases IL-1β synthesis in the heart via peroxidative sarcolemmal injury. Diabetes. 2016;65:2772-2783.

Ly H, Verma N, Wu F, et al. Brain microvascular injury and white matter disease provoked by diabetes-associated hyperamylinemia. Ann. Neurol. 2017;82:208-222.

Masters S.L., A. Dunne, S.L. Subramanian, R.L. Hull, G.M. Tannahill, F.A. Sharp, C. Becker, L. Franchi, E. Yoshihara, Z. Chen, N. Mullooly, L.A. Mielke, J. Harris, R.C. Coll, K. H. Mills, K.H. Mok, P. Newsholme, G. Nunez, J. Yodoi, S.E. Kahn, E.C. Lavelle, L.A. O'Neill, Activation of the NLRP3 inflammasome by islet amyloid polypeptide provides a mechanism for enhanced IL-1beta in type 2 diabetes. Nat Immunol. 11 (2010) 897-904.

Matveyenko A.V., P.C. Butler, Islet amyloid polypeptide (IAPP) transgenic rodents as models for Type 2 Diabetes. LAR Journal. 47 (2006) 225-233.

Matveyenko A.V., P.C. Butler, ?-cell deficit due to increased apoptosis in the human islet amyloid polypeptide transgenic (HIP) rat recapitulates the metabolic defects present in type-2 diabetes. Diabetes. 55 (2006) 2106-2114.

Molina JM, Cooper GJS, Leighton B, Olefsky JM: Induction of insulin resistance in vivo by amylin and calcitonin gene-related peptide. Diabetes 1990, 39(2):260-265.

Moreno-Gonzalez I, Edwards 3rd G, Salvadores N, et al. Molecular interaction between type 2 diabetes and Alzheimer's disease through cross-seeding of protein misfolding. Mol Psychiatry 2017;22(9):13271334.

Node K, Huo Y, Ruan X, et al. Anti-inflammatory properties of cytochrome P450 epoxygenase-derived eicosanoids. Science. 1999;285:1276-1279.

Oskarsson ME, Paulsson JF, Schultz SW, et al. In vivo seeding and cross-seeding of localized amyloidosis: A molecular link between type 2 diabetes and Alzheimer disease. Am. J. Pathol. 2015;185:834-846.

Paulsson JF, Ludvigsson J, Carlsson A, Casas R, Forsander G, Ivarsson SA, Kockum I, Lernmark Å, Marcus C, Lindblad B, Westermark GT. High plasma levels of islet amyloid polypeptide in young with new-onset of type 1 diabetes mellitus. PLOS One. 2014;9(3):e93053.

Schultz N, Byman E, Fex M, et al. Amylin alters human brain pericyte viability and NG2 expression. J. Cereb. Blood Flow Metab. 2016;37:1470-1482.

Schultz N, Byman E, Netherlands BB, et al. Levels of retinal IAPP are altered in Alzheimer's disease patients and correlate with vascular changes and hippocampal IAPP levels. Neurobiol. Aging. 2018;69:94-101.

Srodulski S., A. Loria, S. Despa, F. Despa, Hyperamylinemia, a potential therapeutic target in diabetic cardiorenal syndrome. Circulation. 130 (2013) A13963.

Srodulski S., S. Savita, A.B. Bachstetter, J.M. Brelsfoard, C. Pascual, X.S. Xie, K.E. Saatman, L.J. Van Eldik, F. Despa, Neuroinflammation and neurologic deficits in diabetes linked to brain accumulation of amylin. Mol Neurodegener. 9 (2014) 30.

Verma N, Ly H, Liu M, et al. Intraneuronal amylin deposition, peroxidative membrane injury and increased IL-1β synthesis in brains of Alzheimer's disease patients with type-2 diabetes and in diabetic HIP rats. J. Alzheimers. Dis. 2016;53:259-272.

Westermark P, Andersson A, Westermark GT. Islet amyloid polypeptide, islet amyloid, and diabetes mellitus. Physiol. Rev. 2011;91:795-826.

Westermark P, Engstrom U, Johnson KH, et al. Islet amyloid polypeptide: pinpointing amino acid residues linked to amyloid fibril formation. Proc. Natl. Acad. Sci. USA. 1990;87:5036-5040.

Westwell-Roper C., D.L. Dai, G. Soukhatcheva, K.J. Potter, N. van Rooijen, J.A. Ehses, C.B. Verchere, IL-1 blockade attenuates islet amyloid polypeptide-induced proinflammatory cytokine release and pancreatic islet graft dysfunction. J Immunol. 187 (2011) 2755-2765.

Zierath JR, Galuska D, Engstrom A, Johnson KH, Betsholtz C, Westermark P, Wallberg-Henriksson H: Human islet amyloid polypeptide at pharmacological levels inhibits insulin and phorbol ester-stimulated glucose transport in in vitro incubated human muscle strips. Diabetologia 35:26-31, 1992.

Zraika S1, Hull RL, Udayasankar J, et al. Oxidative stress is induced by islet amyloid formation and time-dependently mediates amyloid-induced beta cell apoptosis. Diabetologia. 2009;52:626-635.

Erickson JR, Pereira L, Wang L, Han G, Ferguson A, Dao K, Copeland RJ, Despa F, Hart GW, Ripplinger CM, and Bers DM, Diabetic Hyperglycemia activates CaMKII and Arrhythmias by O linked Glycosylation. Nature. 2013; 502:372-6.

Liu, et al., Microhemorrhages in Myocardium and Kidneys Provoked by Amylin-Loaded Erythrocytes. Circulation (2017) 136: A14887.

\* cited by examiner

FIG. 20A 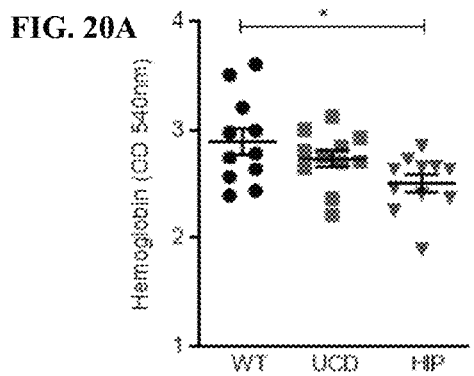 FIG. 20B 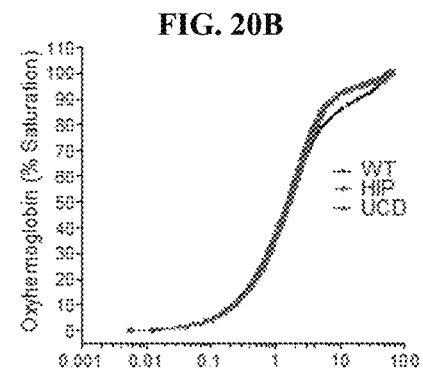
FIG. 20C 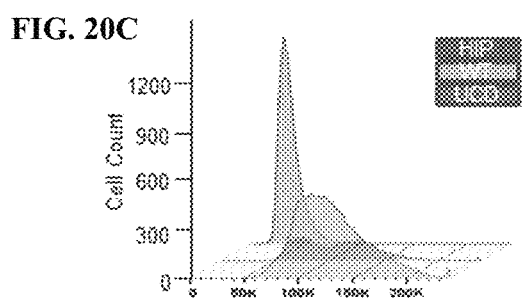 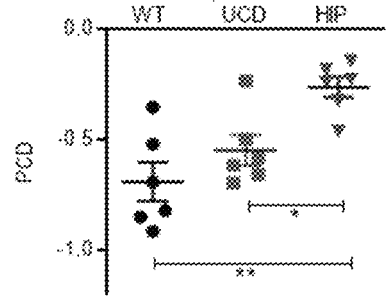

FIG. 22A
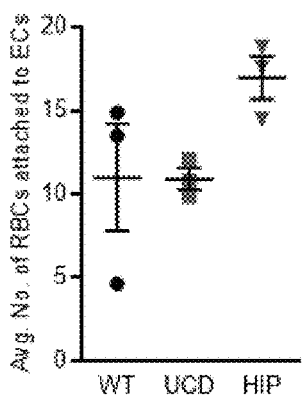
FIG. 22B
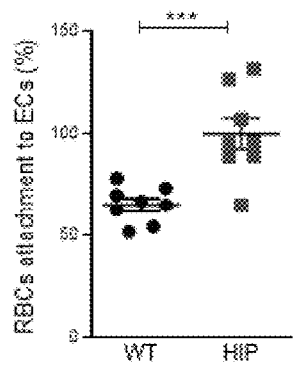
FIG. 22C
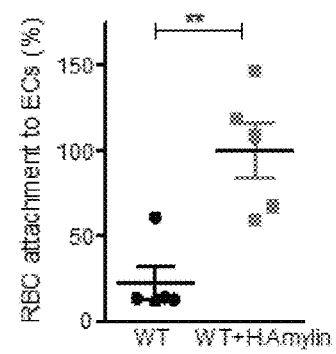
FIG. 22D
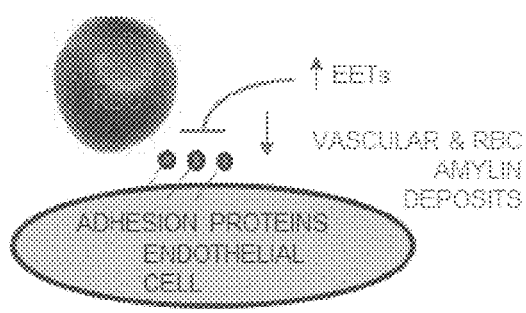
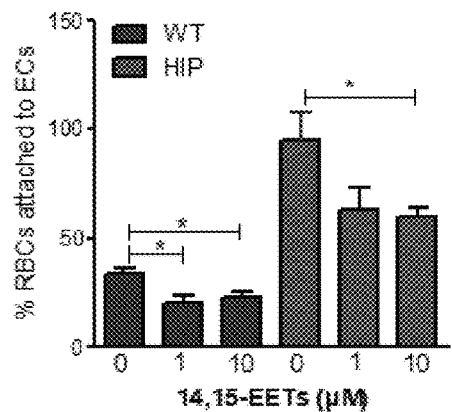
FIG. 22E
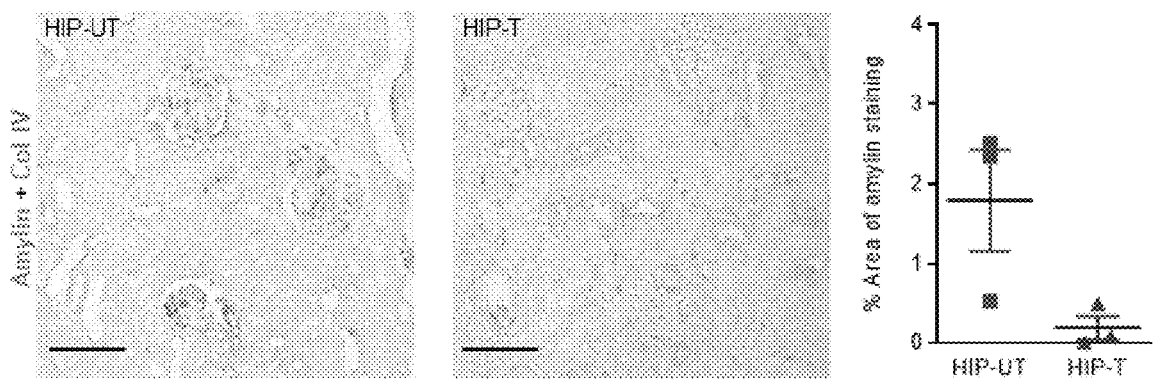
FIG. 22F
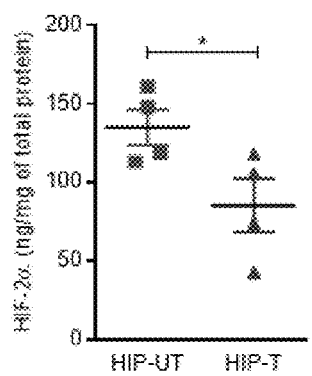
FIG. 22G
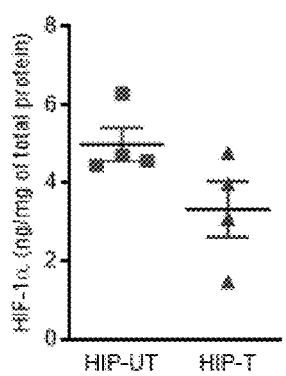

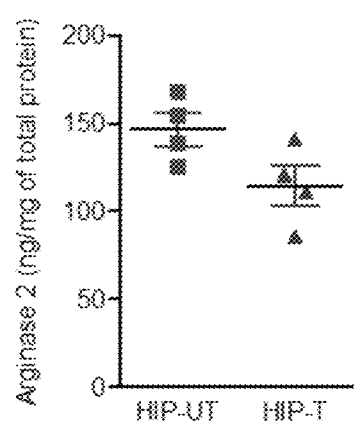 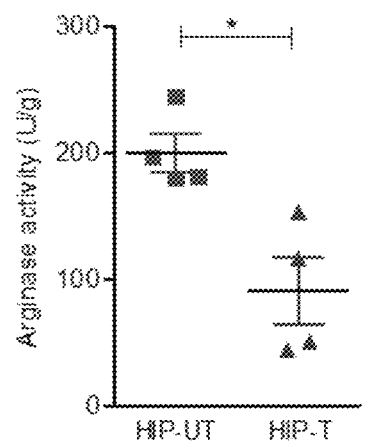
FIG. 32A                    FIG. 32B

Aβ N-terminal Antibody

Aβ C-terminal Antibody

Amylin peptide-
KCNTATCATQRLANFLVHSSNNFGAILSSTNVGSNTY

Immunogen-1 – 5'-CNNFGAILSSTNVGSN-3'   (Amylin C)

Immunogen 2-  5'-CKCNTATCATQRLANFLVHSS-3'   (Amylin N)

Amyloid β peptide-
DAEFRHDSGYEVHHQKLVFFAEDVGSNKGAIIGLMVGGVVIA

Immunogen-1 - 5'-CDAEFRHDSGYEVHHQ-3'   (Aβ N)

Immunogen-2 – 5'-CKLVFFAEDVGSNKGAIIGLMVGGVVIA-3' (Aβ C)

DIAGNOSIS OF DIABETES BY DETECTING AGGREGATED AMYLIN IN ERYTHROCYTES

RELATED APPLICATIONS

This application claims priority from U.S. Provisional Patent Application No. 62/767,131 filed on Nov. 14, 2018, and U.S. Provisional Patent Application No. 62/883,992 filed on Aug. 7, 2019 the entire disclosures of which are incorporated herein by this reference.

GOVERNMENT INTEREST

This invention was made with government support under grant numbers R01HL118474, R01AG053999, R01HL135000, and R01AG057290 awarded by the National Institutes of Health. The government has certain rights in the invention.

TECHNICAL FIELD

The presently-disclosed subject matter generally relates to methods for detecting the presence of amylin in a patient's erythrocytes, determining risk for the development of type II diabetes and comorbidities thereof, and determining effectiveness of treatments for patients at risk for developing type II diabetes and comorbidities thereof. The presently-disclosed subject matter also relates to methods for diagnosing and treating a subject with diseases related to the dysregulation of amylin including heart failure, cancer, stroke, amylin related renal hypoxia, amylin related brain hypoxia, amylin related cardiac hypoxia, microvascular disease, or age-related diseases.

BACKGROUND

Risk of diabetic heart failure (HF) begins years before type-2 diabetes (T2D) is clinically diagnosed and is higher in people with insulin resistance[1-5]. Thus, it is becoming critically important to define early links between HF and T2D and to validate therapeutic targets. Amylin is a pancreatic β-cell hormone co-secreted with insulin[23], plays a role in normal glucose homeostasis[27,28], but it also is amyloidogenic and aggregates quickly when hypersecreted[23]. Conditions associated with hypersecretion of amylin include obesity[29,30], pre-diabetic insulin resistance state[29,30] and early phase of type-1 diabetes[31]. Aggregated amylin is known to cause apoptosis[11,32], oxidative stress[33,34] and inflammation[35,36] in the pancreatic islets, thus contributing to the development of T2D in humans. The inventors found that aggregated amylin is abundantly present in failing hearts of patients with T2D or obesity, but not in controls[6,7]. Recent efforts[15-22] from several labs[15-22] have confirmed that amylin aggregation is abnormally increased in brains[15-21] of patients with T2D and dementia and in failing kidneys[22] of individuals with T2D. The inventors[6-9,16-18,25,26] (and others[14,32,37-39]) showed that rats that overexpress human amylin (3-fold) in the pancreas (HIP rats) develop multiple organ impairments, including heart dysfunction[6-10,25,26]. These impairments are associated with accumulation of aggregated amylin intracellularly. While the inventors interpret these findings to generally support the idea that therapies targeting hyperamylinemia will have a role in diabetes care, clearing aggregated amylin from cells has proven difficult. The scientific premise of the invention is based on accumulating evidence[6-9,11-13,15,17-24,35] showing a role of aggregated amylin in target organ toxicity in humans, the presence of aggregated amylin in the blood of patients with type-2 diabetes[8], iii) data showing that circulating aggregated amylin induces multiple organ impairments in HIP rats[6-9,16-18,25,26,32,38] and mice[37-39], iv) challenges to block amylin aggregation within the pancreatic secretory pathway[23], and v) lack of therapies directed to limit the uptake of circulating aggregated amylin or/and its deleterious effects in the heart.

Because hyperamylinemia coincides with hyperinsulinemia[40], cardiac accumulation of aggregated amylin might be a catalyst of the myopathic response in the pre-diabetic insulin resistance state. Data herein indicates that i) circulating aggregated amylin provokes myocardial microhemorrhages, and ii) the blood level of aggregated amylin increases with the transition from normal glucose homeostasis to impaired glucose tolerance and to overt hyperglycemia. The findings indicate that the interplay between pre-diabetes and hyperamylinemia creates a feed forward pathologic circuit that amplifies cardiac injury by amylin induced disruption of the capillary-myocyte interface (FIG. 1).

Healthy RBCs are flexible and oval biconcave disk shaped, which facilitates the release of $O_2$ while squeezing through the capillaries. Slower moving RBCs result in hypoxia[41-44]

Detection of Cardiac Amylin Deposition.

Proteinaceous deposits immunoreactive for amylin are abundant in myocardial tissues from patients with HF and T2D or obesity, but not in non-failing hearts from lean individuals without T2D (controls)[6,7]. Amylin-positive deposits were identified in blood vessel walls[7], perivascular areas[6,7], myocardial interspaces and inside cardiac myocytes[6,7]. The source of amylin deposited in the heart originates in the pancreas, as no amylin mRNA was found in cardiac tissue or other extra-pancreatic tissues[7,15]. To unambiguously validate the myocardial accumulation of amylin, reverse-phase high performance liquid chromatography (HPLC) and liquid chromatography tandem mass spectrometry (LC-MS/MS) was employed[8]. Based on the retention time of the standard amylin peptide as derived from the HPLC chromatogram, fractions of myocardial tissue lysates likely to contain amylin were collected and immunoblotted for amylin identification. Fractions positive for amylin by Western blot were then further tested by LC-MS/MS. The results convincingly demonstrated that amylin is contained in myocardium in patients with T2D, but not in non-failing hearts from lean subjects without T2D.[8]

Cardiac Phenotypes Associated with Aggregated Amylin.

Amylin from rodents has a decreased propensity to aggregate, which was attributed to proline substitutions at positions 25, 28, and 29[24]. Thus, the innate distinctions between human amylin and rodent amylin species was exploited to assess mechanistically the impact of a "human" hyperamylinemia on cardiac myocytes in a rat model transgenic for human amylin[6-9]. Human amylin-expressing rats were previously used to study complications of T2D in the cardiovascular[6-9,25,26] and central nervous systems[16-18]. TABLE 1 summarizes phenotypic changes in HIP rats. HIP rats have elevated blood levels of aggregated amylin[7,8,16,18] and develop a late-onset T2D-like pathology[32]. Hyperamylinemia is associated with a) cardiac hypertrophy[6,7] (via activation of $Ca^{2+}$-mediated hypertrophy/remodeling signaling), b) diastolic dysfunction[6] (via SERCA downregulation), c) arrhythmias[25,26] (via increased CaMKII activity[25] and altered myocyte $Na^{+26}$), d) inflammation[8] (via increased synthesis of IL-1β[8]), and e) neurologic deficits[16-18] (via neuroinflammation[16], impaired catecholamine synthesis[9], and small blood vessel disease[18]). Confocal microscopy analysis of cardiac tissues from patients with T2D and HF demonstrated the presence of sub-sarcolemmal deposits of amylin[8]. Areas of myocyte amylin deposition were positive for accumulation of reactive aldehydes (4-HNE and MDA), indicating peroxidative damage of membrane lipids. In contrast, amylin-4-HNE/MDA adducts were undetectable in hearts from the control group. Pancreatic tissue (the positive control for amylin deposition) from a diabetic patient also showed amylin-4-HNE adducts, consistent with the role of aggregated amylin in inducing oxidative stress in the pancreas[33,34]. Cardiac tissues from patients with diabetes or obesity showed also IL-1β immunoreactivity in amylin-positive areas[8]. Consistent with findings in human tissues, HIP rat hearts showed sub-sarcolemmal accumulation of aggregated amylin, formation of amylin-4-HNE complexes and increased synthesis of IL-1β[8]. These results were mirrored in Langendorff perfused hearts and normal mice intravenously injected with aggregated human amylin, but not in hyperglycemic rats that secrete wild-type (non-amyloidogenic) rat amylin[8]. Thus, exacerbated synthesis of IL-1β is revealed as an unexpected, but critical stress-activated signaling pathway in response to the interaction of aggregated amylin with myocytes. These results[8] are consistent with the demonstrated role of aggregated amylin in inducing IL-1β release in pancreatic islets[35,36]. In HIP rats, cardiac amylin accumulation provoked sarcolemmal $Ca^{2+}$ leak[6], which increased cytosolic $Ca^{2+}$. In turn, the increase of cytosolic $Ca^{2+}$ triggered the activation $Ca^{2+}$-mediated hypertrophy signaling pathways (CaMKII-HDAC and calcineurin-NFAT). Myocyte $Ca^{2+}$ dysregulation and pathologic $Ca^{2+}$ signaling were replicated in isolated cardiac myocytes incubated with aggregated amylin[6]. These results may explain SERCA downregulation and diastolic dysfunction in HIP rats[6].

TABLE 1

PHENOTYPIC CHANGES IN DIABETIC RATS EXPRESSING HUMAN AMYLIN IN THE PANCREAS

| Heart Function/Structure Alteration | Ref. |
| --- | --- |
| Amylin deposition | 6 |
| Diastolic dysfunction | 6 |
| Eccentric hypertrophy | 7 |
| Dilation | 7 |
| Arrhythmia | 25 |
| Myocyte Ca2+ dysregulation | 6 |
| Elevated myocyte Na+ | 26 |
| Impaired [protein biosynthesis | 9 |
| ROS production | 8 |
| Sarcolemmal lipid peroxidation | 8 |
| Inflammation | 8 |
| Cardioprotection by reducing systemic amylin dyshomeostatis | 7 |
| Brain Function/Structure Alteration | |
| Amylin deposition | 16 |
| Learning & memory deficits | 16,18 |
| Vestibulomotor dysfunction | 16,18 |
| Microhemorrhages | 18 |
| White matter rarefaction | 18 |
| Blood-brain barrier injury | 17 |

Sex Differences.

Female HIP rats develop hyperglycemia and neurologic deficits later in life compared to males (i.e., ~12 months vs. ~18 months of age)[18]. To test further a possible sex difference in amylin pathology, amylin knockout (AKO) male and female mice which were intravenously infused with either human amylin (i.e, the aggregated form) or non-amyloidogenic (i.e., monomeric) rodent amylin (2 pg/g body weight, q.d., 7 days) were tested[10]. AKO mice infused with human, but not rodent amylin, showed amylin deposits in the myocardium. Cardiac amylin level was larger in males compared to females, indicating a sex-dependent effect which might be estrogen-dependent. These results[10] are consistent with previous data[51] indicating that pancreatic amylin deposition is more abundant in men compared to women. This sex difference in amylin pathology was attributed to increased insulin resistance in men[52,53]. Ovariectomy or employing older female mice (as in HIP rats[18]) might mitigate the sex difference in amylin-induced pathology. Sarcolemmal $Ca^{2+}$ leak and $Ca^{2+}$ transients were increased in myocytes isolated from male AKO mice infused with human amylin while no significant changes occurred in either females injected with human amylin or in rat amylin-infused mice[10]. Indeed, previous studies demonstrated sex differences in cardiac myocyte ion channels[54-58], $Ca^{2+}$ cycling[59,60], contractions[59] and metabolism[61,62], which may contribute to the differential effects of amylin stress. These results[10] indicate that aggregated amylin accumulates preferentially in male vs. females and is an independent contributing mechanism to myocyte $Ca^{2+}$ dysregulation in T2D.

EETs are formed by endothelial cells[45-47] and have demonstrated ability to reduce proteinaceous deposition on blood vessel walls[48,49]. Endogenous levels of EETs were elevated in pre-diabetic HIP rats[7] by treatment with an inhibitor of Soluble epoxide hydrolase (sEH), the enzyme that degrades EETs[45]. Rats in the treatment group showed lower amylin incorporation into RBCs and cardiac myocytes and improved heart function. Using a sEH inhibitor to increase the levels of EETs in diabetic HIP rats proved less efficient[7].

Oxygen is essential for cell function and cell survival. RBCs deliver oxygen to cells and tissues via mechanisms that involve the passage of RBCs through capillaries. This process is enabled by the viscoelastic properties of the RBCs, which allow them to be deformed within capillaries. In type-2 diabetes, the oxygen-carrying capacity of RBCs and the integrity and stability of the capillaries decline, exacerbating the risk of tissue hypoxia and end organ malfunction. The underlying mechanisms are complex and incompletely understood.

Physiological responses to low oxygen levels are primarily driven by the stabilization of the α subunits of the hypoxia-inducible transcription factors HIF-1 and 2. HIF-2 regulates the hypoxia response by elevating the renal expression of EPO, a hormone that signals an increased demand for RBCs from the bone marrow, which then increases the production of RBCs. Stabilization of HIF-2α also induces arginase expression in vascular endothelial cells. Because arginase has the same substrate (L-arginine) as nitric oxide (NO) synthase, increased arginase production/activation may reduce NO availability. Depleted NO production impairs relaxation of the blood vessels and affects microvascular autoregulation. Thus, increased EPO coupled with arginase-NO dysregulation constitutes one of the multiple molecular derangements linking systemic hypoxia with microvascular dysfunction.

Metabolic derangements that occur before the development of overt hyperglycemia may induce microvascular dysfunction. In prediabetes, pancreatic β-cells compensate for insulin resistance by increasing the secretion of insulin (hyperinsulinemia). Amylin (also known as islet amyloid polypeptide; IAPP), is a 37-amino acid peptide synthesized and co-secreted with insulin in response to physiological stimuli. It is normally soluble, crosses the blood brain barrier and binds to neurons in the feeding centers participating in the regulation of gastric fluxes. Amylin from humans and a few other species, including cats, dogs and monkeys, but not rodents, has an increased propensity to aggregate, forming amyloid (i.e., amylin dyshomeostasis). This triggers β-cell apoptosis by mechanisms involving incorporation of aggregated amylin into cellular membranes. Amylin deposition is present in failing hearts and kidneys of patients with type-2 diabetes and in brains of humans with dementia. Rats develop type-2 diabetes linked to amylin dyshomeostasis (i.e. the HIP rat model for type-2 diabetes) develop heart dysfunction and neurological deficits sooner than age- and blood glucose-matched rats that develop type-2 diabetes in the absence of amylin dyshomeostasis (i.e. the UCD rat model for type-2 diabetes). The upregulation of epoxyeicosatrienoic acids (EETs) in endothelial cells appeared to protect against cardiac amylin accumulation in HIP rats, which correlated with improved heart function. The impact of elevated blood levels of amylin on blood cells and the microvasculature remains unknown.

The hypothesis that systemic amylin dyshomeostasis alters the interaction between RBCs and capillaries leading to hypoxic-ischemic tissue injury was tested. To test this hypothesis, the amylin levels in RBCs from humans with and without diabetes, and used transgenic rats, RBC transfusions and pharmacological tools for mechanistic studies was measured.

Human Amylin and human Aβ polyclonal antibodies to develop the detection of Amylin and Aβ along with their oligomers were developed in diseased and normal condition. Rabbit has been used as a host to generate the antibodies. First, a bioinformatics analysis was carried out to determine the most immunogenic regions in Amylin and Aβ peptides. N-terminal and C-terminal regions from both Amylin and Aβ were used as an immunogen to generate the antibodies. Generated antibodies were used in ELISA to check the titer. The 1:100000 titer for each antibody worked. These antibodies were successfully detected the native protein in Immunohistochemistry. These antibodies were used in western blot where Aβ antibody was detecting monomer. These antibodies specifically detect the native form of human Amylin peptides.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter generally relates to methods for detecting the presence of amylin in a patient's erythrocytes, determining risk for the development of type-2 diabetes, and determining effectiveness of treatments for patients at risk for developing type-2 diabetes and comorbidities thereof.

The present invention also relates to a method of detecting amylin in a patient, said method comprising: obtaining a blood sample from a human patient; detecting whether amylin is present in the erythrocytes by conducting an amylin ELISA; and using the amylin ELISA to determine the amount of amylin in the patient's erythrocytes. In some embodiments of the present invention, the patient is treated by increasing circulating Epoxyeicosatrienoic acids (EETs) if the amount of amylin in the patient's erythrocytes is higher than the amount of amylin in healthy control erythrocytes. In further embodiments of the present invention, the method also includes diagnosing the patient with pre-diabetes if the amount of amylin in the patient's erythrocytes is higher than the amount of amylin in healthy control erythrocytes and lower than the amount of amylin in diabetic control erythrocytes; and treating the patient with lifestyle changes, biological, genetic, or pharmacological intervention suitable for the treatment of pre-diabetes. In other embodiments of the present invention, the patient is diagnosed with pre-diabetes when the amount of amylin in the erythrocytes is between about 1 ng/g and about 2 ng/g total protein.

Other embodiments of the present invention include a method for diagnosing the patient with type-2 diabetes, if the amount of amylin in the patient's erythrocytes is higher than the amount of amylin in healthy control erythrocytes and pre-diabetic control erythrocytes; and treating the patient with therapeutically effective amount of an anti-diabetic therapeutic. In further embodiments, the patient is diagnosed with type-2 diabetes when the amount of amylin in the erythrocytes is greater than or equal to about 2 ng/g total protein.

In some embodiments of the present invention, a patient is diagnosed as at risk for developing a comorbidity of type-2 diabetes, if the amount of amylin in the patient's erythrocytes is higher than the amount of amylin in healthy control erythrocytes; and treating the patient by increasing circulating Epoxyeicosatrienoic acids (EETs). In further embodiments, circulating EETs are increased by administering an effective amount of an inhibitor of soluble epoxide hydrolase. In other embodiments, the patient is diagnosed with a comorbidity of type-2 diabetes when the amount of amylin in the erythrocytes is about 1.7 ng/g total protein or greater. In some embodiments of the present invention, comorbidities of type-2 diabetes is cancer, heart failure, or stroke. In further embodiments, the patient is treated with an effective amount of an anti-cancer therapeutic, a heart failure therapeutic, or a therapeutic for the treatment of stroke.

Also described herein is a method of diagnosing the patient with amylin related hypoxia if the amount of aggregated amylin in the patient's erythrocytes is higher than the amount of aggregated amylin in healthy control erythrocytes; and treating the patient by increasing circulating Epoxyeicosatrienoic acids (EETs). In some embodiments of the present invention, the amylin related hypoxia is renal, cardiac, or brain hypoxia. In further embodiments of the present invention, circulating EETs are increased by administering an effective amount of an inhibitor of Soluble epoxide hydrolase.

One embodiment of the present invention is a method to determine the effectiveness of biologic, lifestyle changes, or pharmaceutical intervention in preventing complications in a patient with type-2 diabetes or co-morbidity thereof, or amylin related renal hypoxia, said method comprising:

obtaining a first blood sample from the patient diagnosed with type-2 diabetes or co-morbidity thereof, or amylin related renal hypoxia; using an aggregated amylin ELISA to determine the amount of aggregated amylin in the patient's erythrocytes; administering an effective amount of biologic, lifestyle change, or pharmacologic intervention; obtaining a subsequent blood sample from the patient; using the aggregated amylin ELISA to determine the amount of aggregated amylin in the patient's erythrocytes; and determining the intervention is effective if the amount of aggregated amylin in the erythrocytes in the subsequent sample is less than the amount of aggregated amylin in the erythrocytes in the first sample.

In many embodiments of the present invention, the treatment increases circulating Epoxyeicosatrienoic acids (EETs).

BRIEF DESCRIPTION OF THE DRAWINGS

FIGS. 20A-20H show pathophysiological changes induced by amyloid-forming amylin in RBCs. (20a) Hemoglobin levels in RBCs from WT, HIP and UCD rats (n=11 rats/group). (20b) Oxygen dissociation curve for RBCs from WT, HIP and UCD rats (n=5 rats/group). (20c) Representative example of cell shape distribution of RBCs from WT (orange), UCD (blue) and HIP (pink) rats (n=6 rats/group) and the Pearson coefficient of dissymmetry (PCD) calculated from these data. (20d) Percentage of RBC hemolysis in hypo-osmotic solutions. The NaCl concentration for 50% hemolysis of WT, HIP and UCD RBCs is indicated in the inset. (n=4 rats/group). (20e and 20f) Representative images of co-staining for amylin and collagen IV (Col IV) in kidney tissue sections showing amylin deposition in arterioles and interstitial tissue (20e) and in the glomerulus (20f) in diabetic HIP rats but not in diabetic UCD rats (n=3 rats/group). (20g) Representative images of co-staining for amylin and ionized calcium binding adaptor molecule 1 (IBA1) in kidney tissue sections from diabetic HIP and diabetic UCD rats (n=3 rats/group). (20h) Representative images of staining for the cluster of differentiation 68 (CD68; ED1) in kidney tissue section from diabetic HIP and diabetic UCD rats (n=3 rats/group). (Scale bar 50 μm) *P<0.05; **P<0.01 by One-way ANOVA with Tukey's post-test (20a and 20c).

FIGS. 22A-22G show effect of increasing endogenous EETs on RBC-capillary coupling and renal hypoxia signaling. (22a) Average numbers of RBCs adhered to culture vascular endothelial cells when fixed hematocrit of RBCs flowed over cultured EC at constant rate for constant time (n=3/group). (22b) Analysis of the adhesion of RBCs isolated from HIP rats and WT littermates to cultured vascular endothelial cells (n=8/group). (22c) Adhesion of WT rat RBCs to cultured vascular endothelial cells with/without incubation with recombinant human amylin (50 μM) for 2 hours (n=5/group). (22d) Attachment of RBCs from WT and diabetic HIP rats to vascular endothelial cells in the absence or in the presence of various amounts of EETs (n=8 rats/group). (22e) Representative images of staining for amylin and Col IV in kidney sections from diabetic HIP rats (HIP-UT) and diabetic HIP rats with pharmacologically upregulated EETs (HIP-T). The scatterplot shows the percentage of the tissue area that is positive for amylin (n=3 rats/group). (22f-22g) Protein levels of HIF-2α (22f) and HIF-1α (22g) in whole kidney tissue homogenate from rats in the HIP-UT and HIP-T groups (n=4 rats/group). *P<0.05; P<0.01; *P<0.001 by t-test.

FIG. 23A-23I1 show altered oxygen sensing in kidneys following transfusion with amylin-loaded RBCs (23a) Plasma EPO levels in WT rats transfused with RBCs from i) WT rats (n=7); ii) diabetic UCD rats (n=7) and iii) diabetic HIP rats (n=7). (b and c) Protein levels of HIF-1α (23b) and HIF-2α (23c) in renal tissue homogenate from the rats described in (23a). (23d) Representative images of amylin and glycophorin A co-staining (left panel) and of amylin and hemoglobin co-staining (right panel) in RBCs from UCD rats infused with aggregated human amylin (daily injection of 0.08 μg/g body weight for 7 days; n=3 rats/group). (23e) Plasma EPO levels in diabetic UCD rats (n=3) at baseline and at the end of the acute intravenous treatment with aggregated human amylin (hA). (23f-23g) Protein levels of HIF-2α and HIF-1α (23f) and arginase-1 and arginase-2 (23g) in renal tissue homogenates from diabetic UCD rats injected with human amylin versus non-injected diabetic UCD control rats (n=3 rats/group). (23h) Cartoon illustrating the proposed mechanism through which "human" hyperamylinemia exacerbates hypoxia signaling in diabetic rats with pancreatic expression of non-amyloid forming amylin rat amylin (UCD rats). *P<0.05; P<0.01; *P<0.001 by One-way ANOVA with Tukey's post-test (23a-23c) or two-tailed t-test (e-g).

FIGS. 32A-32B show reduced amylin deposition in kidneys correlated with partially reduced imbalance of arginase expression and arginase activation in HIP rat kidney tissues. (n=4 rats/group). Data are means+SEM. *P<0.05.

Figure 1:
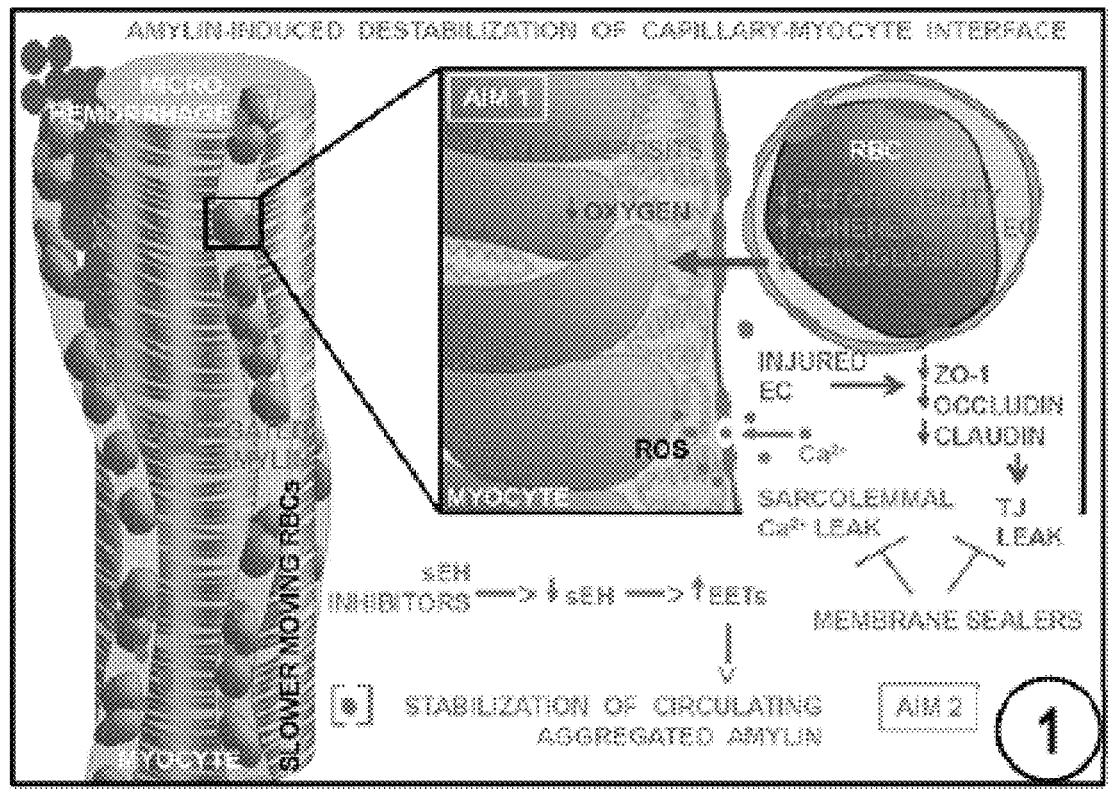
FIG. 1. shows schematic illustrating the amylin-induced destabilization of capillary-myocyte interface.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a biomarker" includes a plurality of such biomarkers, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, width, length, height, concentration or percentage is meant to encompass variations of in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the term "subject" refers to a target of administration. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A "patient" refers to a subject afflicted with a disease or disorder. The term "patient" includes human and veterinary subjects.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term genetic manipulation includes methods that result in changes to a patient's protein levels or protein activity at the genetic level which includes but is not limited to: genetic knock-down, genetic knockout, genetic mutation, genetic silencing by miRNA, siRNA, or shRNA, and CRISPR derived base editor technology.

As used herein, the term "pharmacological intervention" includes but is not limited to administering to a patient small molecules, natural products, compounds, pharmaceutical mixtures and pharmacological agents in a pharmaceutically acceptable carrier. For example, it is commonly understood in the art that insulin, metformin, sulfonylureas, meglitinides, GLP-1 receptor agonists, DPP-4 inhibitors, and SGLT2 inhibitors are all pharmacological interventions for the treatment of diabetes.

As used herein the term biological intervention includes but is not limited to: administering to a patient antibodies, antibody fragments, stem cells, proteins, peptides, viral carriers, various method of genetic manipulation, and biologic agents in a pharmaceutically acceptable carrier.

As used herein the term "lifestyle changes" includes but is not limited to dietary changes, exercise regiments, or the implementation of nutritional programs commonly recognized in the art to serve as therapy for metabolic diseases which include pre-diabetes and diabetes.

As used herein, the terms "comorbidities of type-2 diabetes" or "type-2 diabetes and comorbidities thereof" includes certain diseases well recognized in the art in which patients with type-2 diabetes are known to be at increased risk of developing. These common comorbidities include such diseases as obesity, heart failure, cancer, stroke and the like. Comorbidities may also be referred to, in the art, as diabetic complications.

As used herein, inhibitors of Soluble epoxide hydrolase can include reversible and irreversible inhibitors, full or partial inhibitors that directly or indirectly bind to soluble epoxide hydrolase. It is well known in the art that UC1153, GSK2256294, and SMTP-7 are soluble epoxide hydrolase inhibitors.

As used herein, an anti-diabetic therapeutic includes common treatments known in the art including but not limited to: insulin, metformin, sulfonylureas, meglitinides, GLP-1 receptor agonists, DPP-4 inhibitors, SGLT2 inhibitors and combinations thereof.

As used herein, anti-cancer therapeutics include but are not limited to the following general classes of therapeutics as is well known in the art: alkylating agents, anthracyclines, cytoskeletal disruptors, epothilones, histone deacetylase inhibitors, topoisomerase I and II inhibitors, kinase inhibitors, nucleoside analogues, peptide antibiotics, platinum agents, retinoids, vinca alkaloids, derivatives thereof, and combinations thereof.

As used herein, heart failure therapeutics include but are not limited to: Aldosterone antagonists, ACE inhibitors, ARBs (angiotensin II receptor blockers), ARNIs (angiotensin receptor-neprilysin inhibitors), Beta-blockers, Blood vessel dilators, Calcium channel blockers (unless systolic heart failure), Digoxin, Diuretics, Heart pump medication, Potassium or magnesium, Selective sinus node inhibitors, and combinations thereof.

As used herein, a therapeutic for the treatment of stroke, including but not limited to ischemic stroke, includes: anticoagulants, anti-platelet therapeutics, tissue plasminogen activator, statins, angiotensin-converting enzyme (ACE) inhibitors, beta-blockers, calcium channel blockers, and combinations thereof.

The presently-disclosed subject matter is further illustrated by the following specific but non-limiting examples. The following examples may include compilations of data that are representative of data gathered at various times during the course of development and experimentation related to the present invention.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter is further illustrated by the following specific but non-limiting examples. The following examples may include prophetic examples, notwithstanding the numerical values, results and/or data referred to and contained in the examples. The following examples may include compilations of data that are representative of data gathered at various times during the course of development and experimentation related to the present invention.

EXAMPLES

Methods
Animal Models.

The HIP rat is a Sprague-Dawley (SD) rat that expresses human amylin in pancreatic β-cells on the insulin II promoter. HIP rats have a ~3-fold increase of amylin secretion[38], similar to humans with hyperamylinemia[29,30]. HIP rats have amylin deposition in pancreas[38] and peripheral organs[6,16,71,] including the heart[6]. Quantitative real-time PCR showed no presence of human amylin mRNA in the HIP rat heart[7], indicating that amylin deposited in the heart comes from the circulation, as observed in humans[6,7]. In the present invention HIP rats with eight backcrosses to SD rats are used. Amylin oligomerization and deposition in the pancreas leads to a gradual decline of β-cell mass, glucose dysregulation by ~7-9 mo of age[16] and T2D by 10-12 mo of age[16]. Insulin and amylin secretion are maximum at ~8 mo of age, followed by a decline with the development of T2D[16]. Symptoms in terminal stages include lethargy and neurological deficits[18]. Sudden death and arrhythmia[25] are more frequent in male HIP vs. WT littermate rats. Female HIP rats show overt hyperglycemia later in life (i.e., 18 mo of age), as previously reported[18]. Physical deterioration is milder in females compared to male HIP rats[18]. AKO mice have been used previously[10] to investigate the interaction of exogenous amylin (aggregated vs. monomeric) with the sarcolemma. To circumvent species-specific paradigms in comparing mice vs. rats, the amylin knockout (AKO) rats, were generated (see Ref 18, for details).

Diet Interventions.

High-fat diet (60% kcal as fat; Research Diets, Inc) or chow ad libitum are used to discriminate effects of hyperamylinemia from known cellular and metabolic disturbances in diabetic heart.

RBC Amylin:

Amylin levels in RBCs from HIP and WT rats is measured (both males and females) in longitudinal studies. Flow cytometry (Becton Dickinson LSRII; as in FIG. 4A) is used to measure amylin deposition on RBCs, followed by ELISA, Western blot and mass spectroscopy of amylin in RBC lysates, as described previously[7,8,16-18]. The inventors developed a specialized ELISA[74] and can measure amylin levels in up to 400 RBC samples in parallel, which is ideal for longitudinal studies. Because diabetes develops later (by 6 mo) in female vs. male HIP rats, it is anticipated that the RBC amylin level will increase in males, but not significantly change in female HIP rats (until 16-18 mo. of age), suggesting an estrogen effect.

Amylin Uptake.

To investigate effects on RBC amylin uptake induced by changes in the metabolic milieu, high-fat diet in HIP vs. WT rats were tested. Rats of 6 mo. of age (normal blood glucose levels in HIP rats) were fed insulinogenic or chow diet ad libitum for 6 mo. and monitored as described herein. Characteristic histograms for RBC amylin levels are derived both at baseline and with longitudinal data.

Figure 4A:
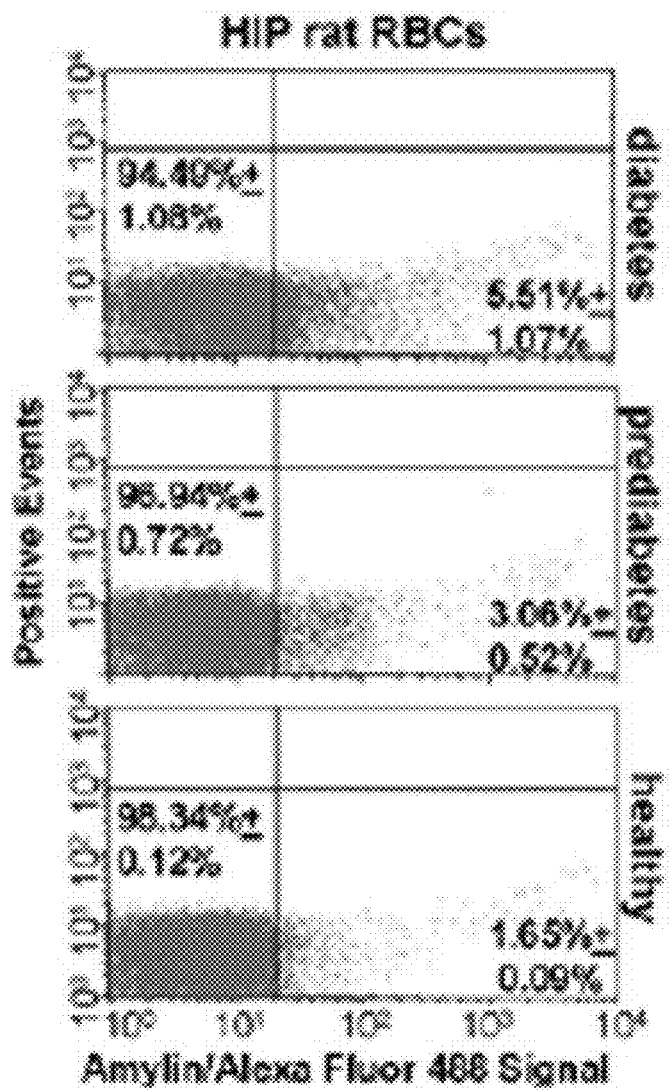
FIGS. 4A-4E. show characterization of amylin in RBCs from HIP rats that are healthy, prediabtic, or diabetic. Amylin in RBCs from HIP rats with normal blood glucose (healthy), prediabetes (PD) or diabetes (D) measured by flow cytometry analysis 4A), western blot (cropped gel; 4B) and ELISA 4C). Cell shape changed in RBCs from HIP v. WT rats and in WT rat RBCs incubated with human amylin (50 μM) for 2 hours, as measured by flow cytometry (PCD—Pearson coefficient of dissymmetry; 4D). The total amount of hemoglobin in 100 μL RBCs suspension measured spectroscopically was lower in HIP v. WT rats 4E).
Figure 4B:
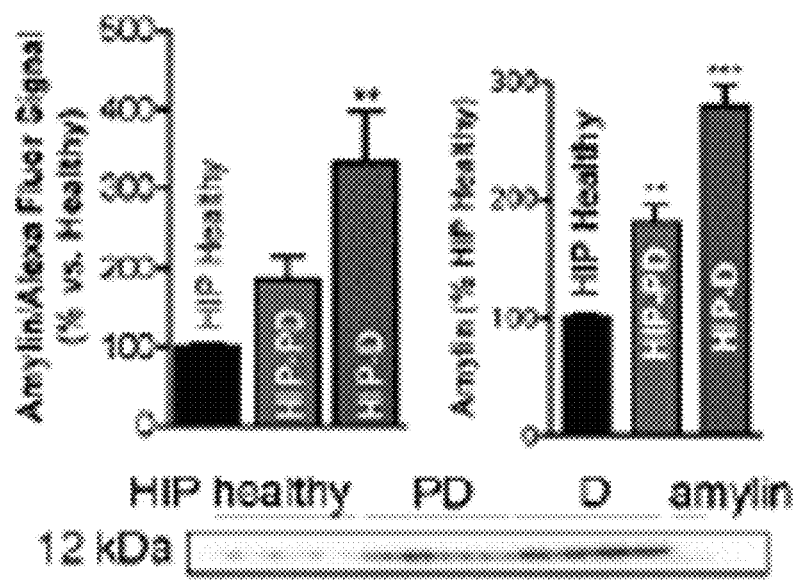
Figure 4C:
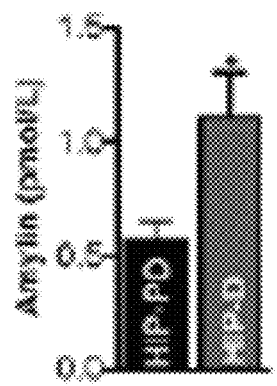
Figure 4D:
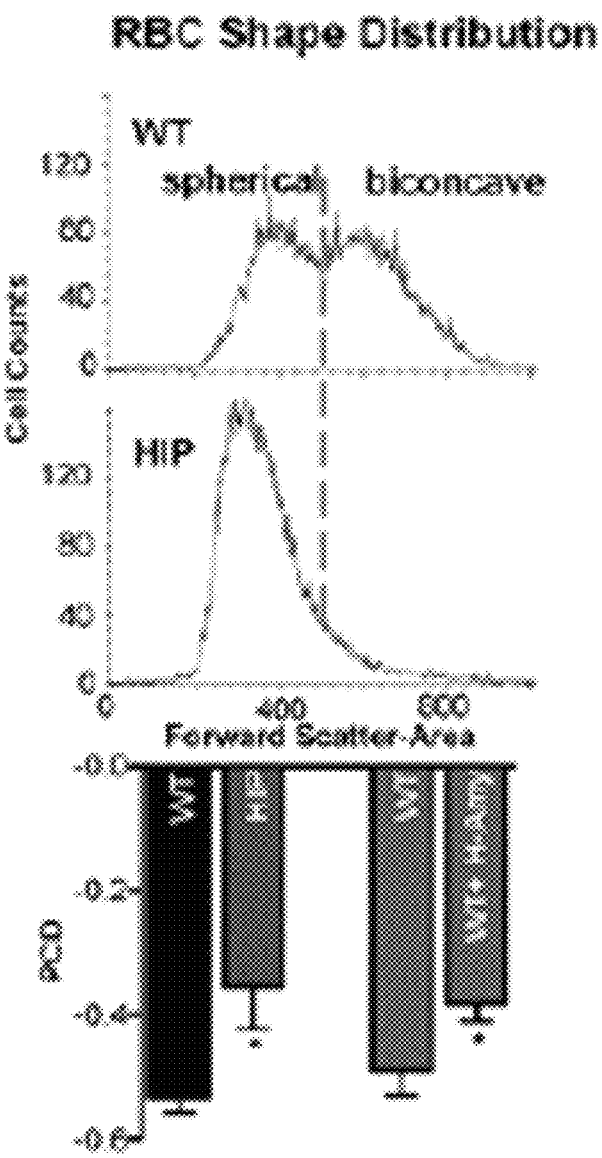

RBC Deformability:

In all rat groups (±high-fat diet), the RBC shape distributions are analyzed by FACScan flow cytometry (Becton Dickinson LSRII) as a function of characteristic RBC amylin levels, as in FIG. 4D. The Pearson coefficient of dissymmetry (PCD) shown in FIG. 4D reflects the sphericity of RBCs (PCD=0 indicates RBC spherical shape). The data (FIG. 4D) suggest that amylin deposition on the RBC surface (or incorporation of amylin inside the cell) negatively affects the RBC deformability.

Figure 4E:
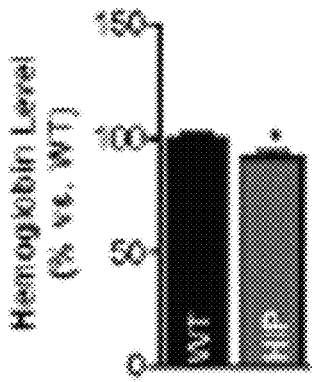

RBC Hb and $HbO_2$ Levels:

RBC specimens from each rat group will be suspended at a hematocrit of 2.5% in HBSS/A, followed by the incubation with 0.5% sodium dodecyl sulfate (SDS) for 5 hours. The total amount of Hb in 100 μL RBCs suspension is calculated from the optical density measured by a spectrophotometer (absorption peak at 410 nm, as in FIG. 4E). Hb level measured in FIG. 4E is the sum of oxygenated Hb ($HbO_2$) plus deoxygenated Hb mass. $HbO_2$ and Hb have different absorption spectra (maxima at 410 nm and 430 nm, respectively), which is used to estimate amylin induced changes in $HbO_2$ and Hb RBC content. All RBC samples are tested for Hb levels using high-performance liquid chromatography (HPLC), as described previously[8].

Adherence of Amylin-Loaded RBCs to Capillary Endothelium:

RBCs collected from each HIP rat group (normal, pre-diabetes, diabetes, ±high-fat diet) are infused into AKO rats (300 μL RBCs, daily, 7 days, q.d., via the tail vein). Because diabetes develops later (by 6 mo) in female vs. male HIP rats, AKO rats are matched for age and sex to HIP rats providing the RBCs for infusion. At the end of infusion period, rats are sacrificed, perfused with saline through a catheter implanted into the right external jugular vein to wash out the blood from blood vessels, followed by heart collection and paraffin embedding. Confocal microscopy is used to identify the attachment of amylin-loaded RBCs to vascular endothelium (as in FIG. 5A). Before analysis, heart sections are incubated with 1% Sudan black to block autofluorescence. Control sections with either omitted primary or secondary antibodies are used to establish specific staining. The co-localization of amylin, glycophorin A and collagen IV (as in FIG. 5B) signifies HIP rat RBCs attached to the vascular endothelium. To further investigate the relationship between RBC amylin level and RBC stickiness, ex vivo experiments are performed. Cardiac microvascular endothelial cells are used from WT adult SD rats (RA-6024, Cell Biologics, IL). The cells are plated on 96-well plate coated with cell attachment factor solution (123-100, Sigma, MO), allowed to attach for 24 hours and used for experiment when they reached 70%-90% confluency. HIP rat RBCs collected from the same groups as in above are gently layered on confluent endothelial cells and incubated at 37° C. for 40 minutes. The plate is then inverted and allowed to sit for an additional 30 minutes at 37° C. With the plate maintained in the inverted position, the adhesive sheet will be removed followed by the measurement of the Hb content (as described below) from the optical density (with a spectrophotometer). Adherence is calculated as percentage of optical density of adhered Hb (as in FIG. 5C).

Amylin Deposition in Capillaries:

Immunohistochemistry methods are used to identify amylin deposition in cardiac blood vessels and confocal microscopy to identify the anatomical localization of amylin, as before[6,7].

Figure 6:
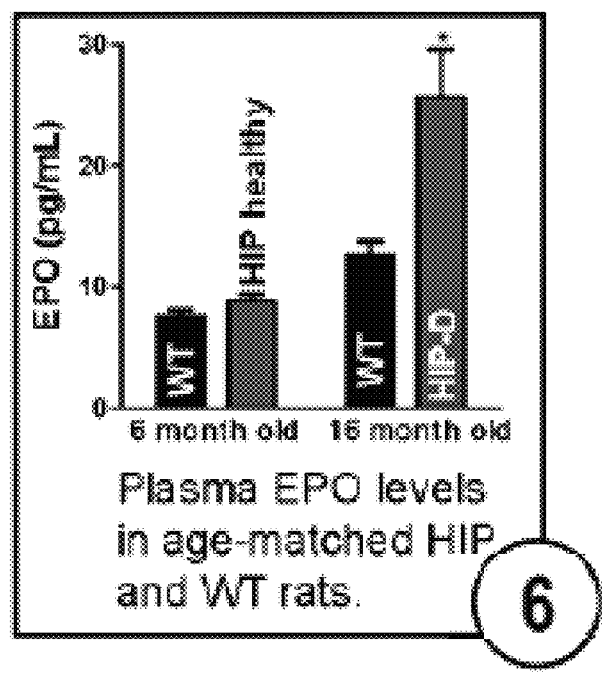
FIG. 6. shows characterization of plasma EPO levels from healthy HIP rats and age-matched HIP diabetic rats.
Figure 7:
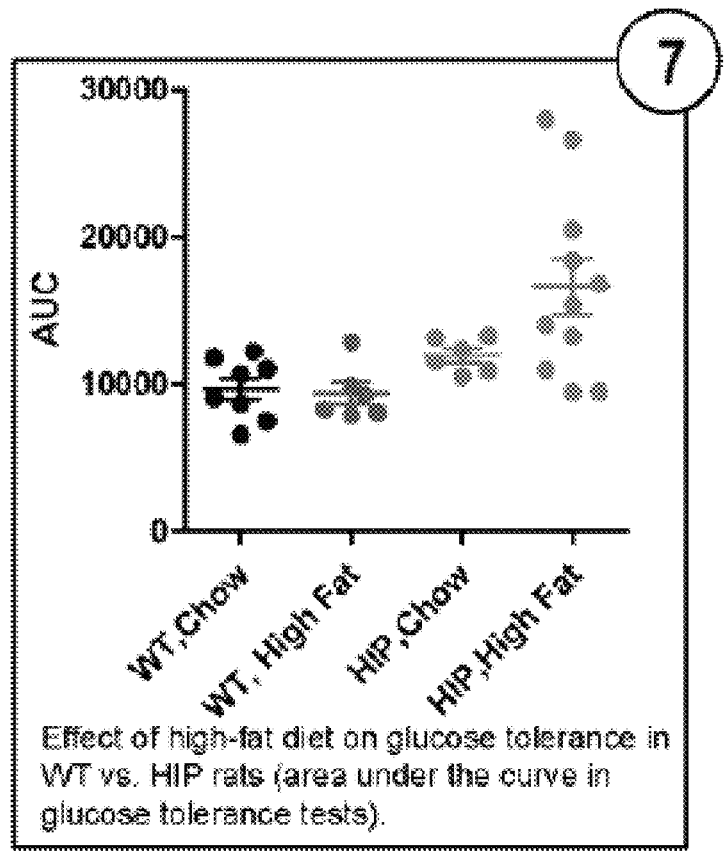
FIG. 7. shows glucose tolerance of WT and HIP rats fed a normal or high fat diet.
Figure 8A:
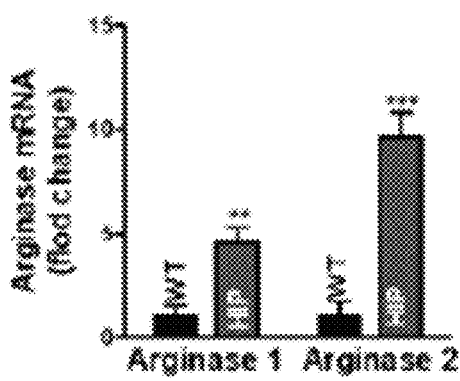
FIGS. 8A-8C. show Arginase 1 & 2 8A) expression, 8B) protein levels, and 8C) activity in cardiac tissue from WT and HIP rats.
Figure 8B:
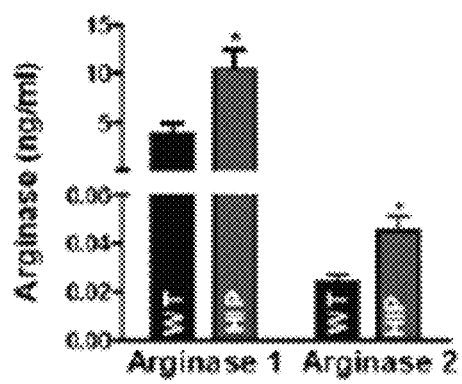
Figure 8C:
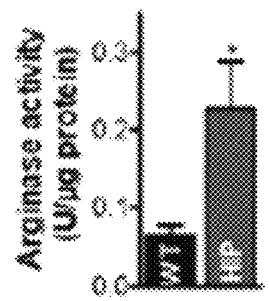

Hypoxia:

As the endpoint, plasma EPO levels (by ELISA; as in FIG. 6) and cardiac hypoxia markers in all rat groups are measured. Under hypoxia, HIF-1α is stabilized and moves into the nucleus, where it regulates transcription of genes whose protein products increase oxygen delivery or facilitate metabolic adaptation to hypoxia[75-77]. The VHL/HIF oxygen-sensing pathway and HIF-1 markers[75-77] in cardiac tissue, including VEGF-A, PGK1 and NOS, using qRT-PCR for expression and ELISA for protein levels is also investigated. Longer term response to hypoxia (which may be the case of diabetic HIP rats) is HIF-2a dominated[77]. HIF-2a regulates EPO[73] (which is upregulated in HIP rats; FIG. 6) and Arginase (Arg)[78]. Arg1 & Arg 2 is measured (using qRT-PCR for expression and ELISA for protein levels; as in FIGS. 8A,B), Arg activity (using Arginase assay kit; as in FIG. 8C) and NO availability (by ELISA) in cardiac tissues from all rat groups.

Structural Integrity and Stability of Myocardial Capillaries.

HIP and WT rats and AKO rats infused with either aggregated amylin or monomeric (functional) amylin was investigated. Anatomical distribution of aggregated amylin (capillary vs. myocardial interstices) is assessed by immunohistochemistry, as previously described[6-8]. The co-localization of amylin deposits, inflammation and microhemorrhages by serial staining of myocardial tissue with amylin antibody, inflammatory markers (IBA-1 and ED1) and Prussian blue (as in FIGS. 9 & 10) was tested in all rat groups. The distribution of aggregated amylin relative to myocardial capillaries and sarcolemma is assessed by using cryo-immunogold labeling. For this, freshly isolated heart samples are incubated overnight in 1.85M sucrose/20% PVP-10/50 mM Hepes pH 7.4. Tissue cuts will be mounted on an aluminum pin and quick frozen in liquid nitrogen. Ultrathin sections are collected on nickel grids with plastic/carbon film and stained with antibodies. The secondary antibodies are conjugated to 5, 10 or 12 nm gold particles. Imaging is done at the EM facility at UK using a transmission EM (JEM-1230; JEOL, Japan) operated at 120 keV, as in previously reported[7].

Figure 9A:
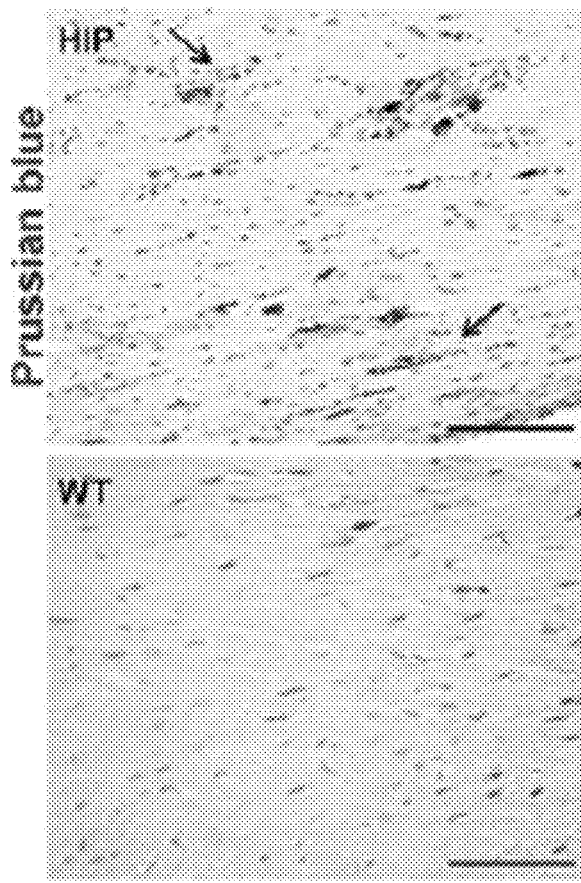
FIGS. 9A-9E. show structural integrity and stability of myocardial capillaries. 9A) Prussian blue staining showed microhemorrhages in myocardial tissue from a 15 mo. old HIP rat, but not in an age matched WT rat. (9B, 9C) Same as above in WT rats infused with HIP rat RBCs v. WT rat RBCs; scale bar, 20 μm. 9D) Western blot analysis of tight junction proteins in HIP v. WT rats. 9E) Amylin in myocardial vcapillaries isolated from HIP v. WT rats (ELISA).
Figure 9B:
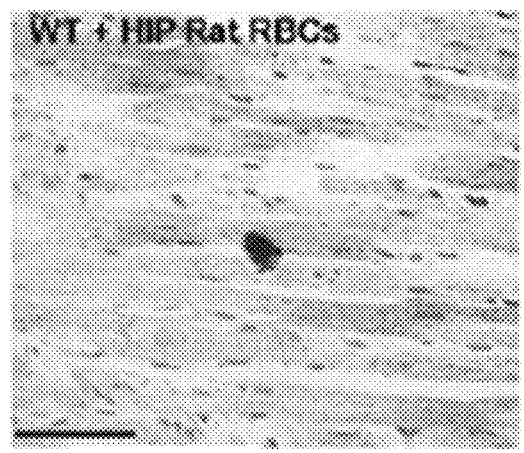
Figure 9C:
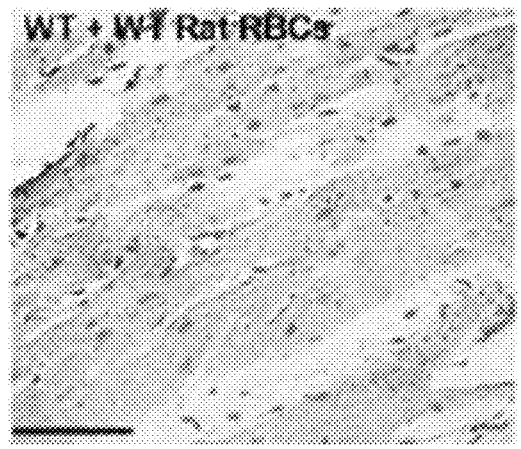
Figure 9D:
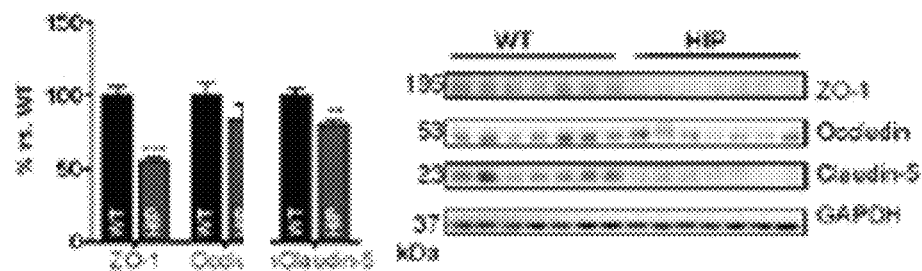

Endothelial Basement Membrane Structure (immunostaining for collagen IV, as in FIG. 10A) and mural cell coverage of myocardial capillaries (immunostaining for CD31, caveolin and ulex europaeus, as in FIG. 10C) is investigated in groups. Altered permeability of myocardial capillaries is assessed by comparing the expression (via qRT-PCR) and protein levels (Western blot, immunoprecipitation and/or ELISA) of components of adherens junctions (vascular endothelial cadherin; Cdh5, and α-actinin; Actn) and tight junctions (claudins, occludin and ZO) in isolated myocardial capillaries from HIP vs. WT rats (as in FIG. 9D). For isolation of capillaries, myocardial tissues in liquid nitrogen are snap frozen, minced into small pieces in ice cold cPBS and then homogenized in ice cold cPBS using glass homogenizer. The homogenates are added into ficoll solution (30%). Samples are mixed by gently inverting tubes and then centrifuged (at 5800 g for 20 minutes at 4° C.). Supernatants are discarded and the pellets are re-suspended in ice cold cPBS with 1% BSA. Suspensions are passed through 300 micron nylon mesh strainer. Glass beads and pellet suspension are added on the top of column, allowed for 1-2 min to settle and passed through column with the rate of one drop per second. Beads are inverted into 100 mL beaker and 20 mL cPBS with 1% PBS and then centrifuged (500 g for 5 minutes at 4° C.). After centrifugation pellets are re-suspended in ice cold cPBS. Capillaries are stained with Texas Red dye and quality is assessed under confocal microscope. (FIG. 9D).

Sarcolemmal Processes and Myocyte Viability:

Cardiac myocytes were isolated from rats in all rat groups. Isolated myocytes are used for testing myocyte accumulation of amylin (by ELISA and Western blot, as shown before[8,10]), sarcolemmal structural integrity (dye leakage assay, electron microscopy, LC-MS/MS and fluorescent markers) and myocyte $Ca^{2+}$ cycling (see below). Each experiment is performed on hearts/myocytes from a number of rats/group. Calculation of the minimum sample size with a two-tail t-test considering $\alpha=0.05$ and $1-\beta=0.8$; performed with GPower 3.1.9.2.

Dye Leakage Assays are performed to test the effect of aggregated amylin on sarcolemmal integrity. The uptake of the fluorescent dyes Lucifer Yellow (MW=443 Da), Alexa-488 (MW=570 Da) and calcein (MW=623 Da) in cardiac myocytes using a scanning confocal microscope to determine whether the pores created by aggregated amylin are large enough to allow the passage of large molecules is measured.

Cryo-EM is used for ultrastructural analysis of cardiac myocytes, as before[7,83]. Briefly, myocytes are frozen rapidly and embedded in Eponate-12 resin. Blocks are cut into 70-nm-thick sections. Serial sections are collected on slot grids covered with a 50 nm Formvar support film and visualized on the EM.

Lipid peroxidation, is measured as previously described[8]. Sarcolemmal lipid peroxidation is measured using confocal microscope analysis of the fluorescent probe 4,4-difluoro-3a,4adiaza-s-indacene ($C_{11}$-BODIPY$^{581}/_5^{91}$, Invitrogen) in isolated cardiac myocyets. This probe is efficient for assessing the free radical-mediated oxidation that takes place in the lipophilic domain, while it does not detect aqueous radicals[88]. Formation of amylin-4HNE and amylin-MDA adducts in cardiac tissue is also measured using LC-MS/MS and Western blot, as before[8]. Myocyte ROS levels in HIP vs. WT rats are measured using fluorescent indicators CM-$H_2$DCFA ($H_2O_2$), as described previously[7,8].

EET Effect on Myocytes.

Pre-diabetic HIP rats that have lower RBC amylin and RBC deformability levels are used. Selected HIP rats will presumably have intact vascular endothelial cells. To increase their endogenous levels of EETs, HIP rats are treated with 1 ml drug/liter APAU sEH inhibitor (UC1153, from abcam) in drinking water for 10 weeks, as previously described[7,83]. Rats in each of the four EET treatment groups are intravenously infused with 10 mg/Kg EETs via tail vein, weekly, for 10 weeks. Control rats (matched for age and blood glucose, RBC amylin and RBC deformability levels) received the same amount of polyethylene glycol, a neutral biocompatible polymer (vehicle). Blood glucose and RBC characteristics (amylin, deformability and stickiness) are measured biweekly. At the end of treatment period, heart function is measured, followed by euthanasia and measurement of cardiac hypoxiamarkers, structural integrity and stability of capillaries and sarcolemmal processes.

Sub-Sarcolemmal Deposits.

Figure 12:
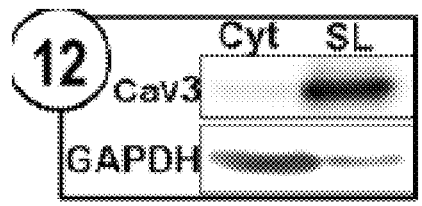
FIG. 12. shows Sarcolemmal and cytosolic fractions of myocytes.

To clarify whether aggregated amylin accumulates intracellularly, LC-MS/MS analysis of sarcolemmal vs. cytosolic amylin fractions was performed. To separate the sarcolemmal fraction, myocyte lysates are centrifuged at 1,000 g for 5 min to generate a postnuclear supernatant. This is then further centrifuged at 27,000 g for 35 min and the plasma membrane pellet is re-suspended in Laemmli buffer. This protocol results in efficient separation of sarcolemmal (SL) and soluble fractions (Cyt) (FIG. 12), i.e. the sarcolemmal protein Caveolin3 is found almost exclusively in the SL fraction while the cytosolic protein GAPDH is highly enriched in the soluble fraction. Specimens from each group are further analyzed by confocal microscopy to identify anatomical localization of amylin deposits. Sections are treated with formic acid to improve immunostaining. Serial sections 50 μm thick are incubated in biotinylated amylin antibody overnight at 25° C. For confocal microscopy, biotinylated amylin antibody is visualized using streptavidin conjugated Cy-3 fluorochrome. Confocal images are collected on an Olympus IX70 inverted microscope. For blocking tissue autofluorescence, slides are pre-incubated in 1% Sudan black solution for 1 h at room temperature. Control sections with either the primary or secondary antibodies omitted are used to test the antibody specificity.

Figure 13A:
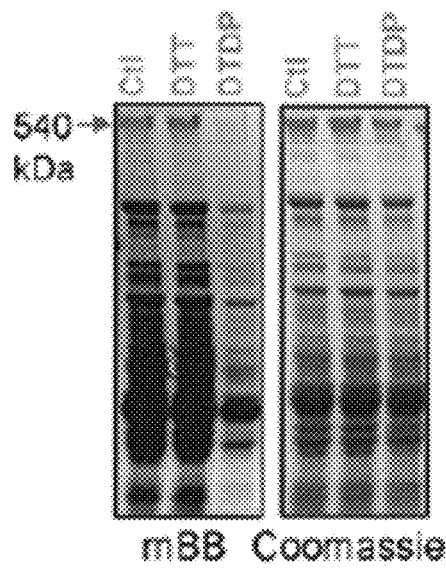
FIGS. 13A-13B. show increased RyR oxidation in WT and HIP hearts. 13A) Measurement of free thiols contained in RyRs. 13B) Percentage of RYR free thiols calculated from experiments as in panel A.
Figure 13B:
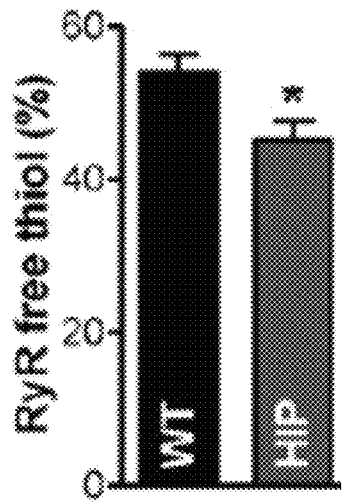

Since myocyte $Ca^{2+}$ dysregulation in diabetes involves RyR activation by post-translational modifications[81,82], RyR phosphorylation & O-GlcNAcylation using immunoblots and phospho-specific antibodies[25] is assessed while RyR oxidation is assessed with the monobrobimane method[87] as in FIG. 13.

Figure 14:
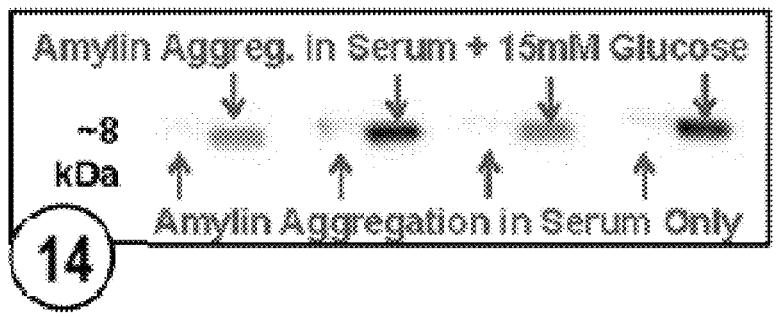
FIG. 14. shows Amylin aggregation in serum in the absence or presence of added glucose.

Glycated amylin is prone to faster aggregation[95], which is also suggested the data (FIG. 14). Hyperglycemia and hyperamylinemia together could further enhance accumulation of aggregated amylin in RBCs and the cardiovascular system. LC/MS/MS and Pro-Q Emerald glycoprotein gel stain kit (Molecular Probes) is used to measure glycated amylin and test whether hyperglycemia increases amylin aggregation, in vivo.

Results
Aggregated Amylin in Circulating RBCs in Humans.

Figures 2A, 2B, 2C:
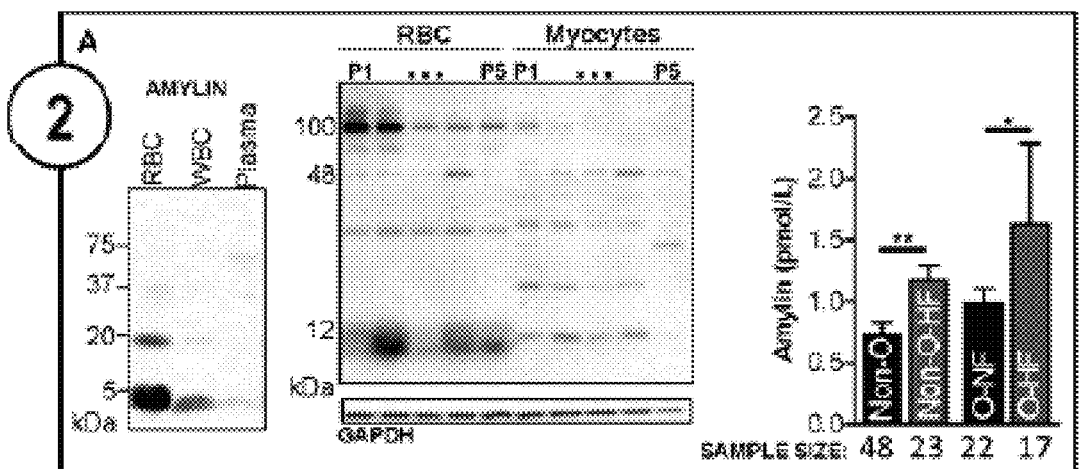
FIGS. 2A-2C. show analysis of amylin in matched plasma, Red Blood Cells, Myocytes, and White Blood Cells in humans presenting with obesity and/or heart failure or non-obese. 2A) Western blot analysis of amylin in matched plasma, white blood cells (WBCs) and red blood cells (RBCs) from a patient with obesity (BMI≥30) and HF. 2B) Comparative analysis in paired RBCs and cardiac myocytes from the same patients. 2C) The relationship between RBC amylin levels, obesity and HF.

Both monomeric amylin (3.9 kDa) and aggregated amylin are present in the blood of humans with obesity and HF, as previously reported[8]. Matched plasma, RBCs and white blood cells (WBCs) from the same patient showed multiple molecular weight bands positive for amylin (FIG. 2A) consistent with previous data[7] from HIP rats demonstrating that amylin forms detergent-insoluble amylin aggregates in the blood. The large molecular weight bands in FIG. 2A may also signify interactions of amylin with other blood proteins, lipids or circulating reactive aldehydes, as suggested by recent studies[18] of plasma from HIP rats. The amylin immunoreactivity signal in RBCs is greatly increased compared to plasma and WBCs. Paired RBCs and cardiac myocytes from the same patients have almost identical size distribution of incorporated amylin (FIG. 2B), suggesting a mechanism of cardiac amylin accumulation based on pre-formed aggregated amylin secreted in the blood from pancreatic islets. A study was performed to determine a possible association between diabetic HF and elevated RBC amylin levels. n=110 RBC specimens and medical record data stored at the University of Kentucky Center for Clinical and Translational Science (UK-CCTS) were tested. Patients in the HF group suffered with idiopathic dilated cardiomyopathy. RBC samples were provided by individuals with obesity (BMI~30) and HF (O—HF; n=17), obesity without HF (O—NF; n=22), no obesity (BMI<30) with HF (Non-O—HF; n=23) and no obesity, no HF (controls; Non-O; n=48). The results (FIG. 2D) indicate that HF correlated with increased levels of amylin in RBCs. Compared to BMI<30, a BMI~30 appears also to increase the RBC amylin level.

Figure 3A:
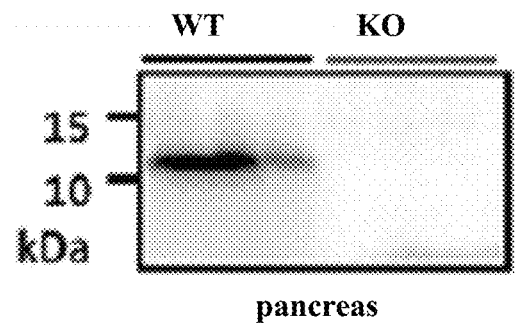
FIGS. 3A-3C. show characterization of AKO rats, 3A) amylin expression, glucose homeostatis, and body weight. Demonstration of lack of amylin expression in AKO rats. 3B) Deletion of amylin gene (AKO rats) reduced the difference in glucose homeostasis between male and female rats. 3C) Body weight in AKO vs. WT rats.
Figure 3B:
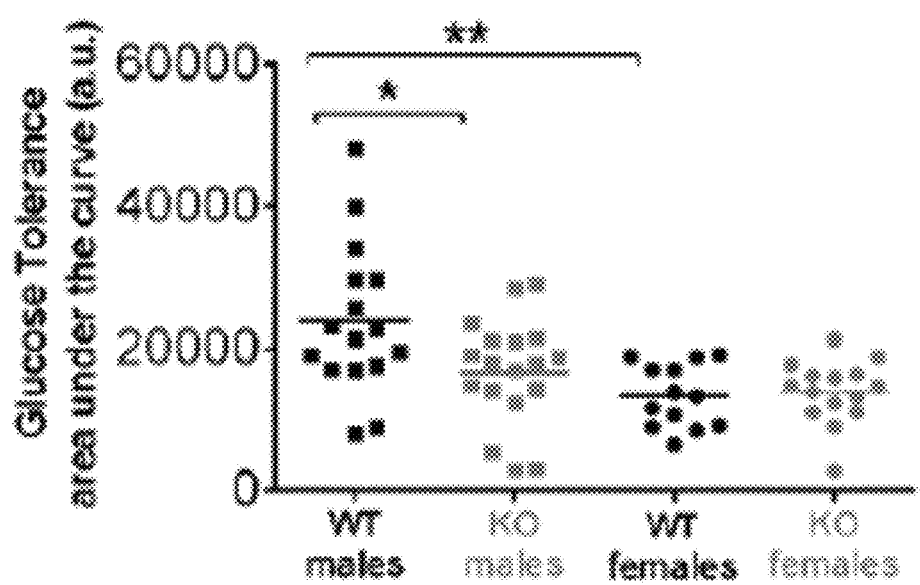
Figure 3C:
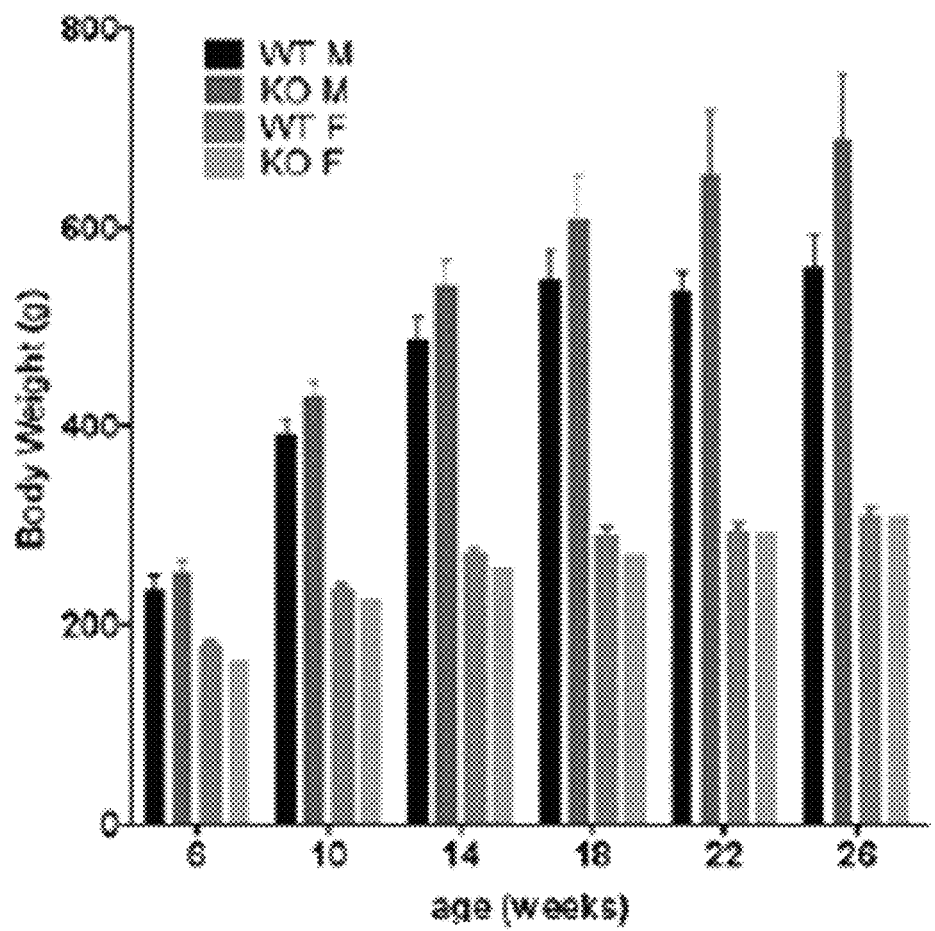

Western blot on pancreas homogenates demonstrates lack of amylin immunoreactivity signal in AKO rats (FIG. 3A). Deletion of amylin gene reduced the difference in the blood glucose elimination between male and female rats (FIG. 3B), consistent with data[86] reported in amylin knockout mice. Intriguingly, the increased insulin responses are associated with weight gain in male AKO vs. WT rats, whereas females appear unaffected (FIG. 3C).

Circulating RBCs Accumulate Aggregated Amylin.

The RBC amylin level in HIP rats increased with the pathological progression from normal to pre-diabetic and to diabetic states, as shown by flow cytometry data (FIG. 4A), ELISA (FIG. 4B) and Western blot (FIG. 4C). Compared to WT rats, which have RBCs with normal biconcave disc shapes, the RBCs from HIP rats have rounded shapes (FIG. 4D) and decreased hemoglobin (Hb) levels (FIG. 4E). This structural change of RBCs was replicated by the incubation of WT rat RBCs with recombinant human amylin (50 μmol/L; 2 h; FIG. 4F).

Figure 5A:
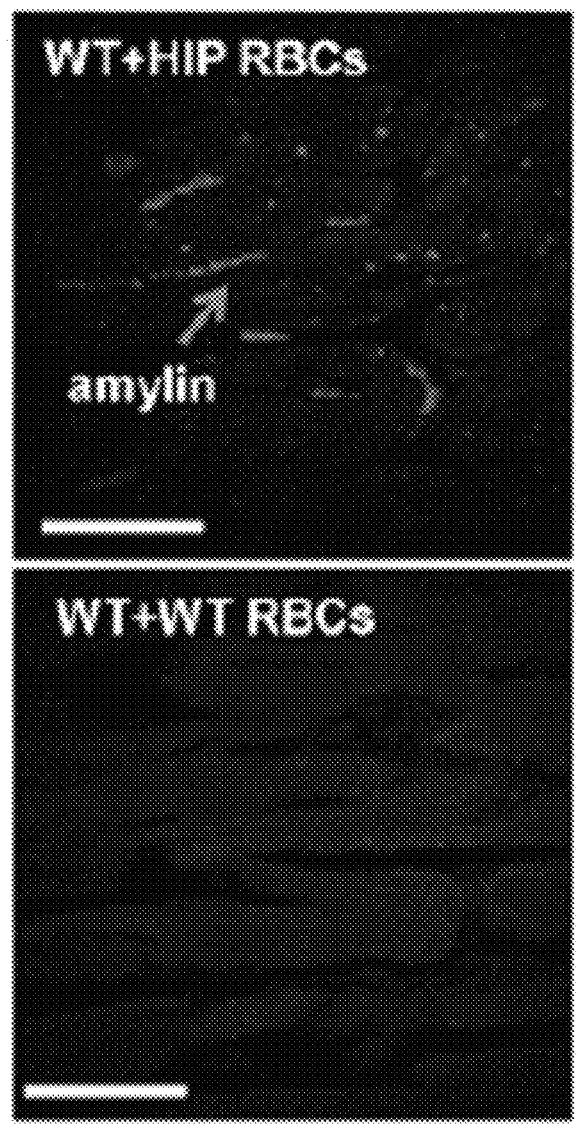
FIGS. 5A-5C. show characterization of amylin in cardiac tissue of rats. 5A) Confocal microscopy analysis of amylin in cardiac tissue from WT rats infused with HIP rat RBCs v. WT rat RBCs. 5B) Immunostaining for amylin, glycophorin A (a protein abundant in RBCs) and collagen IV in cardiac tissue isolated from AKO rats injected with HIP rat RBCs. Scale bar, 20 μm. 5C) Adhesion to cultured endothelial cells was compared for RBCs from HIP v WT rats and for RBCs from WT rats±incubation with human amylin (50 μM) for 2 hours.
Figure 5B:
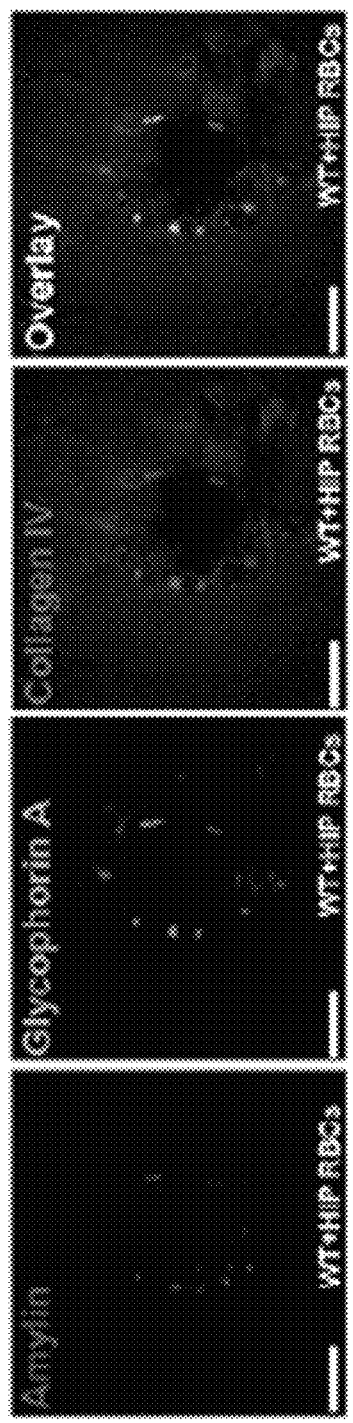
Figure 5C:
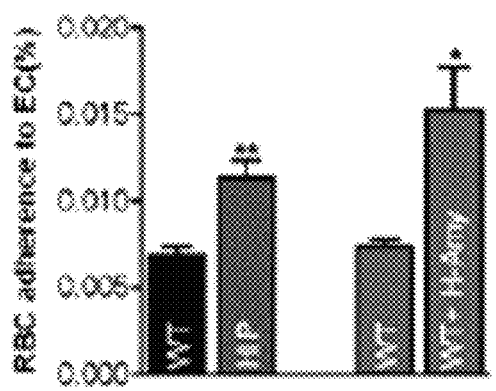

Aggregated Amylin Changes the Interaction of RBCs with Vascular Endothelium, as suggested by data (FIG. 5) from WT rats infused with RBCs collected from diabetic HIP rats (300 μL, daily, for seven days, q.d., via tail vein). Confocal microscopy analysis showed areas of occluded capillaries, indicating the attachment of HIP rat RBCs to endothelium (FIG. 5A). In contrast, cardiac tissue from WT rats infused with WT rat RBCs showed intact myocardial capillaries. Immuno-staining cardiac tissues for amylin (green), collagen IV (red) and glycophorin A, a RBC specific protein (blue) showed that amylin and glycophorin A are co-localized with collagen IV (FIG. 5B, overlay), indicating that amylin-loaded RBCs stuck to the vascular wall. Consistent with these results, RBCs from HIP rats have increased adherence to cultured endothelial cells (FIG. 5C). Incubation of RBCs from WT rats with recombinant human amylin (50 μmol/L; 2 h) also increased the RBC adherence to cultured endothelial cells (FIG. 5C).

The plasma levels of erythropoietin (EPO), a glycoprotein cytokine secreted by kidneys in response to cellular hypoxia[73], are greatly increased in HIP rats showing high RBC amylin levels (~16 mo old), compared to age-matched WT rats (FIG. 6). In contrast, HIP rats in the normal state (6 mo old) and age-matched WT rats have similar plasma EPO levels (FIG. 6).

Figure 9E:
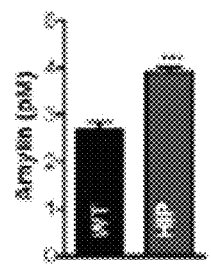

Amylin deposition in capillaries and RBCs damages capillary endothelium, enabling infiltration of aggregated amylin into myocardial interstices and injury of myocyte sarcolemma. Myocardial tissues from HIP rats showed abundant haemosiderin deposits (FIG. 9A) indicating microhemorrhages, which is consistent with previous findings in HIP rat brains. Infusion of RBCs from HIP rats into normal WT rats provoked sporadic myocardial microhemorrhages (FIG. 9B). In contrast, WT rats infused with WT rat RBCs showed no microhemorrhages (FIG. 9C). In HIP rats, microhemorrhages were found in association with mild edema (FIG. 9A; arrow), suggesting altered tight junctions. Indeed, the levels of tight junction proteins (claudin, occludin and ZO-1) were lower in myocardial capillaries from HIP rats compared to WT littermates (FIG. 9D), which correlated with amylin accumulation in capillaries (FIG. 9E).

Figure 10A:
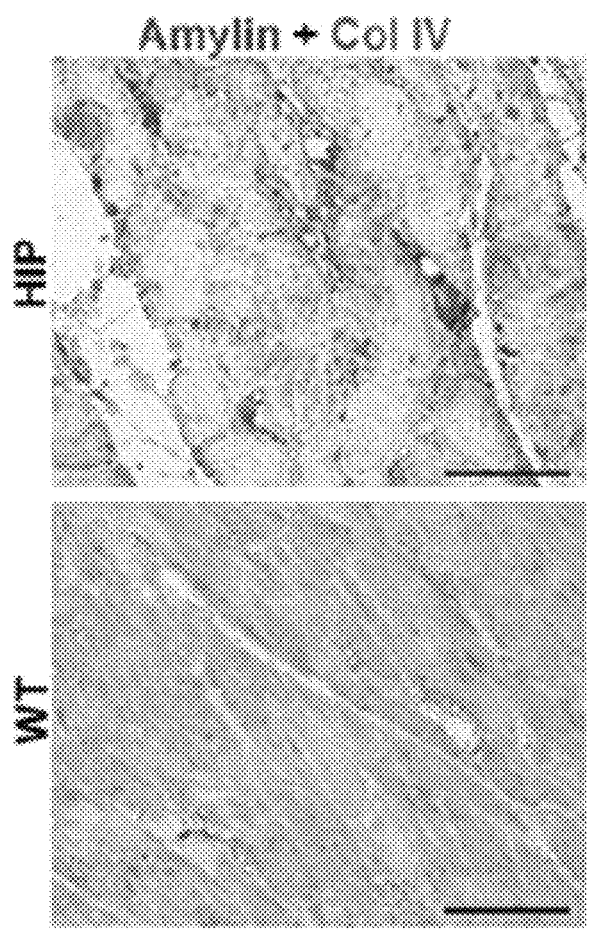
FIGS. 10A-10C. show structural integrity and stability of myocardial cells. 10A) Co-staining for amylin and collagen IV in a 15 mo old HIP rat v. age matched WT rat. Same as in above form amylin and IBA-1, in 10B) and for endothelial cells, in 10C. Scale bar, 20 μm in 10A); 100 μm in (10B&10C).
Figure 10B:
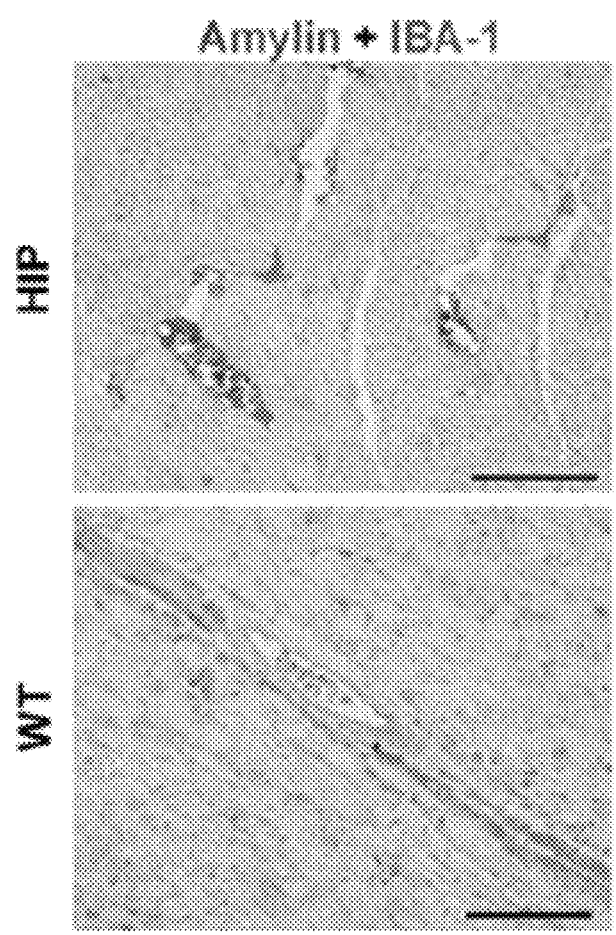
Figure 10C:
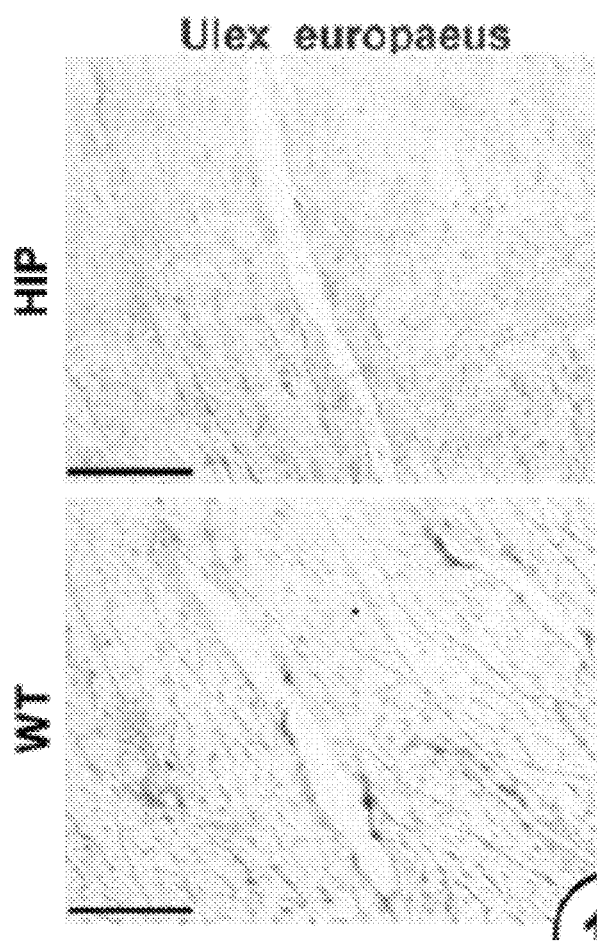

Co-staining for amylin and collagen IV, a component of the basement membrane structure, showed that amylin (brown) is co-localized with collagen (green) in small blood vessels (presumable capillaries and arterioles; FIG. 10A). Collagen was replaced with amylin deposits in capillary beds, which correlated with dilation of capillaries, increased separation of the myocytes and myocyte disarray. Co-staining for amylin and the ionized calcium-binding adapter molecule 1 (IBA1), a marker of macrophage activation, indicated abundant intravascular accumulation of macrophages in HIP rat hearts (FIG. 10B). Macrophages (green) are seen in areas of amylin deposition (brown) suggesting endothelial injury and a potential role of macrophages in the clearance of aggregated amylin from blood vessels. Myocardial capillaries appeared depleted of mural cell coverage in HIP vs. WT rats (immunostaining for ulex europaeus, FIG. 10C). In contrast, no microhemorrhages, amylin deposition, macrophage accumulation and endothelial cell loss are seen in myocardial tissues from WT littermate rats (FIGS. 9 & 10).

Figure 11A:
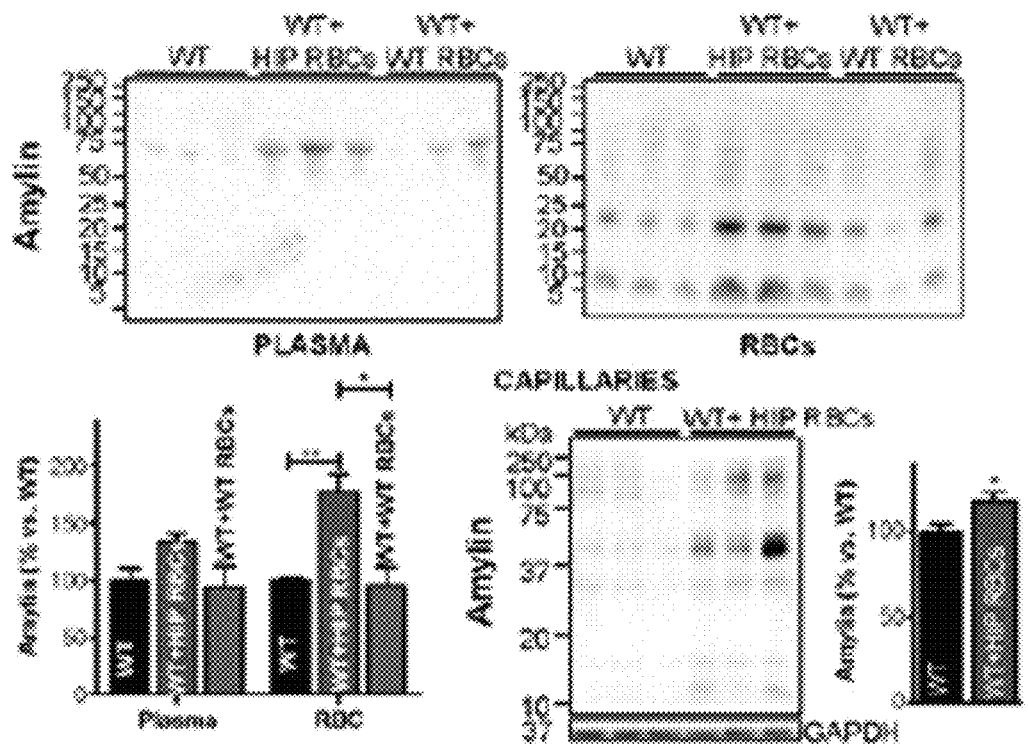
FIGS. 11A-11C. show infusion of WT or HIP rats with WT or HIP rat RBCs and detection of amylin in cells and tissues. 11A) Western blow analysis of amylin in plasma, RBC lysates and myocardial capillaries from WT rats infused with HIP rat RBCs v. WT rat RBCs 11B) Co-staiing for amylin (brown) and collagen (green) in cardiac tissues from WT rats infused with HIP rat RBCs v. WT rat RBCs. 11C) same as in above for amylin (brown) and IBA-1 (green). Scale bar, 20 μm.
Figure 11B:
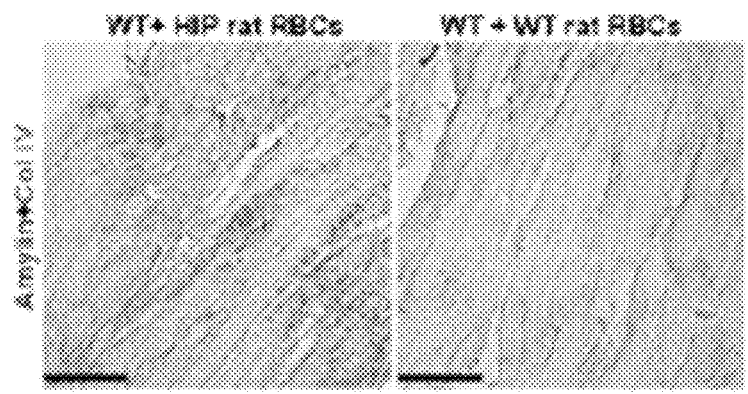
Figure 11C:
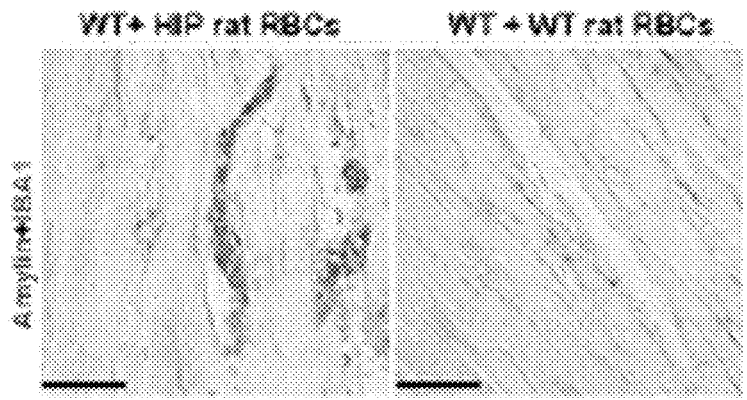

Amylin levels in plasma, RBCs and myocardial capillary lysates from WT rats infused with HIP rat RBCs are elevated compared to WT rats infused with WT rat RBCs (FIG. 11A). The presence of amylin deposition in myocardial microvessels from WT rats infused with HIP rat RBCs was confirmed by immunohistochemistry with an amylin antibody (brown; FIG. 11B). In cardiac tissues from WT rats infused with HIP rat RBCs, co-staining for amylin and IBA1 indicated intravascular macrophage activation (FIG. 11C). In contrast, infusion of WT rats with similar amounts of WT rat RBCs showed no effect on blood amylin level and capillary structure.

Figure 15A:
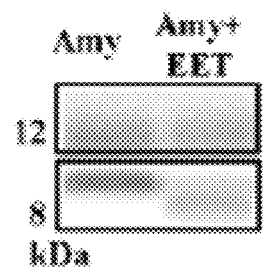
FIGS. 15A-15B. show effect of 14, 15-EET on amylin aggregation in myocytes.
Figure 15B:
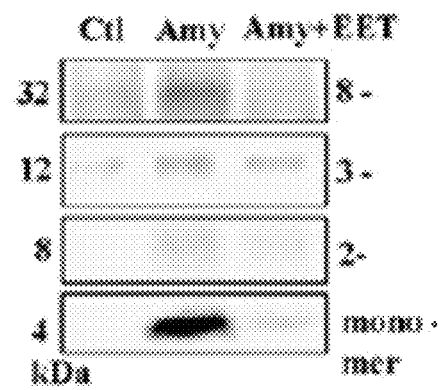

The 14,15-EET isomer reduced amylin aggregation (FIG. 15A) and amylin incorporation in cardiac myocytes (FIG. 15B) ex vivo.

Figure 16A:
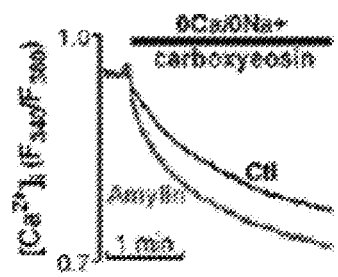
FIGS. 16A-16C. show effect of membrane sealant P188 on amylin-induced increase in sarcolemmal $Ca^{2+}$ leak (16A-16B) and $Ca^{2+}$ transient amplitude (16C).
Figure 16B:
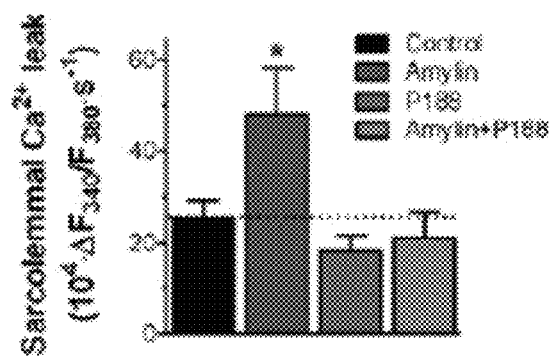
Figure 16C:
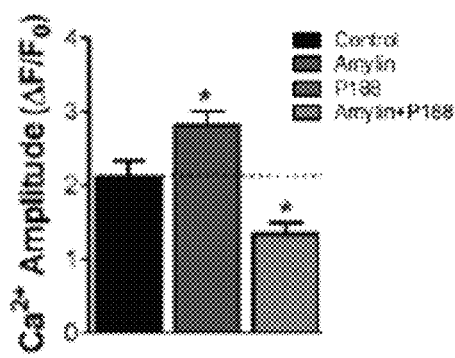
Figure 17:
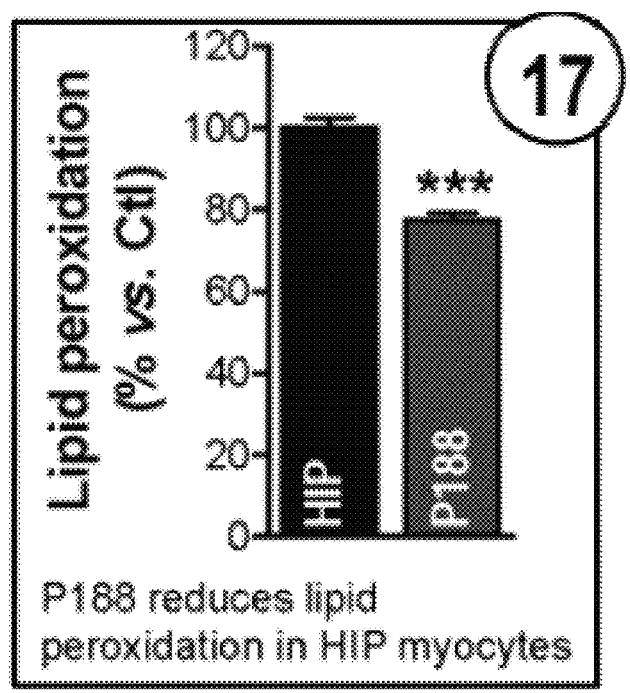
FIG. 17. shows the effect of P188 on lipid peroxidation in HIP rat myocytes.

The use of membrane sealants, such as poloxamer 188 (P188), prevented cardiac injury and ventricular dilation in dystrophic mice[84] and dogs[68]. A single intravenous P188 bolus significantly reduced membrane damage and improved compound muscle action potential in a rat model of membrane injury, as previously reported[67]. P188 prevents the increase in sarcolemmal $Ca^{2+}$ leak and the $[Ca^{2+}]$ increase in myocytes incubated with aggregated amylin (FIG. 16), consistent with previous data reported for Aβ in neurons[85]. Acute exposure to P188 (2 h) also reduced lipid peroxidation in myocytes isolated from diabetic HIP rats (FIG. 17).

Discussion

These data suggest the following: i) circulating RBCs take up and concentrate aggregated amylin, ii) amylin-loaded RBCs have lower Hb levels, iii) the RBC amylin level increases with the progression of diabetes, and iv) compared to normal RBCs, amylin-loaded RBCs have anomalous stiffness and stickiness, jamming the capillaries. Thus, elevated blood levels of aggregated amylin and subsequent amylin deposition in RBCs may provoke cardiac hypoxia by impairing RBC deformability, reducing the Hb content in RBCs and slowing the RBC move through the capillaries.

ADDITIONAL or ALTERNATIVE MATERIALS & METHODS

Human Studies

In some embodiments, this research employed de-identified blood specimens matched with medical record data obtained from the biobank of the Center for Clinical and Translational Science at University of Kentucky (UK-CCTS). Sample collection and storage was approved by the Institutional Review Board at the University of Kentucky. Written informed

| | n = 353 | |
|---|---|---|
| Sample size | Disease (n = 287) | Healthy (n = 66) |
| Age | 55 ± 1 years | 43 ± 2 years |
| Female sex | 127(45%) | 29(45%) |
| Obesity (BMI >30) | 116(41%) | 14(21%) |
| Heart Failure | 108(38%) | |
| Type-2 Diabetes | 69(24%) | |
| Cancer | 91(32%) | |
| Stroke | 13(5%) | |
| Type-1 Diabetes | 5(2%) | | consent was received from each individual prior to donating the blood sample. Specimens from transplant recipients (less than 6 months from the transplant), patients with liver disease, patients with HIV and pregnant or lactating women, which may affect the pancreatic secretion of amylin, were excluded from the study. RBCs from patients with type-2 diabetes were the amylin positive control, whereas patients with over 15 years of type-1 diabetes (and, therefore, depleted (3-cell mass) but otherwise healthy served as the negative control for amylin. The latter samples were collected under a different IRB-approved protocol and de-identified.

Table 2. Characteristics of the individuals providing the RBC samples, including age, sex, body mass index (BMI), diabetes status and co-morbidities.

RBC specimens were divided into groups based on the primary diagnosis of heart failure, cancer or stroke. Most individuals in the disease group had type-2 diabetes as the second diagnosis. Diabetes status, co-morbidities and characteristics of the individuals providing the blood samples, such as age, sex and body mass index (BMI) are summarized in Table 2. The control group represents individuals without diabetes, heart failure, stroke or cancer.

Statistics and defining and handling of outliers for the human study

For some analyses, the homogeneity of variance was tested using Levene's test. Equal variance was assumed when P>0.05 and normal t-test (parametric test) was applied. When ANOVA assumptions were violated, Mann-Whitney test (non-parametric test) was applied. Correlation estimates with scatterplots were used to examine the relationship between RBC amylin levels and HbA1c (FIGS. 18 d-j), respectively, in healthy individuals and disease groups. All analyses were performed using GraphPad Prism 5.0 software.

A Whisker plot was computed (FIG. 18c) from amylin levels in human RBC across different groups. In each group, the median, first and third quartiles were calculated. The interquartile range was calculated by subtracting the lower quartile value from the upper quartile value. Points falling more than 1.5 times the interquartile range above the third quartile were considered outliers. The outliers were indicated in the FIG. 18 caption and included in statistical analyses.

Experimental Animals

Figure 24:
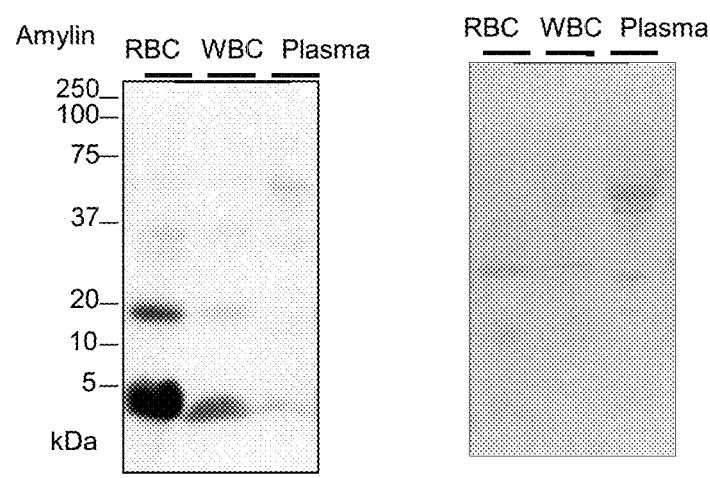
FIG. 24 shows Representative western blot analysis (Left) of high molecular weight amylin oligomers in plasma, RBC lysate and white blood cell (WBC) lysate from an individual with type-2 diabetes. (Right) The Ponceau S staining of the blot show in Left panel.
Figure 25:
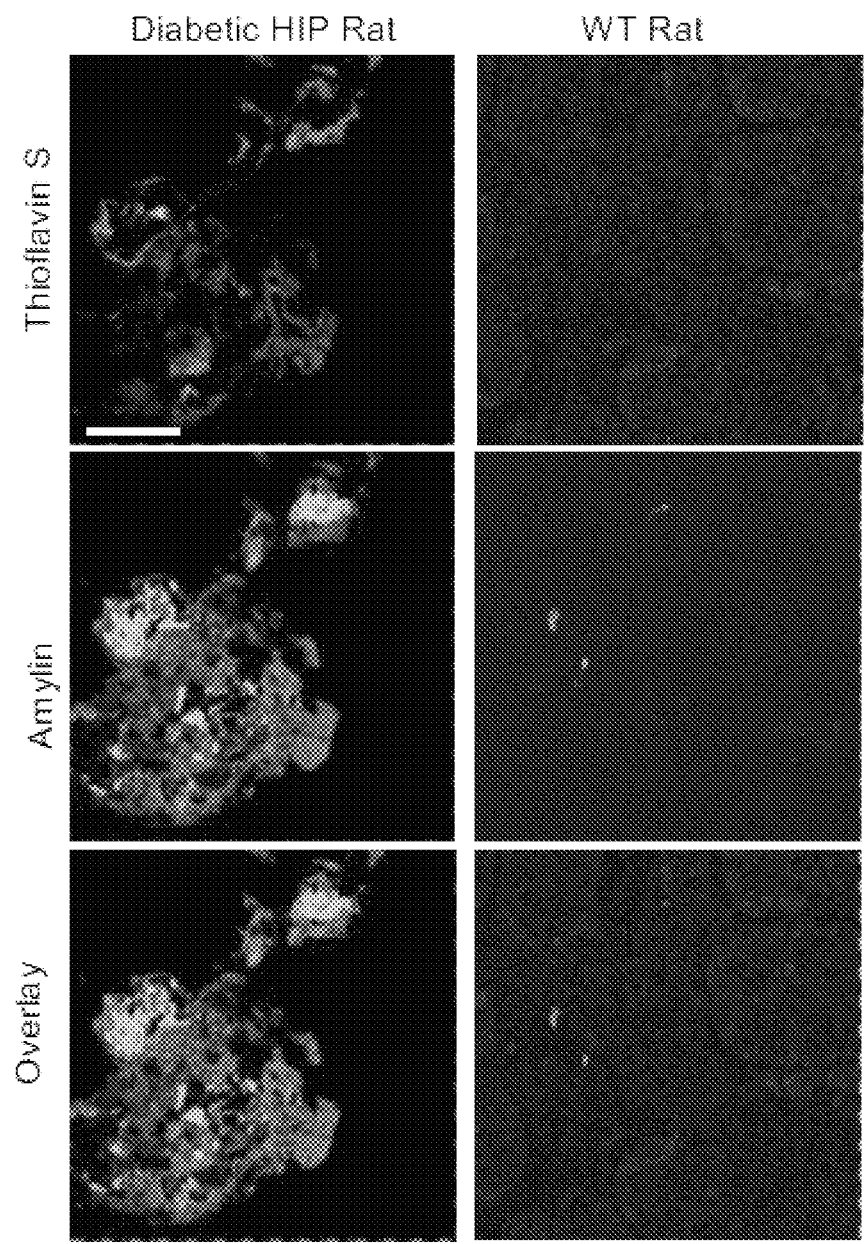
FIG. 25 shows representative images of Thioflavin S (green) and amylin (red) staining in the pancreas from a diabetic HIP and a control WT rat (n=3/group). Scale bar, 30 μm.

All animal experiments were approved by the Institutional Animal Care and Use Committee at University of Kentucky and conforms to the Guide for the Care and Use of Laboratory Animals, the 8th Edition, published by the National Academies Press, Washington (DC); 2011. Rats that develop type-2 diabetes (T2D) linked to expression of human amylin in the pancreas (HIP rats; n=62) were compared with rats that develop T2D in the absence of amyloid, as they express solely the non-amyloid forming rat amylin (UCD rats; n=37)

and control, non-diabetic rats (WT rats; n=50). Only males were used because HIP females become diabetic at a more advanced age. (FIGS. 24-25)

HIP rats are Sprague-Dawley (SD) rats that overexpress (3-fold) human amylin specifically in the pancreatic f3-cells on the insulin II promoter. (FIG. 24) HIP rats develop amylin dyshomeostasis and amylin amyloid deposition in pancreatic islets leading to f3-cell apoptosis and hyperglycemia with regular diet. Breeding pairs were obtained from Charles River Laboratory. The presence of the human amylin gene was confirmed by standard PCR techniques to detect Rip1 and Mus-a-actin. Actin was used as the internal control. WT littermates were used as the non-diabetic control.

UCD rats were generated as described in Ref 106 by crossing obese Sprague-Dawley rats with Zucker diabetic fatty (ZDF) lean rats. ZDF-lean founder rats were purchased from Charles River Laboratories. These rats have functional leptin receptors and the autosomal recessive f3-cell defect. (FIG. 26) The breeding strategy was to maintain the obese phenotype from obese Sprague-Dawley rats and selecting for individuals homozygous for the autosomal recessive f3-cell defect. In the seventh generation (F7) all animals were homozygous for the f3-cell defect and increased genetic propensity to develop diabetes.

Rats were housed (singly) in individually ventilated cages (ACE, Allentown, NJ) with Sani-Chip bedding (Harlan-Teklad) and maintained on a standard chow diet (Teklad Global 18% Protein Rodent Diet #2018) and reverse osmosis drinking water for the duration of the study. Nesting material (Enviro-Dri®, Shepherd Specialty Papers) and aspen chew blocks (Lomir Biomedical Inc.) were provided for environmental enrichment. All animals were maintained on a 12:12 hour light:dark cycle at temperatures between 21-24° C.

Treatment

Figure 27:
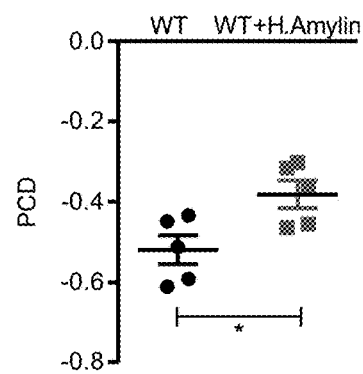
FIG. 27 shows PCD for WT rat RBCs and WT rat RBCs incubated ex vivo with oligomerized human amylin (n=5 preparations/group).

A retrospective analysis was performed of kidney tissue from HIP rats with pharmacologically elevated EETs used in a prior study. (FIG. 27). Briefly, pre-diabetic male HIP rats were randomized to treatment (HIP-T) and no treatment (HIP-UT) groups by a blinded observer. To increase the endogenous levels of EETs, pre-diabetic HIP rats were treated with 1 ml drug/L of the soluble epoxide hydrolase inhibitor APAU (UC1153) added in drinking water for 10 weeks. The treatment resulted in lower levels of aggregated amylin in blood and cardiac myocytes and improved heart function.

Renal Function Analysis

Rats were placed in metabolic cages. After 2 days of acclimation, 24-hours cycle urine collections were taken at baseline and day 2. Blood sampling (500 µl) was obtained from tail vein for determination of creatinine level. Creatinine concentration in plasma and urine was measured using the kinetic Jaffé method (FIGS. 28A-C) with 10% picric acid solution in NaOH. After 15 min, absorbance reading was obtained in a microplate set for dual wavelengths at 490 nm (read) and 620 nm (reference). Creatinine clearance (Ccr) was calculated using the following formula: Ccr (ml/min)= (urine creatinine/plasma creatinine)×urine flow rate. Urinary excretion rate of albumin was measured using a commercially available ELISA kit (E110-125, Bethil Laboratories, Inc, TX).

Tissue Extraction and RBC Isolation

For measurements of hypoxia markers (HIF-1$\alpha$, HIF-2$\alpha$, Arginase 1, Arginase 2 and vHL) by ELISA and arginase activity assay, tissues were extracted in 1×PBS with 1% (v/v) protease and phosphatase inhibitors. The homogenate was frozen at −80° C. and thawed on ice for 3 consecutive cycles to break cell membranes. For other biochemical assays, tissues were extracted in homogenization buffer (150 mM NaCl, 50 mM Tris, 50 mM NaF, 2% Triton X-100, 0.1% SDS and 1% (v/v) protease and phosphatase inhibitors). All homogenates were then centrifuged at 17,000×g for 30 minutes at 4° C.

In some embodiments, rat blood samples were collected into sterile K2-EDTA vacutainer tubes. RBCs were isolated from plasma by centrifugation at 1,000×g for 10 minutes, at 4° C., immediately after blood collection. To obtain RBCs lysates for biochemical analyses, RBCs were incubated with cell lysate buffer (10% NP-40, 150 mM NaCl, 10 mM Tris, 2 mM EGTA and 50 mM NaF, 1% (v/v) protease and phosphatase inhibitors) for 30 minutes on the rotor at 40 C, followed by centrifugation at 17000×g for 30 minutes at 4° C. Supernatant was used for experiments.

RBC Transfusion

In some embodiments, RBCs were isolated into a heparin lithium tube, washed twice with sterile 1×PBS, combined with storage solution (150 mM HCl, 45 mM dextrose, 45.5 mM mannitol, and 2.2 mM adenine) in a 3:1 v/v ratio, transferred to sterile tubes and stored at 4° C. in the dark before injection. Rats received 300 µL of pre-warmed (at 37° C.) RBCs solution once daily for 7 days via tail vein injection.

Hematocrit and Hemoglobin Measurements

In some embodiments, the ratio of RBCs to total blood volume (hematocrit; Hct) was measured with an i-SATA analyzer (VetScan i-STAT 1 Handheld Analyzer, ABAXIS) using i-STAT CG8+ cartridges (VetScan i-SATA CG8+ cartridge, ABAXIS, Cat #600-9001-25) according to the manufacturer's protocol.

In some embodiments, isolated RBCs were first suspended to a hematocrit 2.5% in Hank's Balanced Salt Solution (HBSS) containing 0.5% BSA (HBSS/A). 10 µL of RBCs suspension was further diluted in 990 µL HBSS/A and 100 µL of this RBCs dilution was incubated with 200 µL 0.5% SDS for 5 hours. Total hemoglobin in the 100 µL RBCs diluted suspension was calculated from the optical density (at 405 nm) measured with a spectrophotometer (Molecular Devices, Menlo Park, CA).

Assessment of RBC Shape and Amylin Deposition on RBCs by Flow Cytometry

In some embodiments, RBCs (1×107 cells) were aliquoted to assay tubes, washed twice with 2 mL incubation buffer (0.5% BSA in PBS), and resuspended in 100 µL incubation buffer. RBCs were incubated with an anti-amylin antibody (1:200, T-4157, Bachem-Peninsula Laboratories, CA) for 1 hour on ice, washed twice with PBS by centrifugation at 1000×g for 1 minute and then incubated with goat anti-rabbit Alexa Fluor® 488 (A11029, Invitrogen, MA) for 30 min on ice. RBCs were then washed twice before re-suspension in 200 µl PBS, and analyzed by flow cytometer (Becton Dickinson LSRII) within 90 min. To assess the cell shape, RBCs were first gated on a forward scatter (FSC)/side scatter (SSC) plot. The R1 events arevisualized using a FSC-A/FSC-H dot plot. For detecting amylin deposited on RBCs, the cells were first gated on a forward scatter (FSC)/side scatter (SSC) plot. RBCs were further gated to determine the amylin signal (Alexa 488), using negative control (no antibody) and positive control to set the upper and lower boundaries.

RBC Adhesion Assay

In some embodiments, adult rat microvascular endothelial cells (RA-6024, Cell Biologics, IL) were cultured on 96-wells cell culture plate coated with cell attachment factor solution (123-100, Sigma, MO). Cells were allowed to attach for 24 hours and used for experiments when they reached 70%-90% confluency. Isolated RBCs were washed twice with cold HBSS and once with HBSS/A. RBCs were suspended to hematocrit 2.5% in HBSS/A. 10μL, of RBCs suspension was used to measure the hemoglobin content as described above. Another 300μL of RBC suspension aliquot (hematocrit 2.5% in HBSS/A) was gently layered on confluent endothelial cells pre-incubated with 150 μL of media containing different concentrations of (±)14(15)-EET (50651, Cayman Chemical, MI). The plate was incubated at 37° C. for 40 min. An additional 83 μL of HBSS/A was gently added to create a slight convex meniscus over each well, and the plate was covered with an adhesive plastic film (89087-692, VWR, IL). The plate was then inverted and allowed to sit for an additional 30 min at 37° C. With the plate maintained in the inverted position, the adhesive sheet was removed and the remaining fluid was removed by aspiration. 200 μL 0.5% SDS was added to each well, followed by 5 hours incubation at room temperature. The amount of hemoglobin in each well was measured from the optical density (OD) as described above. Adherence was calculated as the percentage of OD of adhered hemoglobin/(OD of total hemoglobin×dilution factor).

Immunofluorescence

In some embodiments, isolated RBCs were incubated with primary antibodies against human amylin and Glycophorin A, followed by incubation secondary antibodies, and imaged with a Nikon A1R confocal microscope. For hemoglobin staining, blood smears on glass slide were fixed and incubated with primary antibodies against hemoglobin and human amylin. Smears were then incubated with secondary antibodies, mounted in mounting media and imaged.

Biochemical Assays

In some embodiments, ELISA assays for human amylin, erythropoietin, HIF1-α, HIF2-α, arginase 1, arginase 2 and vHL were performed according to the manufacturer's protocols. Arginase activity was measured in kidney homogenates using a colorimetric assay. Western blots were performed on plasma, WBC lysates, and RBC lysates from humans using a primary antibody against amylin.

Immunohistochemistry

In some embodiments, isolated RBCs were washed 3 times with 1×PBS, blocked with 10% goat serum for 15 minutes at 37° C., incubated with primary antibodies against human amylin (1:200, T-4157, Bachem-Peninsula Laboratories, CA) and Glycophorin A (1:100, sc-71159, Santa Cruz Biotechnology, TX) for 15 min at 37° C., followed by incubation with anti-mouse IgG and anti-rabbit IgG secondary antibodies for 15 min at 37° C. Cells were hemolyzed in 1% saponin in PBS, centrifuged at 8000 g for 5 min and the pellet was re-suspended in 1×PBS for microscopy. Images were obtained on a Nikon A1R confocal microscope (Nikon).

For hemoglobin staining, blood smears on glass slide were fixed in acetone/ethanol/methanol (6:2:2) for 20 minutes at RT. Smears were air-dried and re-hydrated in 1×PBS for 5 minutes, rinsed briefly in distilled water, and incubated with pre warmed (37° C.) trypsin solution (0.1% in calcium chloride 0.1% pH 7.8) for 15 minutes in humidity chamber. Next, smears were washed in PBS for 5 minutes with gentle agitation, rinsed in distilled water and air dried. Smears were then incubated at 37° C. with primary antibodies against hemoglobin (1:100, ab92492, Abcam) and human amylin (1:100, SC-377530, Santa Cruz Biotech) in humidity chamber for 30-40 minutes. They were next washed, air-dried and covered with anti-mouse IgG and anti-rabbit IgG secondary antibodies for 20-30 minutes at 37° C. After incubation smears were washed with PBS, rinsed in water, air dried and mounted in mounting media.

These sections of paraffin embedded pancreatic tissues were co-stained with Thioflavin S and an anti-amylin antibody.

Enzyme-Linked Immunosorbent Assay (ELISA)

ELISA assays for human amylin (EZHA-52K, Millipore, MA; EIA-AMY-5, Raybiotech, GA), erythropoietin (EPO; 442807, Biolegend, CA), hypoxia-inducible transcription factor 1α (HIF1-α; MBS764727, MyBioSource, CA), hypoxia-inducible transcription factor 2α (HIF2-α; MBS2601406, MyBioSource, CA), arginase 1 (MBS289817, MyBioSource, CA), arginase 2 (MBS7216305, MyBioSource, CA), and von Hippel-Lindau (vHL; MBS288882, MyBioSource, CA) were performed according to the manufacturer's protocols.

Arginase Activity Assay

Arginase activity was measured in kidney homogenates using a colorimetric assay (MAK112, Sigma, MO). To eliminate urine from kidney samples, 3004, of kidney homogenate were filtered through a 10 kD spin column (88513, ThermoFisher, MA) with centrifugation at 15000 g for 60 min, 4° C. Collected remnant was used for experiments. Assay was performed according to the manufacturer's protocol. Briefly, filtered kidney samples were incubated with reaction substrate mix for 2 hours at 37° C. The stop solution was applied, followed by incubation at 37° C. for 35 min. Absorbance reading was taken at 430 nm. Arginase activity was calculated based on manufacturer's analysis instruction.

Immunoblot

Western blot analysis was performed on plasma, WBC lysates, and RBC lysates from humans using a primary antibody against amylin (1:2,000, T-4157, Bachem-Peninsula Laboratories, CA).

Immunohistochemistry

Immunohistochemical staining was performed on rat kidney slices using antibodies against amylin (1:200, SC-377530, Santa Cruz, TX), collagen IV (1:1000, ab6586, Abcam, MA), IBA-1(1:200, 019¬19741, Wako, Va.), and ED1 (1:100, MCA341GA, Biorad, PA). Biotinylated anti-mouse (1:400, BA2000, Vector lab, CA), AP conjugated anti-mouse and anti-rabbit IgG (1:50, A3562, A3687, Sigma, MO) were the secondary antibodies. The staining area for amylin was analyzed by ImageJ. The imaging area is 1280×1024 pixels; 1 pixel2 is 0.053 μm2 for 40× objective lens.

Statistical Analysis

Statistical differences between groups were determined using student's t-test, one-way ANOVA or two-way ANOVA, as appropriate. Data are presented as mean±standard error. Differences between groups were considered significant when P<0.05. For human data, the homogeneity of variance was tested using Levene's test. Equal variance was assumed when P>0.05 and normal t-test (parametric test) was applied. When ANOVA assumptions were violated, Mann-Whitney test (non-parametric test) was applied.

Generated Antibody Immunohistochemistry

Thin sections of paraffin-embedded tissues were incubated with purified amylin and Aβ primary antibodies. After washings, sections were incubated with HRP-conjugated anti-rabbit IgG secondary antibodies. The sections were then stained with AEC chromogen, mounted and imaged with Nikon light microscope. HIP rat pancreas was used as a positive control while AKO rat pancreas was used as negative control.

Generated Antibody Western Blot

For western blot, brain tissue was homogenized in homogenization buffer with protease and phosphatase inhibitor cocktail. Brain and Pancreas lysate were generated by centrifugation (12,000×g) of brain homogenate and collection of the supernatant fraction. After electrophoresis, blotting, and blocking, membranes were incubated with primary antibodies for amylin and Abeta. The specific staining of protein bands were verified by comparing the bands with commercially available antibody on same samples.

Generated Antibody ELISA 96 well plates were coated with Amylin or Aβ or samples in bicarbonate buffer (pH 9.6) overnight at 4° C. After three washes with PBST (Tween 0.05%) plates were blocked with 300 μl of blocking solution followed by three more washes. Then plates were incubated with 100 μl of detection antibody (Aβ or Amylin) for 1 hour at room temperature. Again plates were washed three times followed by incubation with 100 μl of secondary antibody. After washing three times with PBST plates were incubated with TMB substrate. After getting signal reaction was stopped by 50 μl of stop solution and read at 450 nm. The signal in HIP rat pancreas which was used as a positive control while AKO rat pancreas as negative control.

Results

Example 1: Humans with Type-2 Diabetes have Amylin Deposition in RBCs

Figure 18A:
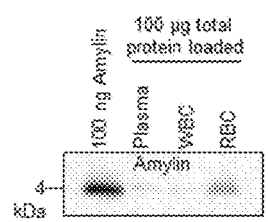
FIGS. 18A-18I show amylin-coated RBCs in human pathology. (18a) Representative Western blots showing the amylin monomer in matched plasma, RBC and white blood cell (WBC) lysates from an individual with type-2 diabetes. Recombinant human amylin served as control. (18b) Whisker box plots comparing the concentration of amylin, measured by ELISA, in RBCs from healthy individuals (h; dark green; n=66) versus individuals with various diseases or combination thereof, including type-2 diabetes (T2D; blue; n=69), heart failure (HF) with diabetes (HF-T2D; dark red; n=49) and without diabetes (HF w/o T2D; light red; n=59), cancer with diabetes (C-T2D; black; n=33) and without diabetes (C; gray; n=58), and stroke (S; yellow; n=13). RBC lysates from patients with type 1 diabetes (T1D; black; n=5) are the negative control for amylin. Statistical significance of the differences in amylin level was assessed using One-way ANOVA with the Bonferroni post-test for comparing all pairs of columns. *P<0.05, P<0.01, *P<0.001, ****P<0.0001. (18d, 18e, 18f, 18g, 18h, 18i, 18j) The correlation between RBC amylin and HbA1c in groups of healthy (18c) and diseased individuals (18d, 18e, 18f, 18g, 18h) described in (18b). Out-of axis amylin-HbA1c levels: 25.2-5.8 and 12.2-4.6 in (18d); 16.3-5.5 in (18f) and 10.7-5.3 and 13.1-5.1 in (18i), respectively. The Spearman nonparametric correlation analysis was performed in GraphPad and the values for the Spearman r and P are indicated on the plots.
Figure 18B:
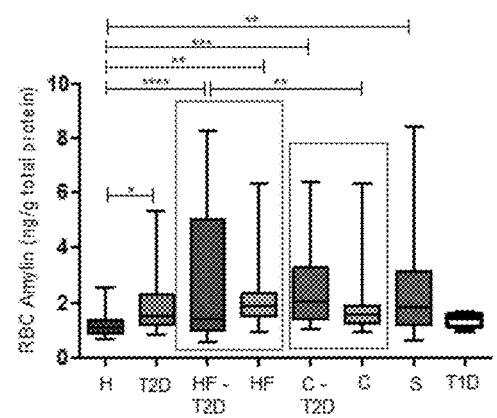
Figure 18C:
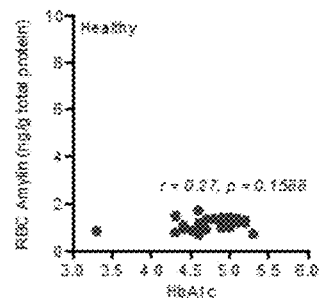
Figure 18D:
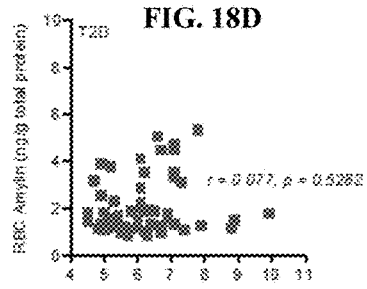
Figure 18E:
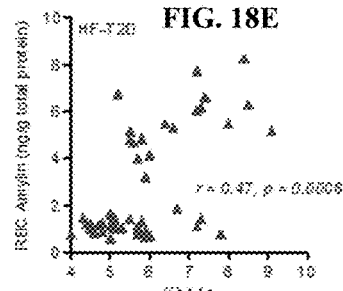
Figure 18F:
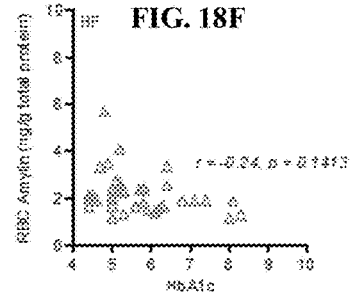
Figure 18G:
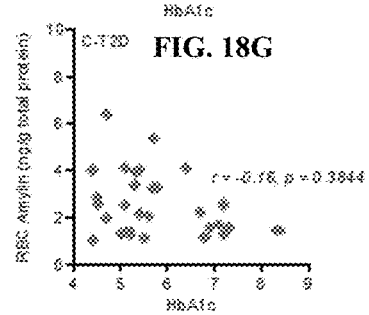
Figure 18H:
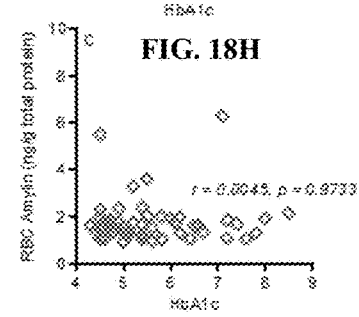
Figure 18I:
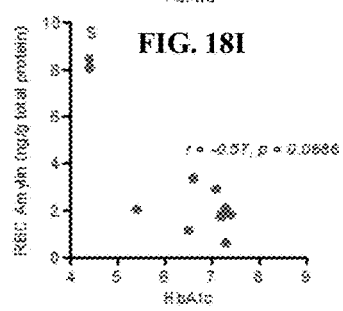

The relationship between HbA1c level (the common marker of hyperglycemia) and amylin concentration in RBC lysates from patients with type-2 diabetes or diseases that are commonly associated with insulin resistance was assessed, including heart failure, cancer and stroke. Western blot analysis of matched plasma, RBC lysate and white blood cell (WBC) lysate from a human with type-2 diabetes (the positive control for amylin dyshomeostasis) detected both monomeric amylin (FIG. 18 A) and amylin-positive higher molecular weight bands (FIG. 24). RBC lysates from individuals with a primary diagnosis of type-2 diabetes (T2D) (without heart failure, cancer or stroke) had higher amylin concentration than those from healthy individuals (H) and patients with type-1 diabetes (T1D group; the negative control for amylin) (FIG. 18B). Patients with a primary diagnosis of heart failure (HF), cancer (C), or stroke (S) also had elevated RBC amylin levels independent of type-2 diabetes as a secondary diagnosis (FIG. 18B). Table 3 describes the average amount of amylin (ng/g) in each patient population erythrocytes as depicted in FIG. 18B. Lighter colored symbols in the HF and C groups indicate heart failure or cancer without type-2 diabetes. RBC amylin and HbA1c levels were highly variable in all groups (FIG. 18C-I), except in patients with HF and type-2 diabetes in whom higher HbA1c levels correlated with RBC amylin accumulation. There were non-significant inverse correlations between HbA1c and RBC amylin levels in the HF without diabetes (FIG. 18F), cancer with diabetes (FIG. 18G) and stroke (FIG. 18I) groups.

TABLE 3

| | Average amount of amylin (ng/g) in each patient population | | | | | | | |
|---|---|---|---|---|---|---|---|---|
| | Healthy | T2D | HF-T2D | HF | C-T2D | C | S | T1D |
| Avg Amylin (ng/g) | 1.20035 | 1.987502 | 2.751755 | 2.100945 | 2.457987 | 1.761388 | 2.800678 | 1.36667 |

These results suggest that type-2 diabetes and diseases associated with insulin resistance such as heart failure, cancer and stroke promote amylin accumulation in RBCs in humans.

Figure 19A:
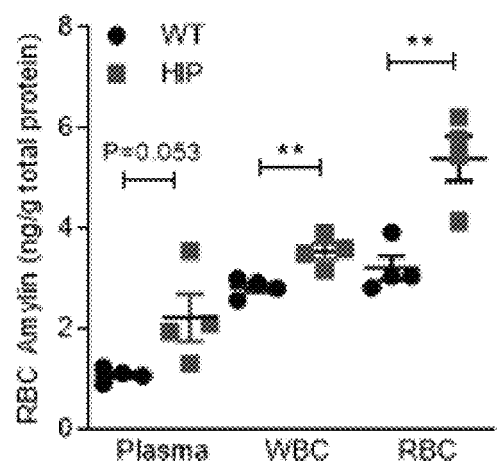
FIGS. 19A-19F show accumulation of amyloid-forming human amylin in RBCs from diabetic rats. (19a) Amylin concentration, measured by ELISA, in matched plasma and lysates of WBCs and RBCs from HIP rats and WT littermates (n=4/group). (19b) Representative flow cytometry graphs (upper) and mean intensity (lower) for amylin/Alexa Fluor 488 fluorescence in RBCs from healthy, prediabetic and diabetic HIP rats (n=5 rats/group). (19c) Amylin concentration in RBC lysates from 16 months old WT rats (n=7) and healthy (n=6), prediabetic (n=15) and diabetic (n=16) HIP rats measured by ELISA. (d and e) Representative images of co-staining for amylin and hemoglobin (19d) and amylin and glycophorin A (19e) in RBCs from age-matched WT and diabetic HIP rats (n=3 rats/group). Scale bar, 10 μm (top row) and 5 μm (middle and bottom rows). (19f) Representative STORM images showing RBCS from HIP and WT rats stained for human amylin (red) and Glycophorin A (green). (Scale bar 2 μm). (n=3 for each rat group). *P<0.05; **P<0.01 by t-test (19a) and One-way ANOVA (19b and 19c).

Example 2: Amylin Deposition in RBCs Results from Hypersecretion of Amyloid-Forming Human Amylin The HIP rat is a unique animal model for late-life onset type-2 diabetes as it is characterized by pancreatic expression of the human (amyloid-forming) variant of amylin, whereas other rodent models for type-2 diabetes express only the native, non-amyloid forming amylin. As in humans, the development of type-2 diabetes in HIP rats is associated with pancreatic amyloid (FIG. 25). the amylin content in RBCs, WBCs, and plasma from diabetic HIP rats and non-diabetic WT littermates (FIG. 19A) was compared. Amylin was concentrated in RBCs and the difference in amylin levels between WT and diabetic HIP rats was greater in RBCs than in plasma or WBCs (FIG. 19A).

Figure 19B:
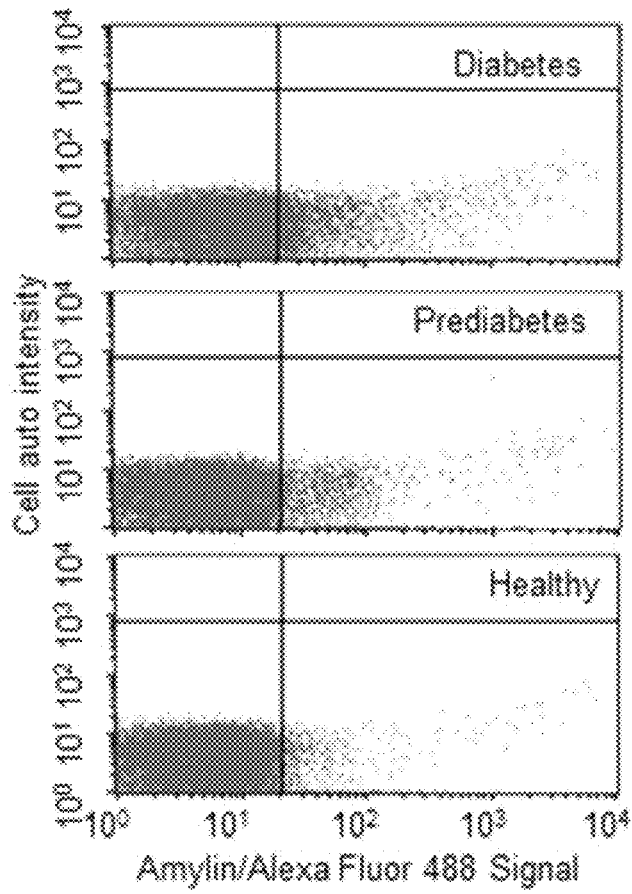
Figure 19C:
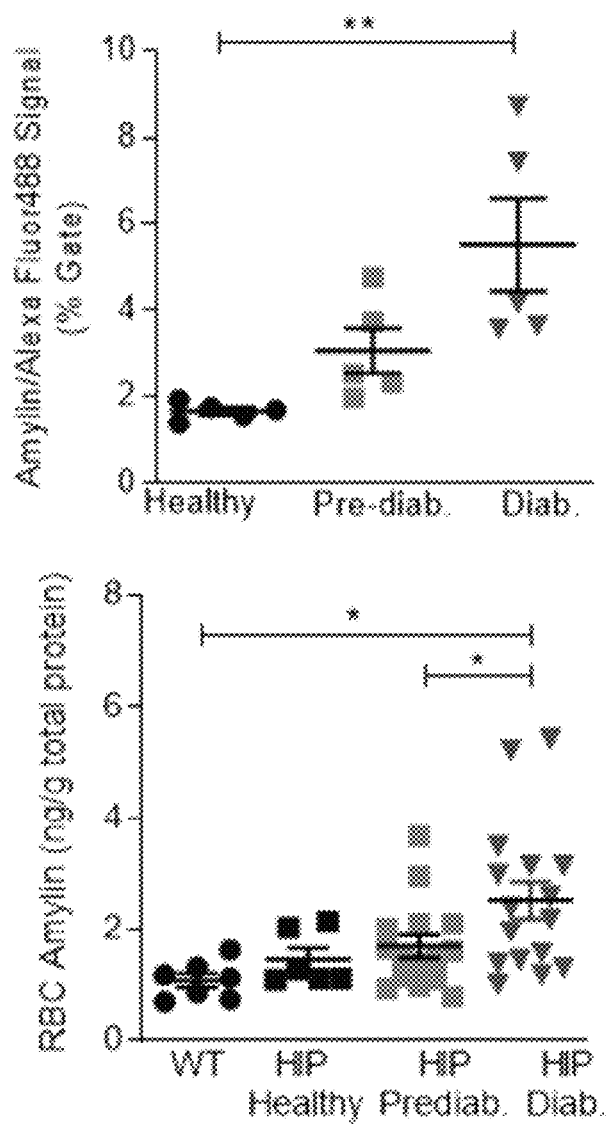

Analysis of freshly packed RBCs by flow cytometry (FIG. 19B) and amylin ELISA (FIG. 19C) revealed a correlation between RBC amylin levels and different levels of non-fasted blood glucose (normal, <11 mM, 6-8 months old; prediabetic, 11-14 mM on two consecutive measurements separated by >3 days, 10-12 months old; and diabetic, >14 mM on two consecutive measurements, separated by >3 days; 14-16 months old).

Figure 19D:
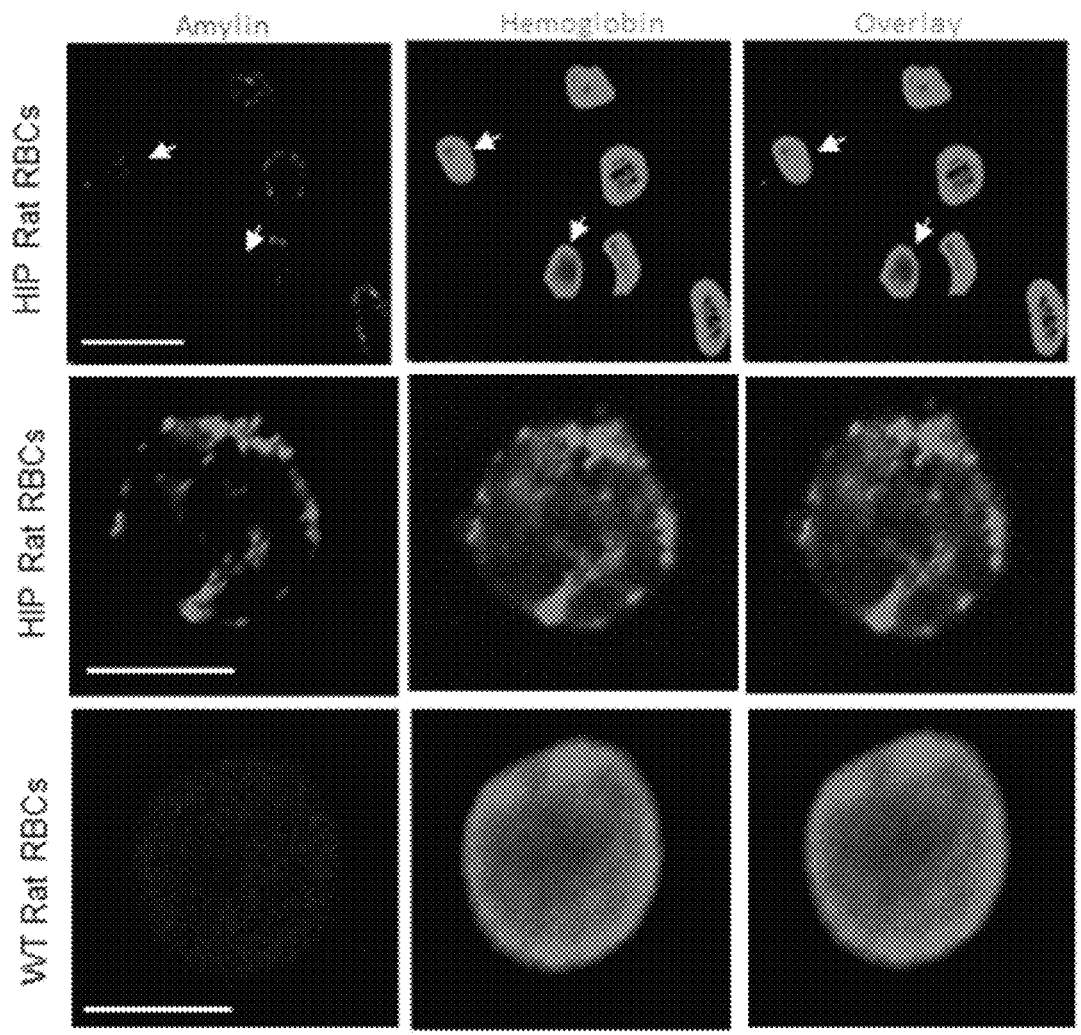
Figure 19E:
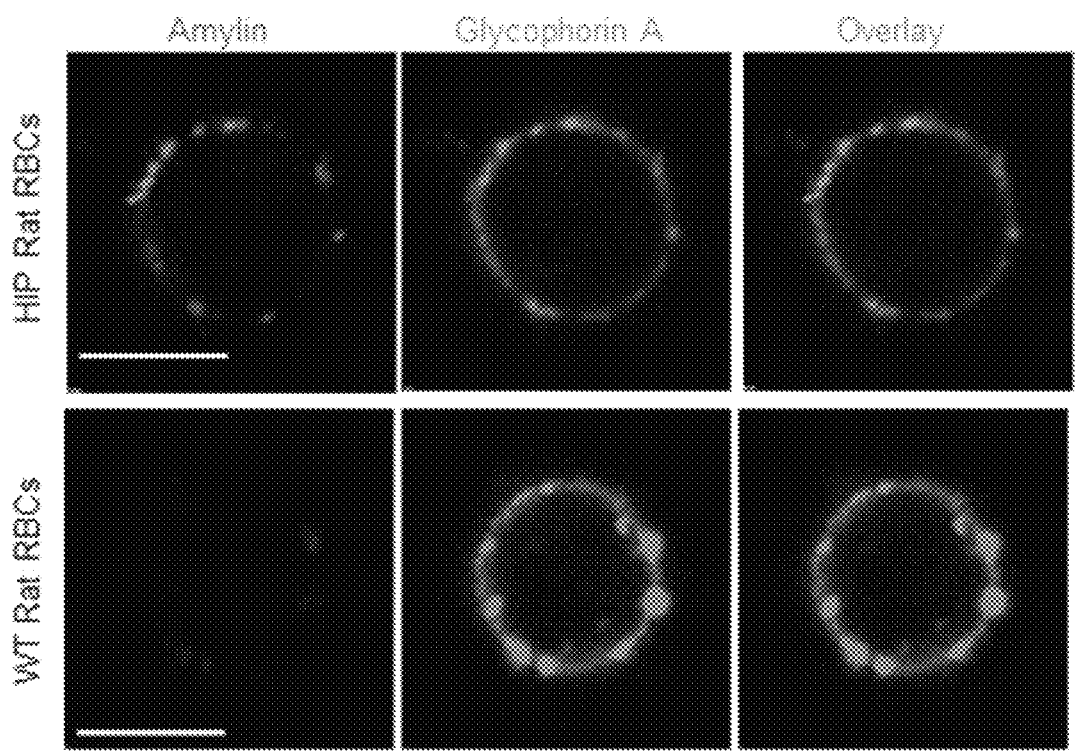
Figure 19F:
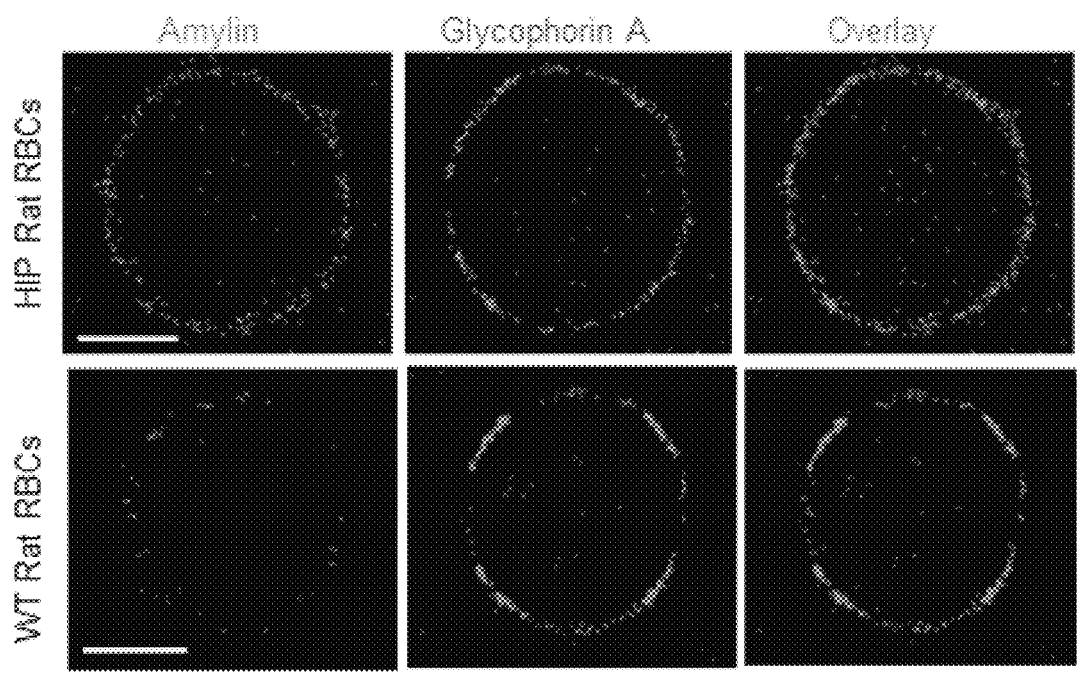
Figure 26:
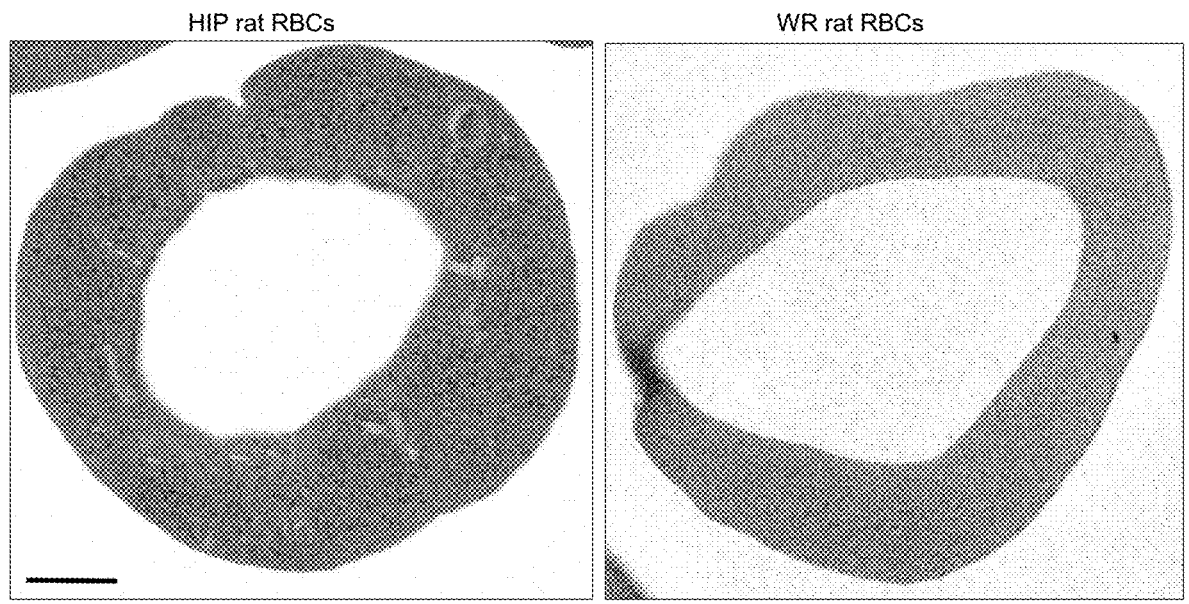
FIG. 26 shows representative TEM images showing RBCs from HIP and WT rats, stained with human amylin primary antibody and gold (10 nm) labelled secondary antibody. (Scale bar 1 μm)

Confocal microscopy analysis of RBCs that were double-stained for amylin and hemoglobin showed amylin deposition on RBCs from HIP rats (FIG. 19D). Amylin appeared to co-localize with glycophorin A (FIG. 19E), a membrane protein that is specific to RBCs, suggesting amylin accumulation on the RBC membrane. The analysis of RBCs co-stained for amylin and glycophorin A using super-resolution imaging (STORM) showed the presence of amylin within the RBC membrane with some dense patches on the outer part of the cell membrane (FIG. 19F). Electron microscopic examination of immunogold-labeled thin sections of epoxy resin-embedded RBCs indicated the presence of amylin within the cell membrane (FIG. 26; arrowhead pointing to amylin deposits).

The results demonstrate that hypersecretion of the amyloid-forming human variant of amylin leads to amylin deposition within circulating RBCs.

Example 3: Amylin-Coated RBCs have Lower Deformability and Functional (Non-Glycated) Hemoglobin Next, pathophysiological characteristics of RBCs from diabetic HIP rats and RBCs from diabetic rats without amylin dyshomeostasis (UCD rats) and non-diabetic WT rats, as they express only the non-amyloid forming rat amylin was investigated. Compared to RBCs from WT rats, RBCs from HIP rats contained less functional (non-glycated) hemoglobin (FIG. 20A), whereas there was no difference between UCD and WT rats. RBCs of HIP, UCD and WT rats (~12 months old rats) had similar oxygen dissociation curves (FIG. 20B) indicating that the affinity of hemoglobin for oxygen, the release of bound oxygen and the partial oxygen pressure for maintaining oxygen saturation are not significantly affected by amylin dyshomeostasis or hyperglycemia.

Figure 20D:
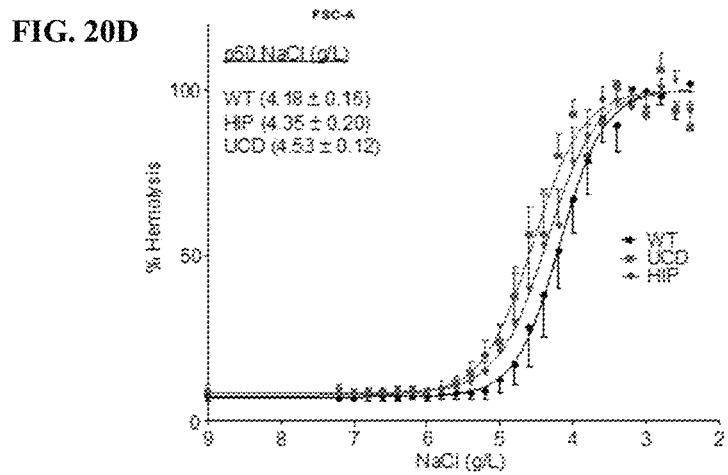

In flow cytometry experiments, the distribution of the forward scattering (FSC) signals by RBCs from WT rats (FIG. 20C; lowest peak) was bimodal, which reflects the biconcave disk shape of normal RBCs. In the case of amylin-coated RBCs from diabetic HIP rats, the FSC distribution was monomodal (FIG. 20C; highest peak), indicating changes in RBC morphology towards a more spherical shape. The Pearson coefficient of dissymmetry (PCD), which indicates the departure from sphericity, suggested distinct morphological changes in RBCs from HIP rats compared to WT and UCD rats (FIG. 20C, middle peak). Incubation of RBCs from WT rats with aggregated human amylin for 4 hours (as described in previous studies) replicated the morphological change observed in HIP rat RBCs (FIG. 27). Altered shape of RBCs from HIP and UCD rats did not affect the response to an osmotic resistance test, as the propensity for hemolysis in hypo-osmotic solutions was comparable for RBCs from all three rat groups (FIG. 20D).

These results show that amylin deposition in RBCs is associated with lower hemoglobin concentrations and reduced RBC deformability, independently of effects of chronic glucose levels. At an early stage of diabetes, the cumulative effects of amylin dyshomeostasis and hyperglycemia (as in HIP rats) or hyperglycemia alone (as in UCD rats) do not appear to induce significant changes in hemolysis and oxygen dissociation.

Figure 20E:
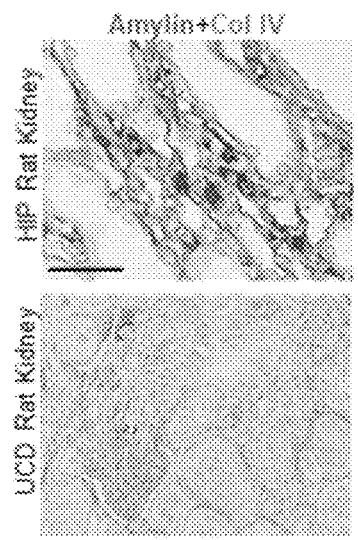
Figure 20F:
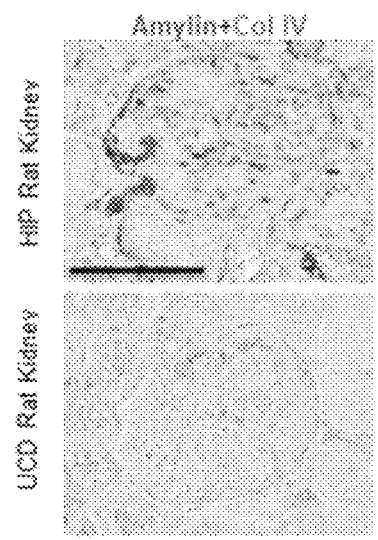
Figure 20G:
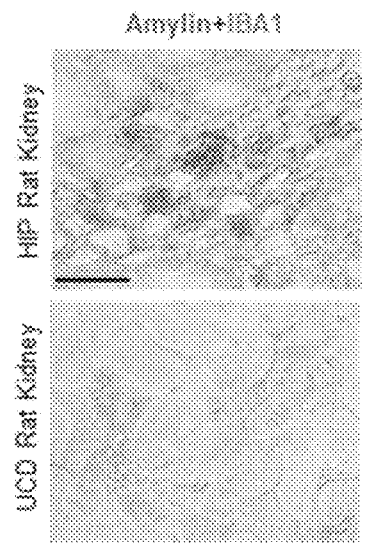
Figure 20H:
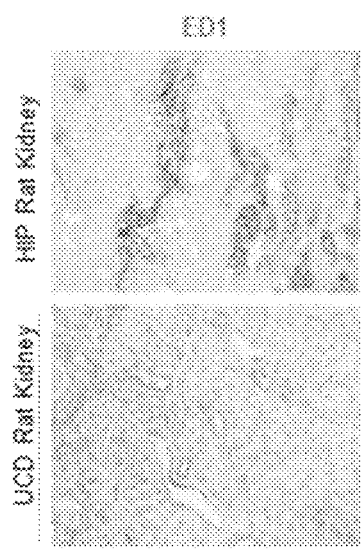

Example 4: The Microvasculature is Disrupted in Kidneys of Rats with Amylin Dyshomeostasis Next the structural integrity of the capillary network and the stability of the capillary beds in kidneys from age- and blood glucose-matched HIP and UCD rats was investigated. immunohistochemistry with antibodies against amylin (brown, dark stain) and collagen IV (Col IV; green, light stain) were used, a component of the basement membrane, to anatomically localize amylin deposition with respect to the vasculature. In HIP rat kidneys, there were patches of amylin deposits in arterioles, interstitial tissue between the tubules (FIG. 20E) and glomeruli (FIG. 20F). Vascular amylin deposition correlated with accumulation of macrophages, as indicated by co-staining for amylin and the ionized calcium-binding adapter molecule 1 (IBA1), a marker of macrophage activation (FIG. 20G). There were macrophages in areas of amylin deposition, which may indicate a potential role for these cells in the clearance of vascular amylin deposition. Staining with ED1 (FIG. 20H), an antibody against the cluster of differentiation (CD) 68 protein (that is highly expressed by circulating macrophages), supports the increased activity of macrophages in areas of vascular amylin deposition. In contrast, vascular amylin deposits and macrophage infiltration were not found in kidneys from diabetic UCD rats.

These data suggest that amylin dyshomeostasis injures the capillaries, which may be associated with systemic inflammatory responses leading to macrophage infiltration that may exacerbate ischemic vascular injury in HIP rats.

Example 5: Amylin Dyshomeostasis Activates Renal Hypoxia Signaling Pathways

Figure 21A:
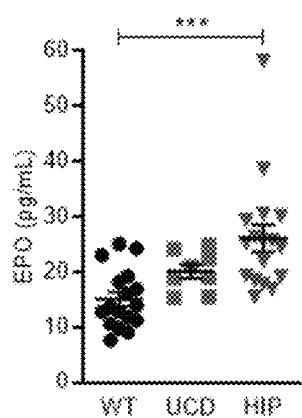
FIGS. 21A-21H show modulation of renal hypoxia markers by amylin dyshomeostasis. (21a) EPO levels in plasma from 16 months WT rats (n=17), diabetic UCD rats (n=8) and diabetic HIP rats (n=17). (21b) Percentage number of reticulocytes over total numbers of RBCs in blood of WT, HIP and UCD rats (n=3 for each rat group). (21c) Hematocrit levels in diabetic HIP and UCD rats and WT controls (n=6 rats/group). (21d, 21e, 21f, 21g, 21-21h) Protein levels of HIF-1α (21d), HIF-2α (21e), arginase-1 (21f) and arginase-2 (21g) and arginase activity (21h) measured by ELISA in renal tissues from 16 months old WT rats and diabetic UCD and HIP rats (n=10 rats/group). *P<0.05; P<0.01; *P<0.001 by One-way ANOVA with Tukey's post-test.
Figure 21B:
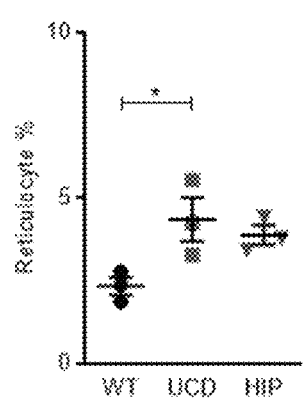
Figure 21C:
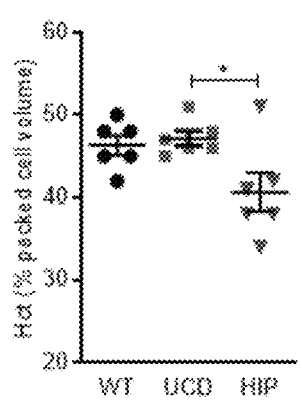
Figure 21D:
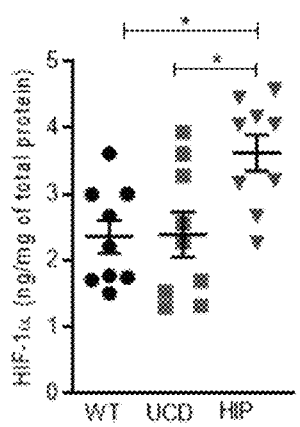
Figure 21E:
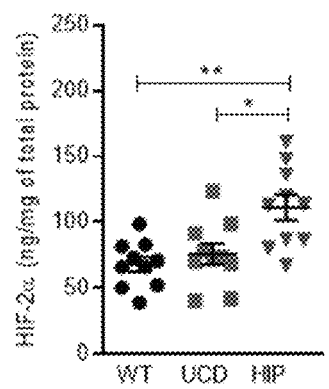
Figure 21F:
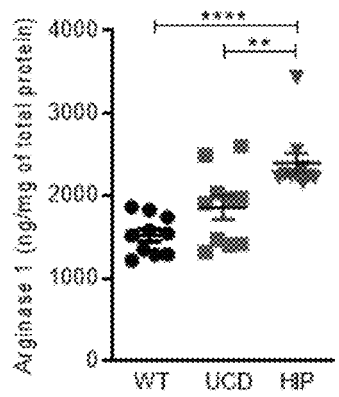
Figure 21G:
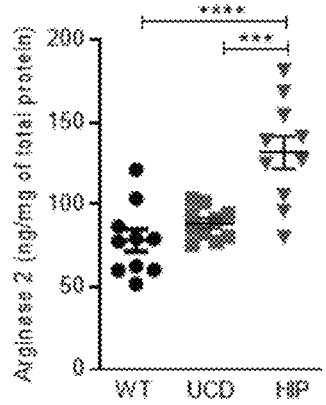
Figure 21H:
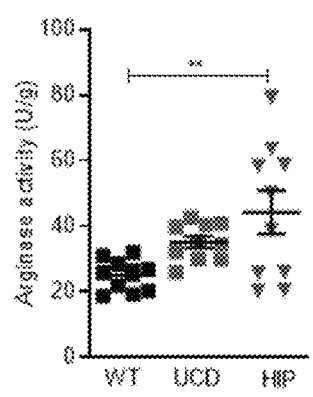
Figure 28A:
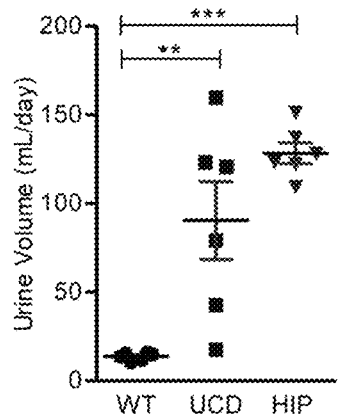
FIGS. 28A-28C show volume of urine excretion (28A), albuminuria (28B) and creatinine clearance rate (28C) in 16 months old WT, diabetic UCD and diabetic HIP rats (n=6 rats/group). P<0.01; *P<0.001 by One-way ANOVA.
Figure 28B:
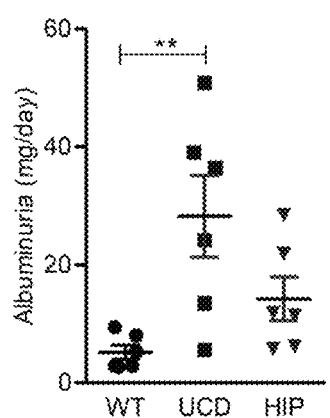
Figure 28C:
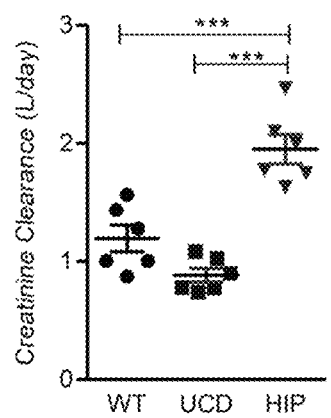
Figure 29:
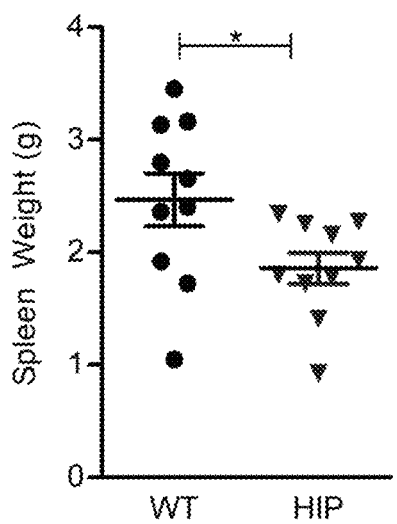
FIG. 29 shows gross spleen weights of 16 months old WT rats and diabetic HIP rats (n=10 spleens/group). Data are means±SEM. *P<0.05
Figure 30:
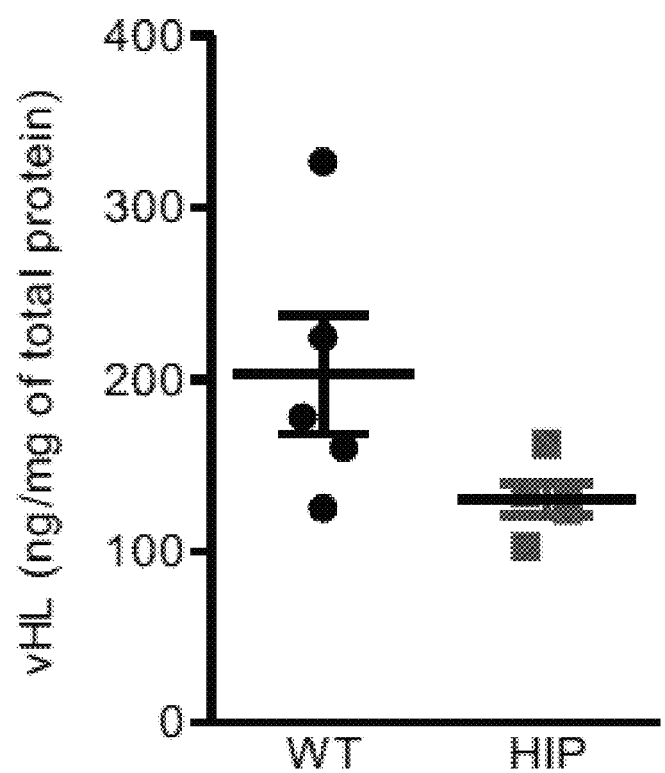
FIG. 30 shows levels of von Hippel-Lindau (vHL) protein in the renal tissues from 16 months old WT rats and diabetic HIP rats (n=5 rats/group). Data are means±SEM.

The kidney is a critical component of a regulatory feedback loop that controls the hematocrit via EPO production. Both HIP and UCD rats had renal dysfunction, as indicated by polyuria and albuminuria (FIGS. 28A and 28Bb). Creatinine clearance was elevated in diabetic HIP rats compared with WT littermates and diabetic UCD rats (FIG. 28C). The plasma level of EPO, the hormone that signals an increased demand for RBCs to the bone marrow, was higher in diabetic HIP rats than in WT littermates (FIG. 21A) and tended to be higher in age-matched diabetic UCD rats vs. WT rats (P=0.27). The reticulocyte count was also higher in HIP than in WT rats (FIG. 21B). Despite elevated plasma EPO levels, the average hematocrit was not different in HIP rats compared with WT littermates, but was lower in HIP compared to UCD rats (FIG. 21C). The spleen, a major blood reservoir, had lower weight in diabetic HIP rats compared to age-matched WT rats (FIG. 29). Compared with diabetic UCD rats and healthy WT rats, diabetic HIP rats had elevated levels of HIF-1α and HIF-2α in whole kidney tissue homogenates (FIGS. 21D and 21E). Consistent with elevated HIF-2α, HIP rat kidneys also had upregulated arginase-1 and 2 proteins (FIGS. 21F and 21G) and greater arginase activity (FIG. 21H). Increased stabilization of HIF α units in HIP rat kidney tissue correlated with a trend towards downregulation of the von Hippel-Lindau (vHL) tumor suppressor protein (FIG. 30) suggesting impaired degradation of HIF α units.

These results suggest that activation of hypoxia signaling in kidneys and downstream upregulation of EPO are associated with pathologic erythropoiesis and amylin deposition in RBCs.

Figure 31:
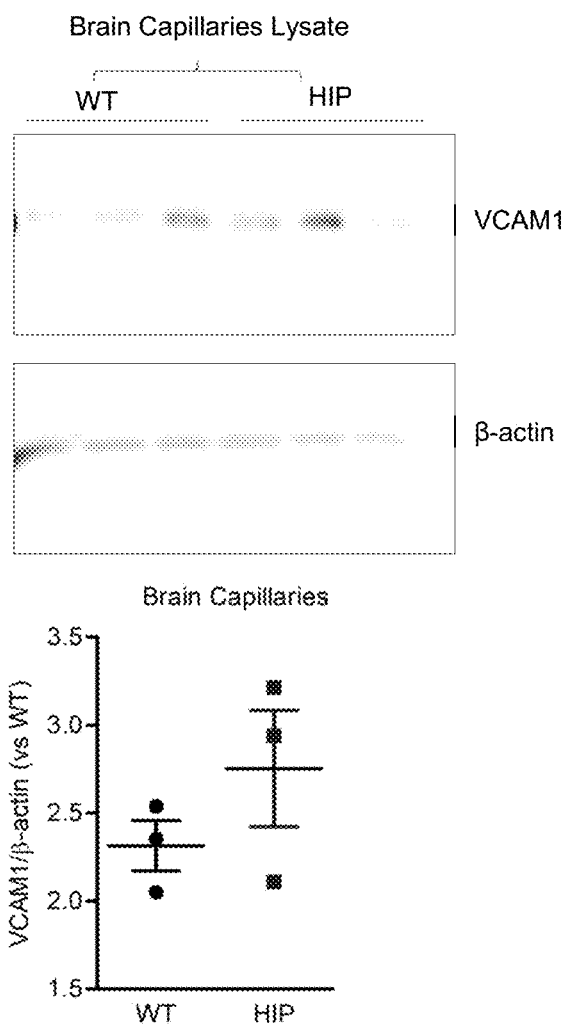
FIG. 31 shows western blot and ELISA analyses for VCAM-1 expression in kidney capillaries lysates of WT and HIP rats (n=3 rats/group).
Figure 33A:
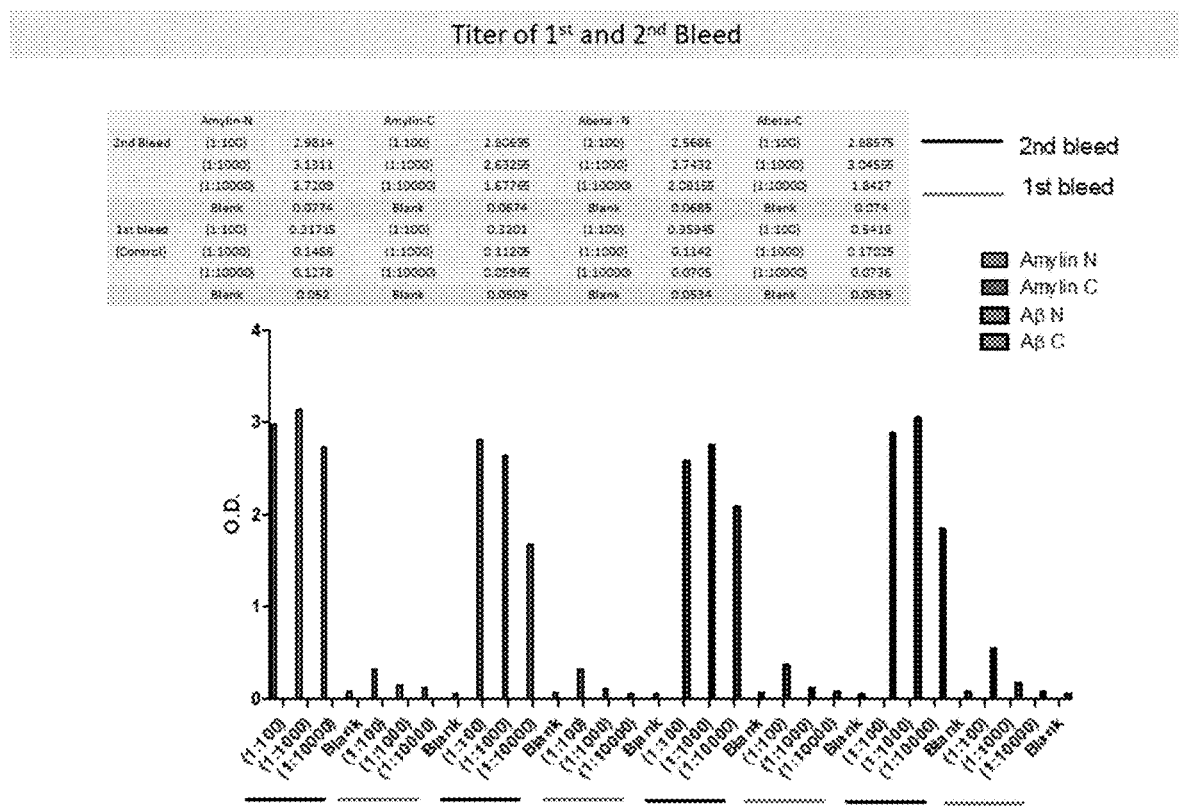
FIGS. 33A-33D show ELISA showing higher titers in collected bleeds. 33A. ELISA of Amylin N-terminal, C-terminal and Aβ N-terminal, C-terminal antibody for 1st and 2nd bleed. 33B. ELISA of Amylin N-terminal, C-terminal and Aβ N-terminal, C-terminal antibody for 2nd and 3rd bleed. 33C. ELISA of Amylin N-terminal, C-terminal and Aβ N-terminal, C-terminal antibody for 3rd and 4th bleed. 33D. ELISA of Amylin N-terminal, C-terminal and Aβ N-terminal, C-terminal antibody for Final Bleed.
Figure 33B:
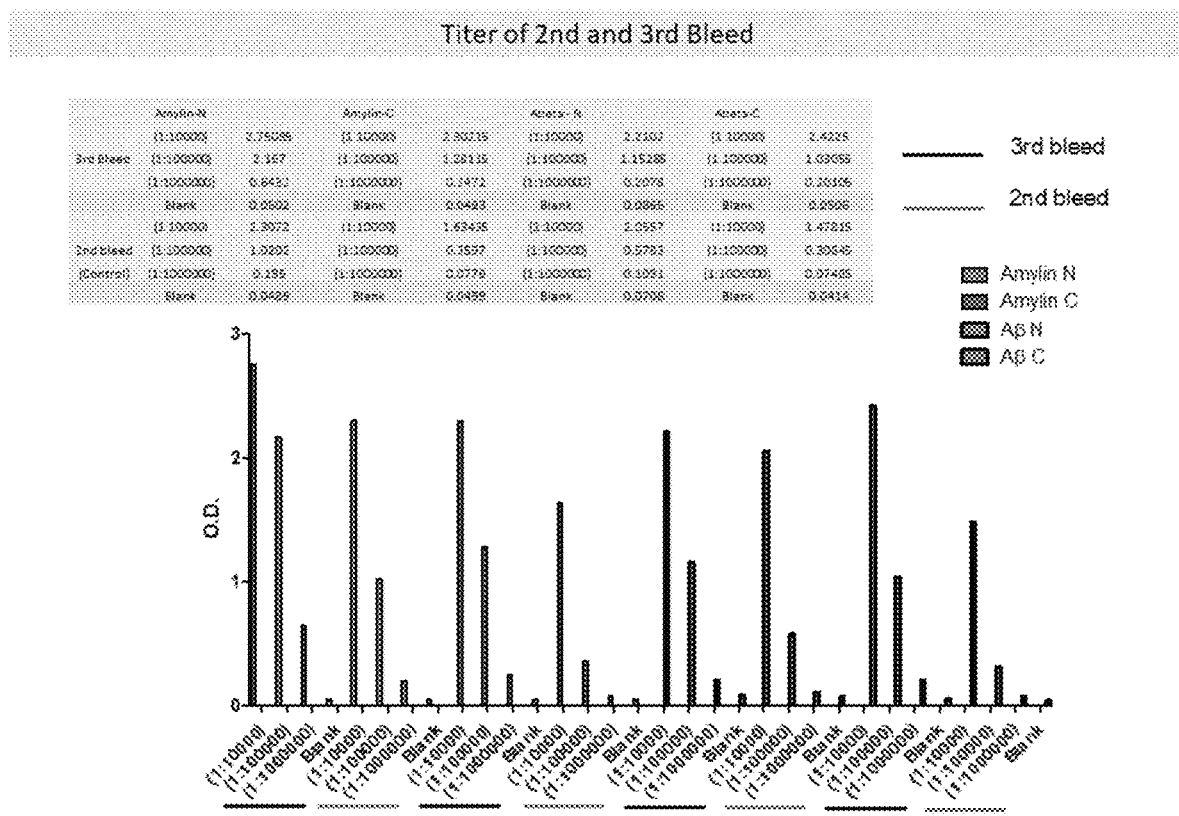
Figure 33C:
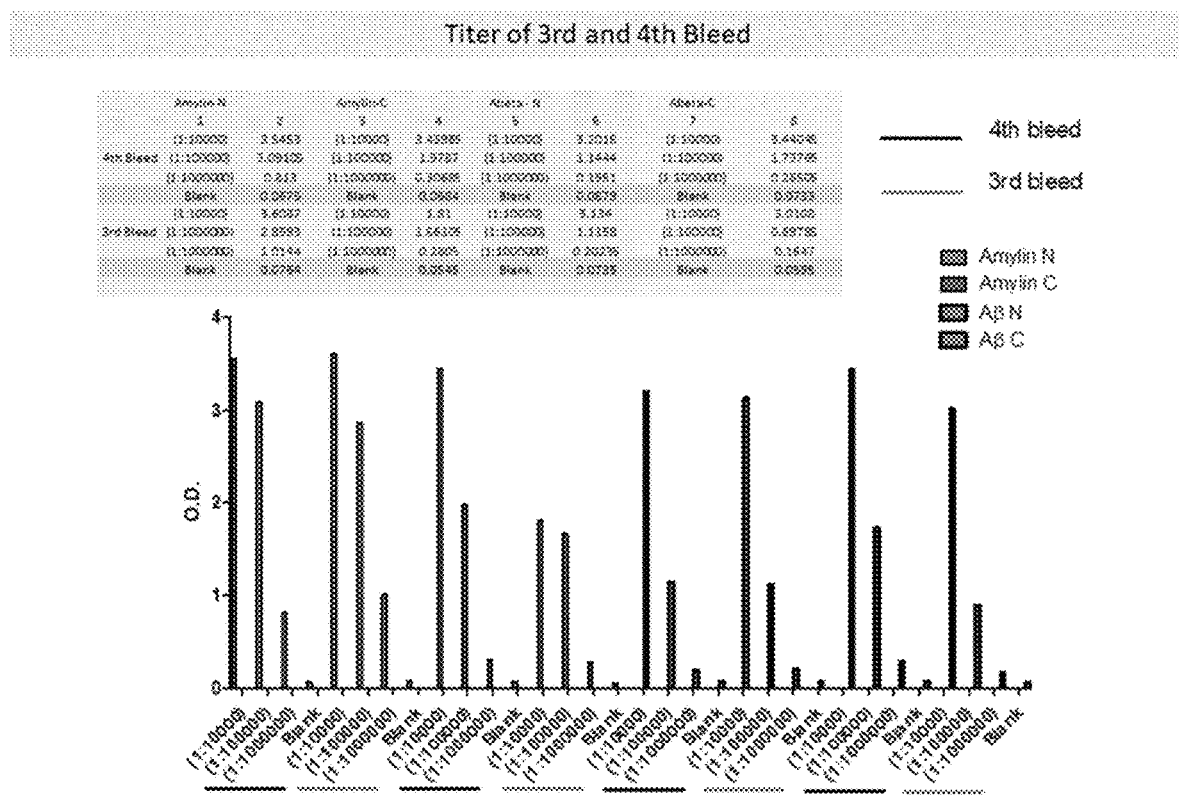
Figure 33D:
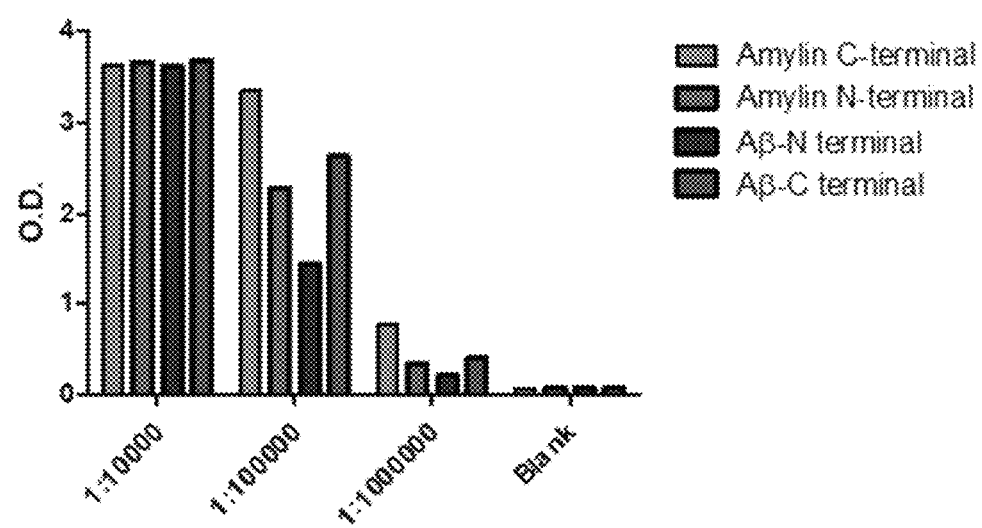

Example 6: Blocking of Adhesion Proteins in Endothelium Reverses Amylin Dyshomeostasis and HIF Activation The adhesion of RBCs to cultured vascular endothelial cells (ECs) under flow condition tended to be greater for HIP rat RBCs than RBCs from UCD rats (P=0.17) and from WT rats (P=0.17) (FIG. 22A). Greater adhesion of RBCs from HIP rats to ECs was found in experiments without flow condition (FIG. 22B) in an adhesion test in which RBCs from WT rats that were incubated with 50 μM synthetic human amylin for 4 hours is shown in FIG. 22C. Analysis of kidney capillary lysates by Western blot (A) and ELISA (B) showed a trend towards upregulation of the expression of vascular cell adhesion molecule 1 (VCAM-1) in HIP rats (FIG. 31). Taken together, these results suggest that the cell membrane adhesion proteins may play a role in amylin accumulation at the RBC-capillary interface. To test this hypothesis, EETs were used, which are primarily expressed by vascular ECs and RBCs and are known to downregulate the expression of VCAM-1 in endothelium. Ex vivo incubation with (±)14(15)-EET reduced the adhesion of HIP rat RBCs to cultured endothelial cells (FIG. 22D). Upregulation of EETs by treatment with an inhibitor of soluble epoxide hydrolase, the enzyme that degrades endogenous EETs, was associated with lower amylin deposition in renal microvasculature (the HIP-T group; FIG. 22E). The treatment lowered renal accumulation of HIF-2α (FIG. 22F) and HIF-1α

(FIG. 22G) and had variable effects on arginase expression and arginase activation (FIG. 32) in HIP rat kidneys.

Taken together, these results indicate that 1) reduced capillary RBC flux owing to amylin deposition on RBCs and the capillary wall likely contributes to tissue hypoxia in HIP rats and 2) EETs reduce this effect by downregulation of adhesion proteins in the vascular endothelium.

Figure 23A:
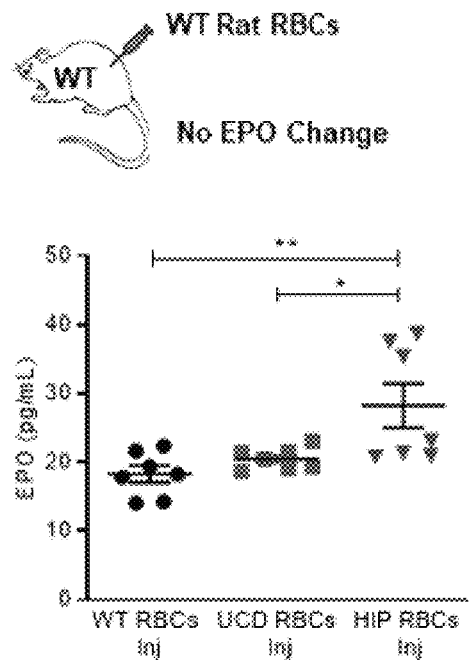
Figure 23B:
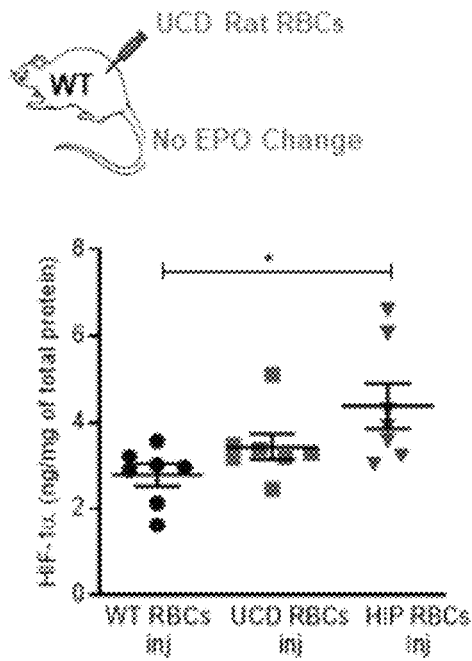
Figure 23C:
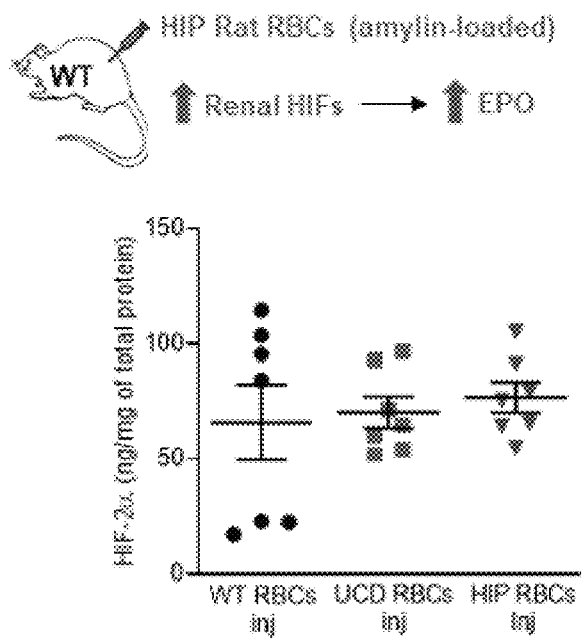

Example 7: Transfused Amylin-Coated RBCs Upregulate EPO Through HIF-2α Activation in Kidneys RBCs act as both oxygen carriers and mediators of oxygen sensing and signaling pathways within ECs. To determine whether amylin deposition on RBCs activates hypoxia signaling pathways in tissues, amylin-coated RBCs from HIP rats were administered to WT rats. Rats were given 300 µl freshly packed RBCs/day for seven days. WT rats given similar volumes of RBCs from diabetic UCD rats were used as positive controls for the possible effects of hyperglycemia on RBC function, whereas WT rats receiving RBCs from WT rats served as negative controls. Plasma levels of EPO were elevated in WT rats receiving amylin-coated RBCs from HIP rats compared to WT rats that received either RBCs from diabetic UCD rats or WT rats (FIG. 23A). Kidneys of WT rats receiving HIP rat RBCs had increased stabilization of HIF-1α (FIG. 23B) but no difference in HIF-2α levels (FIG. 23C), compared with rats in the two control groups.

Figure 23D:
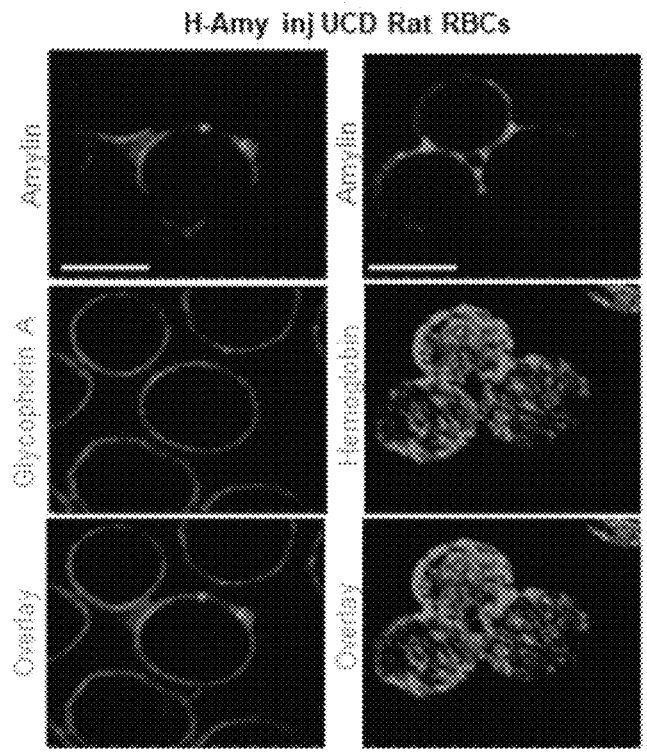
Figure 23E:
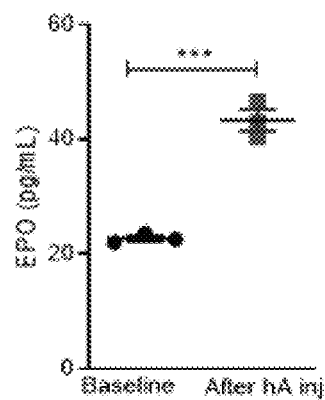
Figure 23F:
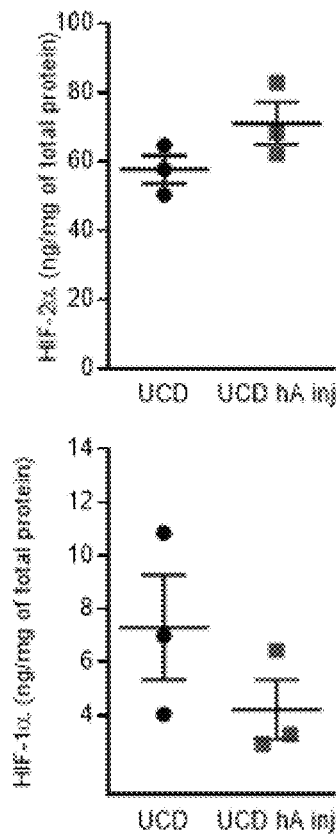
Figure 23G:
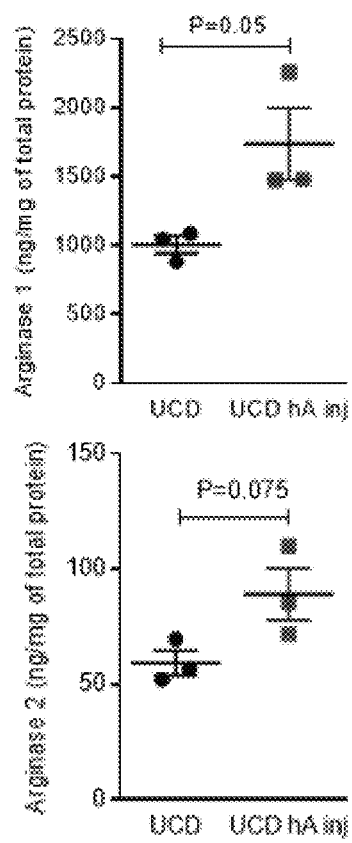

To examine further a possible 'amylin stress" on oxygen-sensing pathways, aggregated human amylin (hA) (0.08 µg/g body weight) was intravenously administered to diabetic UCD rats, daily, for one week. Intravenous infusion of aggregated human amylin in UCD rats led to amylin deposition on RBCs (FIG. 23D). This acute "amylin stress" provoked an increase in plasma EPO level (FIG. 23E; the "after hA inj" rat group) and no difference in renal HIF-2α and HIF-1α levels in whole kidney tissue homogenate (FIG. 23F). Arginase 1 protein levels were elevated in kidney tissue homogenates from amylin-infused UCD rats, whereas there was no significant change of arginase 2 protein expression (FIG. 23G).

Figure 23H:
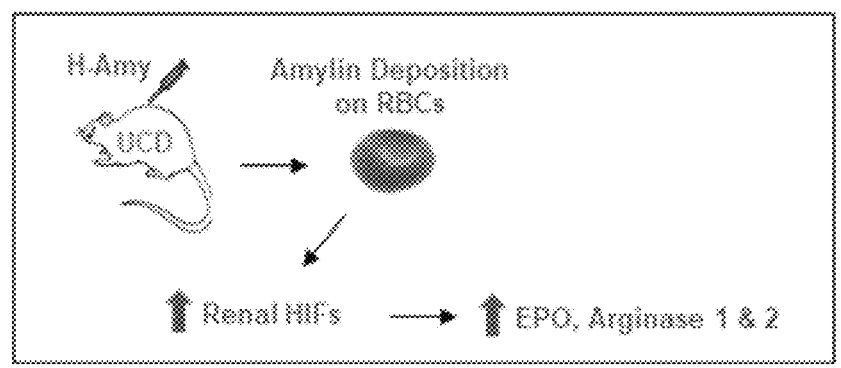

These data indicate elevated EPO and accumulation of HIFs in kidneys as a direct response to circulating amylin-coated RBCs (FIG. 23H).

Example 8: ELISA Showed High Titers in Collected Bleeds

Direct ELISA was done to check the titer between the 1st (prebleed), 2nd, 3rd, 4th and final bleed which were collected from the different time point from the rabbits. First the comparison between the 1st (Prebleed) and 2nd bleed for the titer 1:100, 1:1000 and 1:10000 (FIG. 33 A) was shown. First bleed (Prebleed) showed O.D equals to blank suggest none of any antibody present in the rabbit before immunization. The comparison between the 2nd and 3rd bleed for the titer 1:10000, 1:100000 and 1:1000000 was determined. Bleed 3rd was found to be higher titer as compared to bleed 2nd (FIG. 33 B). Similarly comparison between the 3rd and 4th bleed for the titer 1:10000, 1:100000 and 1:1000000. Bleed 4th was found to be higher titer as compared to bleed 3rd (FIG. 33 C). Finally, the comparison for final bleed for the titer 1:10000, 1:100000 and 1:1000000 were determined. Final titer for Amylin N-terminal, C-terminal and Aβ N-terminal, C-terminal antibody was obtained at 1:100000 (FIG. 33 D).

Figure 34A:
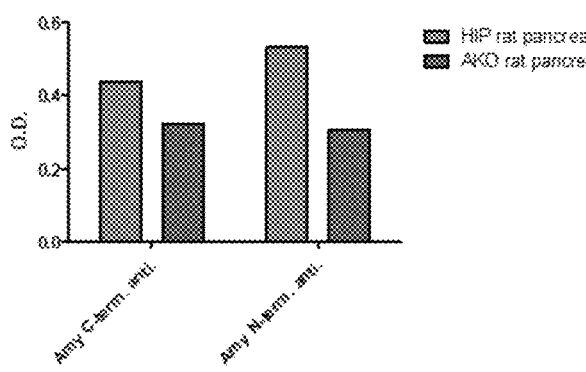
FIGS. 34A-34C show a direct ELISA demonstrating purified antibodies are specific for their antigen. 34A. Direct ELISA of Amylin N-terminal and C-terminal antibody was performed on HIP rat pancreas and AKO rat pancreas. 34B. Direct Elisa of Aβ N-terminal and C-terminal antibody was performed on AD brain and wild type brain. 34C. Diagram of ELISA.
Figure 34B:
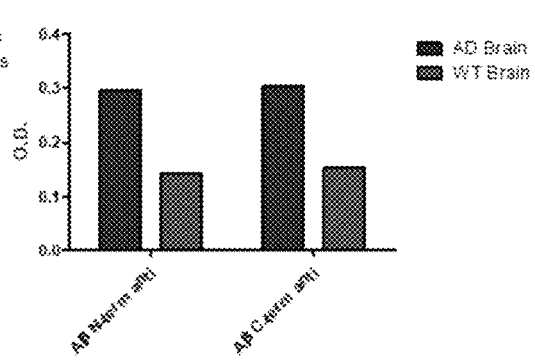
Figure 34C:
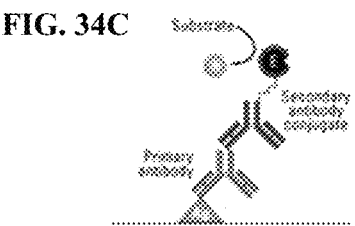

Example 9: Direct ELISA Showed Purified Antibodies are Specific for their Antigen (FIG. 34 A) Showed the direct ELISA for Amylin in pancreas homogenate of HIP rat (overexpressing human amylin in pancreas) and AKO rat (Amylin knockout rat) with Amylin N-terminal and C-terminal antibody. HIP served as a positive control and AKO served as a negative control. Both antibodies detect higher signal in HIP as compared to AKO. (FIG. 34B) Showed the direct ELISA for Aβ in brain homogenate of AD rat (overexpressing human Aβ in brain) and Wild type (WT) rat with AβN-terminal and C-terminal antibody. AD served as a positive control. Both antibodies detect higher signal in AD as compared to WT. FIG. 34 C shows a diagram of how one embodiment of the presently described ELISA functions.

Figure 35:
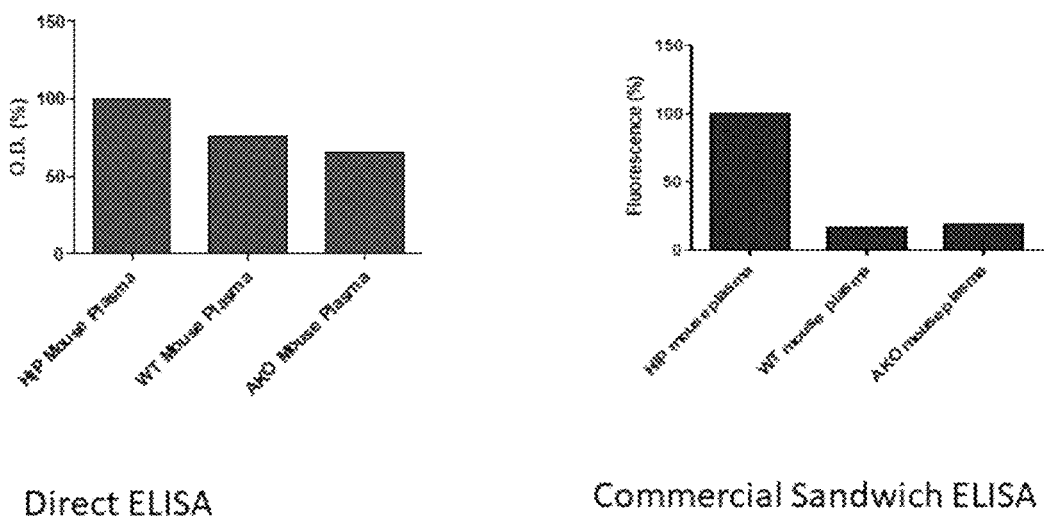
FIG. 35 shows custom ELISA with antibodies showed similar results with commercially available ELISA. Left Panel. Direct Amylin ELISA with generated N-terminal antibody in plasma samples of HIP, WT and AKO mouse. Right Panel. Sandwich Amylin ELISA with commercially available kit in plasma samples of HIP, WT and AKO mouse.

Example 10: Custom ELISA with Antibodies Showed Similar Results with Commercially Available ELISA The Direct ELISA was performed in Plasma of HIP mouse (overexpressing Human IAPP), WT mouse and AKO mouse (Amylin is knockout). Higher signals in HIP mouse Plasma as compared with WT and AKO mouse Plasma (FIG. 35, left panel). At the same time with the same set of samples, the sandwich ELISA was performed with commercially available kit (FIG. 35, right panel). Similar results were found with the Direct ELISA as was found with commercially available ELISA Kit that confirm the present antibody is specific and sensitive for ELISA.

Figure 36A:
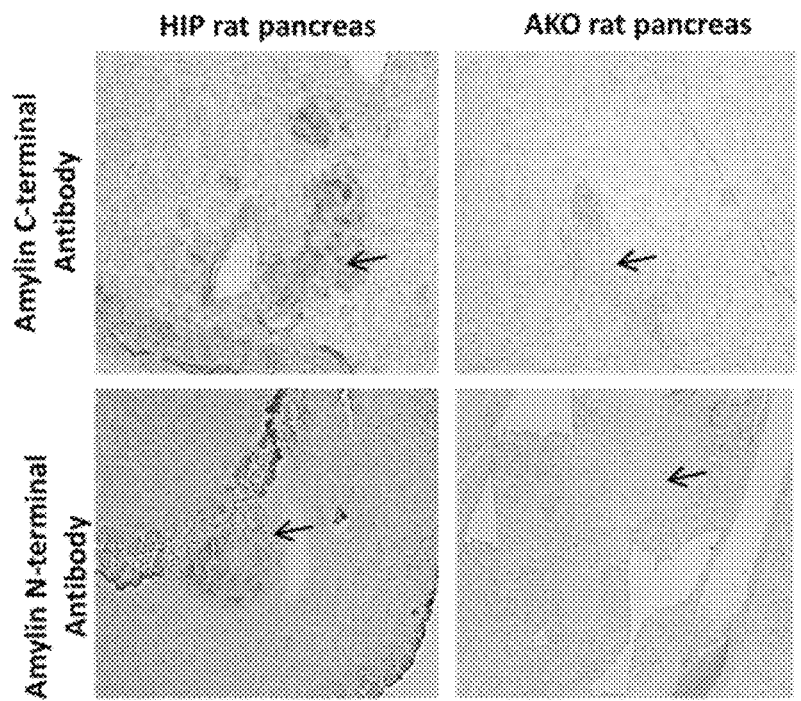
FIGS. 36A-36B show immunohistochemistry delineating how antibodes are specific for their proteins. 36A. Immunohistochemistry of HIP and AKO Rat pancreas with Amylin N-terminal and C-terminal antibody. 36B. Immunohistochemistry of AD rat brain and WT Rat heart with Aβ N-terminal antibody.
Figure 36B:
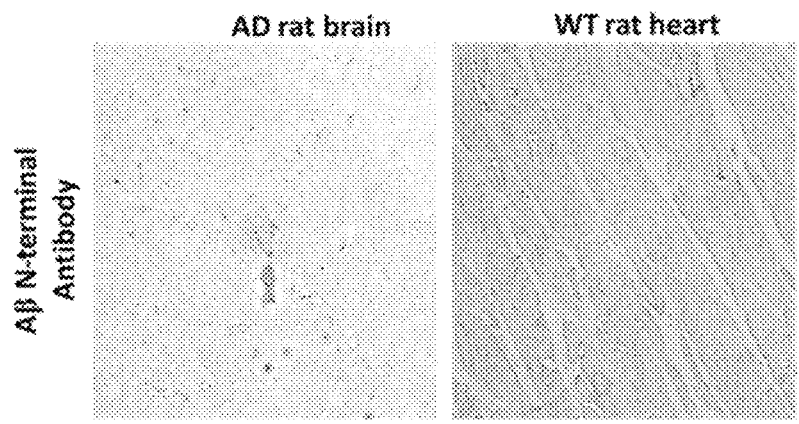

Example 11: Immunohistochemistry Showed Antibodies are Specific for their Proteins Immunohistochemistry was performed using Amylin N-terminal, C-terminal and AβN-terminal antibody in their positive and negative tissue samples sections. Both N terminal and C-terminal antibodies against amylin showed positive signal in HIP pancreas but not in AKO pancreas (arrows) (FIG. 36A). Similarly antibody against AβN-terminal showed positive signal in AD brain sections but not in negative control (WT rat heart) (FIG. 36B).

Figures 37A, 37B:
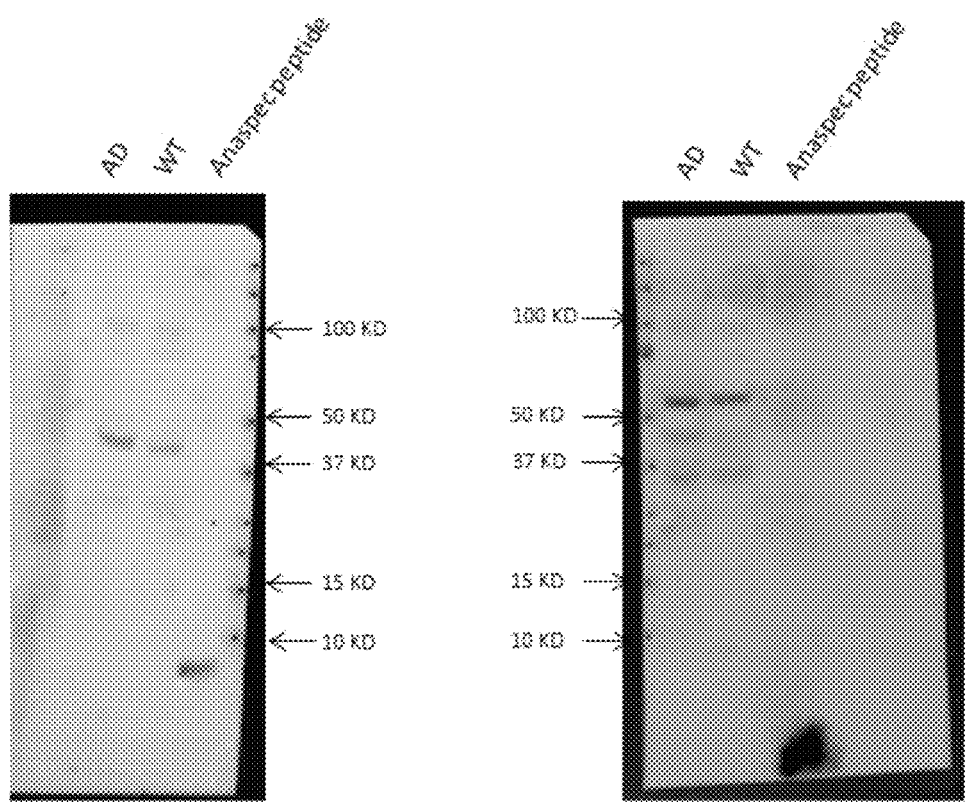
FIGS. 37A-37B show Aβ N-terminal and C-terminal antibodies specifically detect the Aβ peptides in western blot. Western blot in AD brain, WT brain and synthetic peptide using Aβ N-terminal (37A) and Aβ C-terminal antibody (37B).

Example 12: AβN-Terminal and C-Terminal Antibodies Specifically Detect the Aβ Peptides in Western Blot AβN-terminal and Aβ C-terminal antibodies detect the Anaspec Aβ synthetic peptide in western blot at below 10 KD (FIGS. 37A & B).

Example 13 Immunogens and Method Used to Create Amylin and Aβ Antibodies

Figures 38A, 38B:
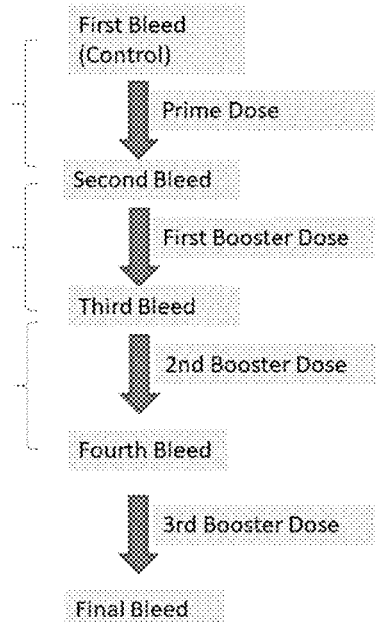
FIGS. 38A-38B show the design and creation of antibodies against amylin and amyloid β peptide. 38A. The peptides used to generate antibodies against amylin and Aβ. 38B. Injection and bleed collection schedule.

FIGS. 38A-B shows the design and creation of antibodies against amylin and amyloid β peptide. FIG. 38 A. The peptides used to generate antibodies against amylin and Aβ. The peptides are also sknown as the following sequence numbers: Amylin peptide (SEQ ID NO: 2); Amylin C (SEQ ID NO: 3); Amylin N (SEQ ID NO: 4); Amyloid β peptide (SEQ ID NO: 5); Aβ N (SEQ ID NO: 6); and Aβ C (SEQ ID NO: 7). FIG. 38 B. shows injection and bleed collection schedule.

Example 14

Keyhole limpet hemocyanin1 (Fragment) KLH sequence used to generate polyclonal antibodies of the invention herein is listed below and referred to as SEQ ID NO: 1.

LSVRLLIVVLALANAENLVRKSVEHLTQEETLDLQAALRELQMDSSS
IGFQKIAAAHGAPASCVHKDTSIACCIFIGMPTTPHWHRAYVVHMER
ALQTKRRTSGLPYWDWTEPITQLPSLAADPVYIDSQGGKAHTNYWYR
GNIDFLDKKTNRAVDDRLFEKVKPGQHTHLMESVLDALEQDEECKEE
IQFELAHNAIHYLVGGKHDYSMANLEYTAYDPIFELHHSNVDRIFAI
WQRLQELRNKDPKAMDCAQELLHQKMEPFSWEDNDIPLTNEHSTPAD
LFDYCELHYDYDTLNLNGMTPEELKTYLDERSSRARAFASFRLKGEG
GSANVFVYVCIPDDNDRNDDHCEKAGDFFVLGGPSEMKWQFYRPYLF
DLSDTVHKMGMKLDGHYTVKAELFSVNGTALPDDLLPHPVVVHHPEK
GETDPPVKHHQSANLLVRKNINDLTREEVLNLREAEHKEQEDRSVDG
YQATAEYHGLPARCPRPDAKDRYACCVHGMPIEPHWHRLEVTQVEDA
LVGRGATIGIPYWDWTEPMTHIPGLAGNKTYVDSHGASHTNPFHSSV
IAFEENAPHTKRQIDQRLFKPATEGHHTDLENQILYAFEQEDYCDFE
VQFEITHNTTHAWTGGSEHFSMSSLHYTAFDPLFYEHEISNVDRLWA
VWQALQMRRHKPYRAHCAISLEHMHLKPFAFSSPLNNNEKTHANAMP
NKIYDYENVLHYTYEDLTFGGISLENIEKMIHENQQEDRIYAGFLLA
GIRTSANVDIFIKTTDSVQHKAGTFAVLGGSKEMKWGEDRVEKFDIT
HVLKDLDLTADGDFEVTVDITEVDGTKLASSLIPHASVIREHARVKF
DKVPRSRLIRKNVDRLSPEEMNELRKALALLKEDKSAGGFQQLGAFH
GEPKWCPSPEASKKFACCVHGMSVFPHWHRLLTVQSENALRRHGYDG
ALPYWDWTSPLNHLPELADHEKYVDPEDGVEKHNPWFDGHIDTVDKT
TTRSVQNKLFEQPEFGHYTSIAKQVLLALEQDNFCDFEIQYEIAHNY
IHALVGGAQPYGMASLRYTAFDPLFYLHHSNTDRIWAIWQALQKYRG
KPYNVANCAVTSMREPLQPFGLSANINTDHVTKEHSVPENVEDYKTN
ENYEYDTLEENGLSISQLNKKLEAIKSQDREEAGFLLSGFKKSSLVK
FNICTDSSNCHPAGEFYLLGDENEMPWAYDRVEKYDITEKLHDLKLH
AEDHFYIDYEVFDLKPASLGKDLFKQPSVIHEPRIGHHEGEVYQAEV
TSANRIRKNIENLSLGELESLRAAFLEIENDGTYESIAKEEIGSPGL
CQLNGNPISCCVHGMPTTPHWHRLYVVVVENALLKKGSSVAVPYWDW
TKRIEHLPHLISDATYYNSRQHHYETNPFHHGKITHENEITTRDPKD
SLFHSDYFYEQVLYALEQDNFCDFEIQLEILHNALHSLLGGKGKYSM
SNLDYAAFDPVFELHHATTDRIWAIWQDLQRERKRPYREANCAIQLM
HTPLQPEDKSDNNDEATKTHATPHDGFEYQNSFGYAYDNLELNHYSI
PQLDHMLQERKRHDRVEAGELLHNIGTSADGHVFVCLPTGEHTKDCS
HEAGMFSILGGQTEMSFVFDRLYKLDITKALKKNGVHLQGDFDLEIE
ITAVNGSHLDSHVIHSPTILFEAGTDSAHTDDGHTEPVMIRKDITQL
DKRQQLSLVKALESMKADHSSDGFQAIASFHALPPLCPSPAASKRFA
CCVHGMATFPQWHRLYTVQFQDSLRKHGAVVGLPYWDWTLPRSELPE
LLTVSTIHDPETGRDIPNPFIGSKIEFEGENVHTKRDINRDRLFQGS
TKTHHNWFIEQALLALEQTNYCDFEVQFEEVIHNGVHTWVGGKEPYG
IGHLHYASYDPLFYIHHSQTDRIWAIWQSLQRFRGLSGSEANCAVNL

-continued

MKTPLKPFSFGAPYNLNDHTHDFSKPEDTFDYQKFGYIYDTLEFAGW
SIRGIDHIVRNRQEHSRVFAGFLLEGFGTSATVDFQVCRTAGDCEDA
GYFTVLGGEKEMPWAFDRLYKYDITETLDKMNLRHDEIFQIEVTITS
YDGTVLDSGLIPTPSIIYDPAHHDISSHHLSLNKVRHDLSTLSERDI
GSLKYALSSLQADTSADGFAAIASFHGLPAKCNDSHNNEVACCIHGM
PTFPHWHRLYTLQFEQALRRHGSSVAVPYWDWTKPIHNIPHLFTDKE
YYDVWRNKVMPNPFARGYVPSHDTYTVRDVQEGLFHLTSTGEHSALL
NQALLALEQHDYCDFAVQFEVMHNTIHYLVGGPQVYSLSSLHYASYD
PIFFIHHSFVDKVWAVWQALQEKRGLPSDRADCAVSLMTQNMRPFHY
EINHNQFTKKHAVPNDVFKYELLGYRYDNLEIGGMNLHEIEKEIKDK
QHHVRVFAGFLLHGIRTSADVQFQICKTSEDCHHGGQIFVLGGTKEM
AWAYNRLFKYDITHALHDAHITPEDVFHPSEPFFIKVSVTAVNGTVL
PASILHAPTIIYEPGLDHHEDHHSSSMAGHGVRKEINTLTTAEVDNL
KDAMRAVMADHGPNGYQAIAAFHGNPPMCPMPDGKNYSCCTHGMATF
PHWHRLYTKQMEDALTAHGARVGLPYWDGTTAFTALPTFVTDEEDNP
FHHGHIDYLGVDTTRSPRDKLFNDPERGSESFFYRQVLLALEQTDFC
QFEVQFEITHNAIHSWTGGLTPYGMSTLEYTTYDPLFWLHHANTDRI
WAIWQALQEYRGLPYDHANCEIQAMKRPLRPFSDPINHNAFTHSNAK
PTDVFEYSRFNFQYDNLRFHGMTIKKLEHELEKQKEEDRTFAAFLLH
GIKKSADVSFDVCNHDGECHFAGTFAILGGEHEMPWSFDRLFRYDIT
QVLKQMHLEYDSDFTFHMRIIDTSGKQLPSDLIKMPTVEHSPGGKHH
EKHHEDHHEDILVRKNIHSLSHHEAEELRDALYKLQNDESHGGYEHI
AGFHGYPNLCPEKGDEKYPCCVHGMSIFPHWHRLHTIQFERALKKHG
SHLGIPYWDWTQTISSLPTFFADSGNNNPFFKYHIRSINQDTVRDVN
EAIFQQTKFGEFSSIFYLALQALEEDNYCDFEVQYEILHNEVHALIG
GAEKYSMSTLEYSAFDPYFMIHHASLD

Discussion

Hypersecretion of human amylin is associated with amylin deposition in the microvasculature and RBCs leading to impaired RBC-capillary interaction and activation of hypoxia signaling pathways. Impairment of tissue oxygen-sensing found in diabetic HIP rats was mirrored in control rats that were given amylin-coated RBCs intravenously and in diabetic UCD rats that were given human amylin intravenously. These results indicate that amylin-coated RBCs are a trigger of hypoxia signaling pathways. These deleterious effects result in part from a reduced flux of amylin-coated RBCs through the capillaries that may involve adhesion proteins. Blocking the expression of adhesion proteins in the vascular endothelium by upregulation of EETs reduces amylin dyshomeostasis and HIF activation.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Go A S, Mozaffarian D, Roger V L, et al. American Heart Association Statistics Committee and Stroke Statistics Subcommittee. Heart disease and stroke statistics-2013 update: a report from the American Heart Association. Circulation. 2013; 127:e6-e245
2. Schulze P C, Drosatos K, Goldberg I J. Lipid Use and Misuse by the Heart. Circ Res. 2016; 118(11):1736-51
3. Gutterman D D. Silent myocardial ischemia. Circ J. 2009 73(5):785-97
4. Riehle C, Abel E D. Insulin Signaling and Heart Failure. Circ Res. 2016; 118(7):1151-69
5. Taegtmeyer H., P. McNulty, M. E. Young, Adaptation and maladaptation of the heart in diabetes: Part I: general concepts, Circulation. 105 (2002) 1727-1733.
6. Despa S, Margulies K B, Chen L, Knowlton A A, Havel P J, Taegtmeyer H, Bers D M, Despa F. Hyperamylinemia contributes to heart dysfunction in obesity and diabetes, a study in humans and rats. Circ Res. 110:598-608 (2012).
7. Despa S, Despa S, Sharma S, T R Harris, H Dong, N Li, N Chiamvimonvat, H Taegtmeyer, K Margulies, B D Hammock and F Despa, Cardioprotection by controlling hyperamylinemia in a "humanized" diabetic rat model. J Am Heart Assoc 2014; 3(4):e001015
8. Liu M, Verma N, Peng X, Srodulski S, Morris A, Chow M, Hersh L B, Chen J, Zhu H, Netea M, Margulies K B, Despa S and Despa F. Hyperamylinemia increases IL-1β synthesis in the heart via peroxidative sarcolemmal injury. Diabetes 2016; 65, 2772-83
9. Ilaiwy A, Liu M, del Monte F, Parry T L, Bain J R, Newgard C B, Schisler J C, Muehlbauer M J, Despa F, Willis M S. Human amylin proteotoxicity impairs protein biosynthesis, and alters major cellular signaling pathways in the heart, brain and liver of humanized diabetic rat model in vivo. Metabolomics 2016; 12, 1-14
10. Liu M, Hoskins A, Verma N, Bers D M, Despa S, and Despa F. Amylin and Diabetic Cardiomyopathy—Amylin-Induced Sarcolemmal $Ca^{2+}$ Leak Is Independent of Diabetic Remodeling of Myocardium. BBA-Mol Basis Dis. DOI: 10.1016/j.bbadis.2017.10.024
11. Jurgens C A, Toukatly M N, Fligner C L, Udayasankar J, Subramanian S L, Zraika S, Aston-Mourney K, Carr D B, Westermark P, Westermark G T, Kahn S E, Hull R L: β-cell loss and β-cell apoptosis in human type 2 diabetes are related to islet amyloid deposition. Am J Pathol 2011, 178(6):2632-2640.
12. Höppener J W M, Ahren B, Lips C J M: Islet amyloid and type 2 diabetes mellitus. N Engl J Med 2000, 343 (6):411-419.
13. Gurlo T, S Ryazantsev, CJ Huang, MW Yeh, HA Reber, O J Hines, T D O'Brien, C G Glabe, PC Butler, Evidence for proteotoxicity in beta cells in type 2 diabetes: toxic islet amyloid polypeptide oligomers form intracellularly in the secretory pathway. Am J Pathol 176, 861-869 (2010).
14. Guan H, Chow C M, Song E S, Verma N, Despa F, Hersh L B, The role of intramitochondrial islet amyloid polypeptide in beta-cell loss and its regulation by the mitochondrial peptidase pitrilysin. PLoS One. 2015; 10(7): e0133263
15. Jackson K, Barisone G A, Diaz E, Jin L-W, DeCarli C, and Despa F. Amyloid deposition in the brain: a second amyloid in Alzheimer's disease? Ann Neurol 2013; 74: 517-26
16. Srodulski S., S. Savita, A. B. Bachstetter, J. M. Brelsford, C. Pascual, X. S. Xie, K. E. Saatman, L. J. Van Eldik, F. Despa, Neuroinflammation and neurologic deficits in diabetes linked to brain accumulation of amylin. Mol Neurodegener. 9 (2014) 30
17. Verma N., H. Ly, M. Liu, J. Chen, H. Zhu, M. Chow, L. B. Hersh, F. Despa, Intraneuronal amylin deposition, peroxidative membrane injury and increased IL-1beta synthesis in brains of Alzheimer's disease patients with type-2 diabetes and in diabetic HIP rats. J Alzheimers Dis. 53 (2016) 259-272.
18. Ly H., N. Verma, F. Wu, M. Liu, K. E. Saatman, P. T. Nelson, J. T. Slevin, L. B. Goldstein, G. J. Biessels, F. Despa, Brain microvascular injury and white matter disease provoked by diabetes-associated hyperamylinemia. Ann Neurol. 82 (2017) 208-222
19. Fawver J. N., Y. Ghiwot, C. Koola, W. Carrera, J. Rodriguez-Rivera, C. Hernandez, K. T. Dineley, Y. Kong, J. Li, J. Jhamandas, G. Perry, I.V. Murray, Islet amyloid polypeptide (IAPP): a second amyloid in Alzheimer's disease. Curr Alzheimer Res. 11 (2014) 928-940
20. Oskarsson M. E., J. F. Paulsson, S. W. Schultz, M. Ingelsson, P. Westermark, G. T. Westermark, In vivo seeding and cross-seeding of localized amyloidosis: A molecular link between type 2 diabetes and Alzheimer disease. Am J Pathol. 185 (2015) 834-846.
21. Schultz N., E. Byman, M. Fex, M. Wennström, Amylin alters human brain pericyte viability and NG2 expression. J Cereb Blood Flow Metab. 37 (2017) 1470-1482
22. Gong W, Z H Liu, C H Zeng, A Peng, HP Chen, H Zhou and LS Li. Amylin deposition in the kidney of patients with diabetic nephropathy, Kidney International 72:213-218 (2007)
23. Westermark P, Andersson A, Westermark G T. Islet amyloid polypeptide, islet amyloid, and diabetes mellitus. Physiol Rev. 91:795-826 (2011)
24. Westermark P, Engström U, Johnson K H, Westermark G T, Betsholtz C. Islet amyloid polypeptide: pinpointing amino acid residues linked to amyloid fibril formation. Proc. Natl. Acad. Sci. USA. 87:50365040 (1990)
25. Erickson J R, Pereira L, Wang L, Han G, Ferguson A, Dao K, Copeland R J, Despa F, Hart G W, Ripplinger C M, and Bers D M, Diabetic Hyperglycemia activates CaMKII and Arrhythmias by O linked Glycosylation. Nature. 2013; 502:372-6
26. Lambert R, S Srodulski, X Peng, KB Margulies, F Despa, S Despa. [$Na^+$]i is Elevated in Diabetic Hearts Due to Enhanced $Na^+$-Glucose Cotransport. J Am Heart Assoc 2015, 4(9):e002183.
27. Gebre-Medhin S., H. Mulder, M. Pekny, G. Westermark, J. Törnell, P. Westermark, F. Sundler, B. Ahrén, C. Betsholtz, Increased insulin secretion and glucose tolerance in mice lacking islet amyloid polypeptide (amylin). Biochem Biophys Res Commun. 250 (1998) 271-277.
28. Baldo B. A., A. E. Kelley, Amylin infusion into rat nucleus accumbens potently depresses motor activity and ingestive behavior. Am J Physiol Regul Integr Comp Physiol. 281 (2001) R1232-R1242
29. Enoki S. Mitsukawa T, Takemura J, Nakazato M, Aburaya J, Toshimori H, Matsukara S. Plasma islet amyloid polypeptide levels in obesity, impaired glucose tolerance and non-insulin-dependent diabetes mellitus. Diabetes Res Clin Pract. 15:97-102 (1992).
30. Johnson K H, TD O'Brien, K Jordan P Westermark, Impaired glucose tolerance is associated with increased islet amyloid polypeptide (IAPP) immunoreactivity in pancreatic beta cells. Am. J. Pathol. 135, 245-250 (1989).
31. Paulsson J F, Ludvigsson J, Carlsson A, Casas R, Forsander G, Ivarsson S A, Kockum I, Lernmark Å, 31. Marcus C, Lindblad B, Westermark G T. High plasma levels of islet amyloid polypeptide in young with new-onset of type 1 diabetes mellitus. PLoS One. 2014; 9(3):e93053
32. Matveyenko A. V., P. C. Butler, □-cell deficit due to increased apoptosis in the human islet amyloid polypeptide transgenic (HIP) rat recapitulates the metabolic defects present in type-2 diabetes. Diabetes. 55 (2006) 2106-2114.
33. Zraika S., R. L. Hull, J. Udayasankar, K. Aston-Mourney, S. L. Subramanian, R. Kisilevsky, W. A. Szarek, S. E. Kahn, Oxidative stress is induced by islet amyloid formation and time-dependently mediates amyloid-induced beta cell apoptosis. Diabetologia. 52 (2009) 626-35.
34. Janciauskiene S., B. Ahrén, Fibrillar islet amyloid polypeptide differentially affects oxidative mechanisms and lipoprotein uptake in correlation with cytotoxicity in two insulin-producing cell lines. Biochem Biophys Res Commun. 267:2 (2000) 619-625.
35. Westwell-Roper C., D. L. Dai, G. Soukhatcheva, K. J. Potter, N. van Rooijen, J. A. Ehses, C. B. Verchere, IL-1 blockade attenuates islet amyloid polypeptide-induced proinflammatory cytokine release and pancreatic islet graft dysfunction. J Immunol. 187 (2011) 2755-2765.
36. Masters S. L., A. Dunne, S. L. Subramanian, R. L. Hull, G. M. Tannahill, F. A. Sharp, C. Becker, L. Franchi, E. Yoshihara, Z. Chen, N. Mullooly, L. A. Mielke, J. Harris, R. C. Coll, K. H. Mills, K. H. Mok, P. Newsholme, G. Nunez, J. Yodoi, S. E. Kahn, E. C. Lavelle, L. A. O'Neill, Activation of the NLRP3 inflammasome by islet amyloid polypeptide provides a mechanism for enhanced IL-1beta in type 2 diabetes. Nat Immunol. 11 (2010) 897-904.
37. Moreno-Gonzalez I, Edwards 3rd G, Salvadores N, et al. Molecular interaction between type 2 diabetes and Alzheimer's disease through cross-seeding of protein misfolding. Mol Psychiatry 2017; 22(9):13271334
38. Matveyenko A. V., P. C. Butler, Islet amyloid polypeptide (IAPP) transgenic rodents as models for Type 2 Diabetes. ILAR Journal. 47 (2006) 225-233.
39. Huang C. J., L. Haataja, T. Gurlo, A. E. Butler, X. Wu, W. C. Soeller, P. C. Butler, Induction of endoplasmic reticulum stress-induced beta-cell apoptosis and accumulation of polyubiquitinated proteins by human islet amyloid polypeptide. Am J Physiol Endocrinol Metab. 293 (2007) E1656-E1662.
40. Kahn S E, D'Alessio D A, Schwartz M W, Fujimoto W Y, Ensinck J W, Taborsky G J Jr, Porte D Jr. Evidence of cosecretion of islet amyloid polypeptide and insulin by beta-cells. Diabetes 1990, 39(5):634-638.
41. Juhan I, Vague P, Buonocore M, Moulin J P, Jouve R, Vialettes B. Abnormalities of erythrocyte deformability and platelet aggregation in insulin-dependent diabetics corrected by insulin in vivo and in vitro. Lancet. 1982; 1(8271):535-7
42. Kim M, Alapan Y, Adhikari A, Little J A, Gurkan U A. Hypoxia-enhanced adhesion of red blood cells in microscale flow. Microcirculation. 2017 July; 24(5).
43. Crawford J H, Isbell T S, Huang Z, Shiva S, Chacko B K, Schechter A N, Darley-Usmar V M, Kerby J D, Lang J D Jr, Kraus D, Ho C, Gladwin M T, Patel R P. Hypoxia, red blood cells, and nitrite regulate NO-dependent hypoxic vasodilation. Blood. 2006; 107(2):566-74.
44. Pittman R N. Oxygen transport in the microcirculation and its regulation. Microcirculation. 2013; 20(2): 11737
45. Imig J D. Epoxides and soluble epoxide hydrolase in cardiovascular physiology. Physiol Rev 2012; 92: 101-30.
46. Imig J D. Epoxyeicosatrienoic Acids and 20-Hydroxyeicosatetraenoic Acid on Endothelial and Vascular Function. Adv Pharmacol. 2016; 77: 105-141
47. Yang L, Mäki-Petäjä K, Cheriyan J, McEniery C, Wilkinson I B. The role of epoxyeicosatrienoic acids in the cardiovascular system. Br J Clin Pharmacol. 2015; 80(1):28-44
48. Fitzpatrick F A, Ennis M D, Baze M E, Wynalda M A, McGee J E, Liggett W F. Inhibition of cyclooxygenase activity and platelet aggregation by epoxyeicosatrienoic acids. J Biol Chem. 261: 15334-15338 (1986).
49. Spector A A, Fang X, Snyder G D, Weintraub N L. Epoxyeicosatrienoic acids (EETs): metabolism and biochemical function. Prog Lipid Res 43: 55-90 (2004).
50. American Diabetes Association. Standards of medical care in diabetes-2015. Diabetes Care. 2015; 38:S1-S89
51. Zhao H. L., Y. Sui, J. Guan, L. He, F. M. Lai, D. R. Zhong, D. Yang, L. Baum, P. C. Tong, B. Tomlinson, J. C. Chan, Higher islet amyloid load in men than in women with type 2 diabetes mellitus. Pancreas. 37 (2008) e6873
52. Kahn S. E., R. L. Prigeon, D. K. McCulloch, E. J. Boyko, R. N. Bergman, M. W. Schwartz, J. L. Neifing, W. K. Ward, J. C. Beard, J. P. Palmer, Quantification of the relationship between insulin sensitivity and beta-cell function in human subjects. Evidence for a hyperbolic function. Diabetes. 42 (1993) 1663-1672.
53. Geer E. B., W. Shen, Gender differences in insulin resistance, body composition, and energy balance. Gend Med. 6 (2009) 60-75.
54. Zhu Y., X. Ai, R. A. Oster, D. M. Bers, S. M. Pogwizd, Sex differences in repolarization and slow delayed rectifier potassium current and their regulation by sympathetic stimulation in rabbits. Pflugers Arch. 465 (2013) 805-818.
55. Yan S., Y. Chen, M. Dong, W. Song, S. M. Belcher, H. S. Wang, Bisphenol A and 17β-estradiol promote arrhythmia in the female heart via alteration of calcium handling. PLoS One. 6 (2011) e25455.
56. Stauffer B. L., R. D. Sobus, C. C. Sucharov, Sex differences in cardiomyocyte connexin43 expression. J Cardiovasc Pharmacol. 58 (2011) 32-39.
57. Baraj as-Martinez H., V. Haufe, C. Chamberland, M. J. Roy, M. H. Fecteau, J. M. Cordeiro, R. Dumaine, Larger dispersion of INa in female dog ventricle as a mechanism for gender-specific incidence of cardiac arrhythmias. Cardiovasc Res. 81 (2009) 82-89.
58. Sims C., S. Reisenweber, P. C. Viswanathan, B. R. Choi, W. H. Walker, G. Salama, Sex, age, and regional differences in L-type calcium current are important determinants of arrhythmia phenotype in rabbit hearts with drug-induced long QT type 2. Circ Res. 102 (2008) e86-e100.
59. Farrell S. R., J. L. Ross, S. E. Howlett, Sex differences in mechanisms of cardiac excitation-contraction coupling in rat ventricular myocytes. Am J Physiol Heart Circ Physiol. 299 (2010) H36-H45.
60. Wasserstrom J. A., S. Kapur, S. Jones, T. Faruque, R. Sharma, J. E. Kelly, A. Pappa, W. Ho, A. H. Kadish, G. L. Aistrup, Characteristics of intracellular Ca2+ cycling in intact rat heart: a comparison of sex differences. Am J Physiol Heart Circ Physiol. 295 (2008) H1895-H1904.
61. Lagranha C. J., A. Deschamps, A. Aponte, C. Steenbergen, E. Murphy, Sex differences in the phosphorylation of mitochondrial proteins result in reduced production of reactive oxygen species and cardioprotection in females. Circ Res. 106 (2010) 1681-1691.
62. Wang F., Q. He, Y. Sun, X. Dai, X. P. Yang, Female adult mouse cardiomyocytes are protected against oxidative stress. Hypertension. 55 (2010) 1172-1178.

63. S. Trikha, A. M. Jeremic, Distinct internalization pathways of human amylin monomers and its cytotoxic oligomers in pancreatic cells. PLoS One. 8 (2013) e73080.
64. J. H. Jhamandas, D. MacTavish, Antagonist of the amylin receptor blocks beta-amyloid toxicity in rat cholinergic basal forebrain neurons. J. Neurosci. 24 (2004) 5579-5584.
65. D. Bell, K. D. Schlüter, X. J. Zhou, B. J. McDermott, H. M. Piper, Hypertrophic effects of calcitonin gene-related peptide (CGRP) and amylin on adult mammalian ventricular cardiomyocytes. J Mol Cell Cardiol. 27 (1995) 2433-2443.
66. Lee R C, Despa F, Tang X, Titushkin I, Cho M. Direct observations of the P188 mediated membrane sealing with atomic force microscopy. Molecular & Cellular Biomechanics, 3 185-186 (2006).
67. Collins J M, F Despa and R C. Lee Structural and Functional Recovery of Electropermeabilized Skeletal Muscle in-vivo after Treatment with Surfactant Poloxamer 188 Biochim. Biophys. Acta, 1768 1238-1246 (2007).
68. Townsend D, Turner I, Yasuda S, Martindale J, Davis J, Shillingford M, Kornegay J N, Metzger J M. (2010). Chronic administration of membrane sealant prevents severe cardiac injury and ventricular dilatation in dystrophic dogs. J Clin Invest. 120:1140-50 (2010)
69. Janson J, Ashley R H, Harrison D, McIntyre S, Butler P C. The mechanism of islet amyloid polypeptide toxicity is membrane disruption by intermediate-sized toxic amyloid particles. Diabetes 48:491-498 (1999).
70. Anguiano M, Nowak R J, Lansbury P T, Jr. Protofibrillar islet amyloid polypeptide permeabilizes synthetic vesicles by a pore-like mechanism that may be relevant to type II diabetes. Biochemistry 41:11338-11343 (2002)
71. Srodulski S., A. Loria, S. Despa, F. Despa, Hyperamylinemia, a potential therapeutic target in diabetic cardiorenal syndrome. Circulation. 130 (2013) A13963.
72. Hu R, Zhang M, Patel K, et al. Cross-sequence interactions between human and rat islet amyloid polypeptides. Langmuir 2014; 30:5193-5201
73. Scholz H, Schurek H J, Eckardt K U, Bauer C. Role of erythropoietin in adaptation to hypoxia. Experientia. 1990; 46(11-12):1197-201
74. Invention Report (record UKRF No. 2182)—Diagnosis of Diabetes by Detecting Aggregated Amylin in Erythrocytes.
75. Huang Y, Hickey R P, Yeh J L, Liu D, Dadak A, Young L H, Johnson R S, Giordano F J. Cardiac myocyte-specific HIF-1alpha deletion alters vascularization, energy availability, calcium flux, and contractility in the normoxic heart. FASEB J. 2004; 18(10):1138-40.
76. Lee S H, Wolf P L, Escudero R, Deutsch R, Jamieson S W, Thistlethwaite P A. Early expression of angiogenesis factors in acute myocardial ischemia and infarction. N Engl J Med. 2000; 342(9):626-33
77. Park S K, Dadak A M, Haase V H, Fontana L, Giaccia A J, Johnson R S. Hypoxia-induced gene expression occurs solely through the action of hypoxia-inducible factor 1alpha (HIF-1alpha): role of cytoplasmic trapping of HIF-2alpha. Mol Cell Biol. 2000; 23(14):4959-71.
78. Ashmore T, B O Fernandez, C Branco-Price, J A West, A S Cowburn, LC Heather, J L Griffin, R S Johnson, M Feelisch, A J Murray. Dietary nitrate increases arginine availability and protects mitochondrial complex I and energetics in the hypoxic rat heart. J Physiol. 592:4715-31, 2014
79. Popescu I, Galice S, Mohler P J, Despa S. Elevated local [$Ca^{2+}$] and CaMKII promote spontaneous $Ca^{2+}$ release in ankyrin-B-deficient hearts. Cardiovasc Res. 2016; 111: 287-294.
80. Bers D M. Cardiac sarcoplasmic reticulum calcium leak: basis and roles in cardiac dysfunction. Annu Rev Physiol. 2014; 76:107-127
81. Luo M., X. Guan, E. D. Luczak, D. Lang, W. Kutschke, Z. Gao, J. Yang, P. Glynn, S. Sossalla, P. D. Swaminathan, R. M. Weiss, B. Yang, A. G. Rokita, L. S. Maier, I. R. Efimov, T. J. Hund, M. E. Anderson. Diabetes increases mortality after myocardial infarction by oxidizing CaMKII. J Clin Invest. 123 (2013) 1262-1274.
82. Bovo E., S. L. Lipsius, A. V. Zima, Reactive oxygen species contribute to the development of arrhythmogenic $Ca^{2+}$ waves during 3-adrenergic receptor stimulation in rabbit cardiomyocytes. J Physiol. 590 (2012) 3291-3304.
83. Guglielmino, K Jackson, TR. Harris, V Vu, G Dutrow, J E Evans, J Graham, BP Cummings, P J Havel, N Chiamvimonvat, S Despa, B D Hammock, F Despa. Pharmacological inhibition of soluble epoxide hydrolase preserves cardiac myocyte structure and function in hyperglycemic rats. Am J Physiol Heart Circ Physiol. 303 H853-862 (2012)
84. Yasuda S, Townsend D, Michele D E, Farve E G, Day S M, Metzger J. Dystrophic heart failure blocked by membrane sealant poloxamer. Nature 2005; 436:1025-1029.
85. Mina E W, Lasagna-Reeves C, Glabe C G, Kayed R. Poloxamer 188 copolymer membrane sealant rescues toxicity of amyloid oligomers in vitro. J Mol Biol. 391: 577-85 (2009).
86. Gebre-Medhin S., H. Mulder, M. Pekny, G. Westermark, J. Törnell, P. Westermark, F. Sundler, B. Ahrén, C. Betsholtz, Increased insulin secretion and glucose tolerance in mice lacking islet amyloid polypeptide (amylin). Biochem Biophys Res Commun. 250 (1998) 271-277.
87. Bovo E, Lipsius S L, Zima A V. Reactive oxygen species contribute to the development of arrhythmogenic $Ca^{2+}$ waves during 3-adrenergic receptor stimulation in rabbit cardiomyocytes. J Physiol. 2012; 590:32913304.
88. Gomes A, Fernandes E, Lima J L. Fluorescence probes used for detection of reactive oxygen species. J Biochem Biophys Methods. 2005 65:45-80.
89. T Ashmore, B O Fernandez, C Branco-Price, J A West, A S Cowburn, LC Heather, J L Griffin, R S Johnson, M Feelisch, A J Murray. Dietary nitrate increases arginine availability and protects mitochondrial complex I and energetics in the hypoxic rat heart. J Physiol. 592:4715-31, 2014
90. T Ashmore, L D Roberts, A J Morash, A O Kotwica, J Finnerty, J A West, S A Murfitt, B O Fernandez, C Branco, A S Cowburn, K Clarke, R S Johnson, M Feelisch, J L Griffin, A J Murray. Nitrate enhances skeletal muscle fatty acid oxidation via a nitric oxide-cGMP-PPAR-mediated mechanism. BMC Biol. 13:110, 2015
91. L D Roberts, T Ashmore, B D McNally, S A Murfitt, B O Fernandez, M Feelisch, R Lindsay, M Siervo, EA Williams, A J Murray, J L Griffin. Inorganic nitrate mimics exercise-stimulated muscular fiber-type switching and myokine and γ-aminobutyric acid release. Diabetes. 66:674-688, 2017
92. L D Roberts, T Ashmore, A O Kotwica, S A Murfitt, B O Fernandez, M Feelisch, A J Murray, J L Griffin. Inorganic Nitrate Promotes the Browning of White Adipose Tissue through the Nitrate-Nitrite-Nitric Oxide Pathway. Diabetes. 64:471-84, 2014

93. Beckman J A, Creager M A. Vascular Complications of Diabetes. Circ Res. 2016; 118:1771-1785.
94. Rittenhouse J B, T Chait, J R Bierle, SM Janes, DR Park, J L Phelps, M S Fineman, J Qin, and J E Koda. Heterogeneity of naturally occurring human amylin due to glycosylation. Diabetes 45, Suppl. 2: 235A, 1996
95. Kapurniotu A, Bernhagen J, Greenfield N, Al-Abed Y, Teichberg S, Frank R W, Voelter W, Bucala R. Contribution of advanced glycosylation to the amyloidogenicity of islet amyloid polypeptide. Eur J Biochem. 1998 251(1-2):208-16
96. Leighton B, Cooper G J S: Pancreatic amylin and calcitonin gene-related peptide causes resistance to insulin in skeletal muscle in vitro. Nature 1988, 355(6191): 632-635.
97. Zierath J R, Galuska D, Engstrom A, Johnson K H, Betsholtz C, Westermark P, Wallberg-Henriksson H: Human islet amyloid polypeptide at pharmacological levels inhibits insulin and phorbol ester-stimulated glucose transport in in vitro incubated human muscle strips. Diabetologia 35:26-31,1992
98. Molina J M, Cooper G J S, Leighton B, Olefsky J M: Induction of insulin resistance in vivo by amylin and calcitonin gene-related peptide. Diabetes 1990, 39(2): 260-265.
99. Cooper G J S, Leighton B, Dimitriadis G D, Parry-Billings M, Kowalchuck J M, Howland K, Rothbard J B, Willis A C, Reid K B M: Amylin found in amyloid deposits in human type 2 diabetes mellitus may be a hormone that regulates glycogen metabolism in skeletal muscle. Proc Natl Acad Sci USA 1988, 85(20):7763-7776.
100. Degano P, Silvestre R A, Salas M, Peiro E, Marco J: Amylin inhibits glucose-induced insulin secretion in a dose-dependent manner: study in the perfused rat pancreas. Regul Pept 43:91-96, 1993
101. Silvestre R A, Peiro E, Degano P, Miralles P, Marco J: Inhibitory effect of rat amylin on the insulin responses to glucose and arginine in the perfused rat pancreas. Regul Pept 31:23-31, 1990
102. Rask-Madsen C, King G L. Mechanisms of Disease: endothelial dysfunction in insulin resistance and diabetes. Nat Clin Pract Endocrinol Metab. 2007; 3:46-56
103. Fleming I. Epoxyeicosatrienoic acids, cell signaling and angiogenesis. Prostaglandins & Other Lipid Mediators. 2007; 82:60-67.
104. Semenza G L. Life with oxygen. Science. 2007; 318:62-64.
105. Mohandas N, Gallagher P G. Red cell membrane: past, present, and future. Blood. 2008; 112:3939-3948.
106. McMillan D E, Utterback N G, La Puma J. Reduced erythrocyte deformability in diabetes. Diabetes. 1978; 27: 895-901.
107. Tonelli M, Sacks F, Arnold M, et al. Relation between Red Blood Cell Distribution Width and Cardiovascular Event Rate in People with Coronary Disease. Circulation. 2008; 117:163-168.
108. Thomas M C. Anemia in diabetes: marker or mediator of microvascular disease? Nat. Clin. Pract. Nephrol. 2007; 3:20-30.
109. Maddox T M, Stanislawski M A, Grunwald G K, et al. Nonobstructive coronary artery disease and risk of myocardial infarction. JAMA. 2014; 312:1754-1763.
110. Barrett E J, Liu Z, Khamaisi M, et al. Diabetic Microvascular Disease: An Endocrine Society Scientific Statement. J Clin Endocrinol Metab. 2017; 102:4343-4410.
111. Semenza G L. Involvement of oxygen-sensing pathways in physiologic and pathologic erythropoiesis. Blood. 2009; 114:2015-2019.
112. Samanta D, Prabhakar N R, Semenza G L. Systems biology of oxygen homeostasis. Wiley Interdiscip. Rev. Syst. Biol. Med. 2017; 9: e1382.
113. Wong B W, Marsch E, Treps L, et al. Endothelial cell metabolism in health and disease: impact of hypoxia. EMBO J. 2017; 36:2187-2203.
114. Gerstein H C, Bosch J, Dagenais G R, et al. ORIGIN Trial Investigators. Basal insulin and cardiovascular and other outcomes in dysglycemia. N Engl J Med. 2012; 367:319-328.
115. Dankner R, Chetrit A, Shanik M H, et al. Basal state hyperinsulinemia in healthy normoglycemic adults heralds dysglycemia after more than two decades of follow up. Diabetes. Metab. Res. Rev. 2012; 28:618-624.
116. Butler P C, Chou J, Carter W B, et al. Effects of meal ingestion on plasma amylin concentration in NIDDM and nondiabetic humans. Diabetes. 1990; 39:752-756.
117. Westermark P, Andersson A, Westermark G T. Islet amyloid polypeptide, islet amyloid, and diabetes mellitus. Physiol. Rev. 2011; 91:795-826.
118. Kahn S E, D'Alessio D A, Schwartz M W, et al. Evidence of cosecretion of islet amyloid polypeptide and insulin by beta-cells. Diabetes. 1990; 39:634-638.
119. Lutz T A. The role of amylin in the control of energy homeostasis. Am. J. Physiol. Regul. Integr. Comp. Physiol. 2010; 298:R1475-R1484.
120. Westermark P, Engstrom U, Johnson K H, et al. Islet amyloid polypeptide: pinpointing amino acid residues linked to amyloid fibril formation. Proc. Natl. Acad. Sci. USA. 1990; 87:5036-5040.
121. Janson J, Ashley R H, Harrison D, et al. The mechanism of islet amyloid polypeptide toxicity is membrane disruption by intermediate-sized toxic amyloid particles. Diabetes. 1999; 48:491-498.
122. Zraika S1, Hull R L, Udayasankar J, et al. Oxidative stress is induced by islet amyloid formation and time-dependently mediates amyloid-induced beta cell apoptosis. Diabetologia. 2009; 52:626-635.
123. Huang C J, Haataja L, Gurlo T, et al. Induction of endoplasmic reticulum stress-induced beta-cell apoptosis and accumulation of polyubiquitinated proteins by human islet amyloid polypeptide. Am. J. Physiol. Endocrinol. Metab. 2007; 293:E1656-E1662.
124. Despa S, Margulies K B, Chen L, et al. Hyperamylinemia contributes to cardiac dysfunction in obesity and diabetes: A study in humans and rats. Circ. Res. 2012; 110:598-608
125. Despa S, Sharma S, Harris T R, et al. Cardioprotection by controlling hyperamylinemia in a "humanized" diabetic rat model. J. Am. Heart. Assoc. 2014; 3:pii: e001015.
126. Liu M, Verma N, Peng X, et al. Hyperamylinemia increases IL-1β synthesis in the heart via peroxidative sarcolemmal injury. Diabetes. 2016; 65:2772-2783.
127. Jackson K, Barisone G A, Diaz E, et al. Amylin deposition in the brain: A second amyloid in Alzheimer disease? Ann. Neurol. 2013; 74:517-526.
128. Verma N, Ly H, Liu M, et al. Intraneuronal amylin deposition, peroxidative membrane injury and increased IL-1β synthesis in brains of Alzheimer's disease patients with type-2 diabetes and in diabetic HIP rats. J. Alzheimers. Dis. 2016; 53:259-272.

129. Ly H, Verma N, Wu F, et al. Brain microvascular injury and white matter disease provoked by diabetes-associated hyperamylinemia. Ann. Neurol. 2017; 82:208-222.

130. Gong W, Liu Z H, Zeng C H, et al. Amylin deposition in the kidney of patients with diabetic nephropathy. Kidney Int. 2007; 72:213-218.

131. Fawver J N, Ghiwot Y, Koola C, et al. Islet amyloid polypeptide (IAPP): A second amyloid in Alzheimer's disease. Curr. Alzheimer. Res. 2014; 1:928-940.

132. Oskarsson M E, Paulsson J F, Schultz S W, et al. In vivo seeding and cross-seeding of localized amyloidosis: A molecular link between type 2 diabetes and Alzheimer disease. Am. J. Pathol. 2015; 185:834-846.

133. Schultz N, Byman E, Fex M, et al. Amylin alters human brain pericyte viability and NG2 expression. J. Cereb. Blood Flow Metab. 2007; 37:1470-1482.

134. Schultz N, Byman E, Netherlands B B, et al. Levels of retinal IAPP are altered in Alzheimer's disease patients and correlate with vascular changes and hippocampal IAPP levels. Neurobiol. Aging. 2018; 69:94-101.

135. Biessels G J, Despa F. Cognitive decline and dementia in diabetes mellitus: mechanisms and clinical implications. Nat. Rev. Endocrinol. 2018; 14:591-604.

136. Butler A E, Jang J, Gurlo T, et al. Diabetes due to a progressive defect in beta-cell mass in rats transgenic for human islet amyloid polypeptide (HIP Rat): a new model for type 2 diabetes. Diabetes. 2004; 53:1509-1516.

137. Srodulski S, Sharma S, Bachstetter A B, et al Neuroinflammation and neurologic deficits in diabetes linked to brain accumulation of amylin. Mol. Neurodegener. 2014; 9:30.

138. Cummings B P, Digitale E K, Stanhope K L, et al. Development and characterization of a novel rat model of type 2 diabetes mellitus: the UC Davis type 2 diabetes mellitus UCD-T2DM rat. Am. J. Physiol. Regul. Integr. Comp. Physiol. 2008; 295:R1782-R1793.

139. Liu M, Hoskins A, Verma N, et al. Amylin and diabetic cardiomyopathy-amylin-induced sarcolemmal Ca2+ leak is independent of diabetic remodeling of myocardium. Biochim. Biophys. Acta. Mol. Basis Dis. 2018; 1864: 1923-1930.

140. Imig J D. Epoxides and soluble epoxide hydrolase in cardiovascular physiology. Physiol Rev. 2012; 92:101-130.

141. Jiang H, Anderson G D, McGiff J C. Red blood cells (RBCs), epoxyeicosatrienoic acids (EETs) and adenosine triphosphate (ATP). Pharmacol Rep. 2010; 62:468-474.

142. Node K, Huo Y, Ruan X, et al. Anti-inflammatory properties of cytochrome P450 epoxygenase-derived eicosanoids. Science. 1999; 285:1276-1279.

143. White J, Lancelot M, Sarnaik S, et al. Increased erythrocyte adhesion to VCAM-1 during pulsatile flow: Application of a microfluidic flow adhesion bioassay. Clin. Hemorheol. Microcirc. 2015; 60:201-13

144. Jain S K, McVie R, Duett J, et al. Erythrocyte membrane lipid peroxidation and glycosylated hemoglobin in diabetes. Diabetes. 1989; 38:1539-1543.

145. Wagner M, Alam A, Zimmermann J, et al. Endogenous erythropoietin and the association with inflammation and mortality in diabetic chronic kidney disease. Clin. J. Am. Soc. Nephrol. 2011 6:1573-1579.

146. Thomas M C. Type 2 Diabetes and Heart Failure: Challenges and Solutions. Curr. Cardiol. Rev. 2016; 12:249-255.

147. Thomas M C, Brownlee M, Susztak K, et al Diabetic kidney disease. Nat. Rev. Dis. Primers. 2015; 1:15018.

148. Peake M, Whiting M. Measurement of serum creatinine-current status and future goals. Clin Biochem Rev. 2006; 27:173-84.

149. Butler A E, Jang J, Gurlo T, et al. Diabetes due to a progressive defect in beta-cell mass in rats transgenic for human islet amyloid polypeptide (HIP Rat): a new model for type 2 diabetes. Diabetes. 2004; 53:1509-1516.

150. Ly H, Verma N, Wu F, et al. Brain microvascular injury and white matter disease provoked by diabetes-associated hyperamylinemia. Ann. Neurol. 2017; 82:208-222.

151. Cummings B P, Digitale E K, Stanhope K L, et al. Development and characterization of a novel rat model of type 2 diabetes mellitus: the UC Davis type 2 diabetes mellitus UCD-T2DM rat. Am. J. Physiol. Regul. Integr. Comp. Physiol. 2008; 295:R1782-1793.

152. Despa S, Sharma S, Harris T R, et al. Cardioprotection by controlling hyperamylinemia in a "humanized" diabetic rat model. J. Am. Heart. Assoc. 2014; 3.

153. Peake M, Whiting M. Measurement of serum creatinine-current status and future goals. Clin Biochem Rev. 2006; 27:173-184.

154. Gordon L. Atkins, James Doyle. A simple method for measuring oxyhemoglobin dissociation curves in a student practical class. Biochemical Education, Volume 7, Issue 2, April 1979, Pages 34-36 Biochemical.

It will be understood that various details of the presently disclosed subject matter can be changed without departing from the scope of the subject matter disclosed herein. Furthermore, the foregoing description is for the purpose of illustration only, and not for the purpose of limitation.

The invention claimed is:

1. A method, comprising:
   a. obtaining a blood sample from a patient;
   b. detecting whether amylin is present in erythrocytes from the blood sample by conducting an amylin enzyme-linked immunosorbent assay (ELISA);
   c. measuring an amount of amylin present in the patient's erythrocytes, wherein the measured amount of amylin in the patient's erythrocytes is higher than a measured amount of amylin in healthy control erythrocytes; and
   d. treating the patient, based on the measured amount of amylin present in the patient's erythrocytes, for amylin related hypoxia by increasing circulating Epoxyeicosatrienoic acids (EETs) in the patient.

2. The method of claim 1, and further comprising:
diagnosing the patient as at risk for developing a comorbidity of type-2 diabetes.

3. The method of claim 2, wherein circulating EETs are increased by administering an effective amount of an inhibitor of Soluble epoxide hydrolase.

4. The method of claim 1, wherein the amylin related hypoxia is renal, cardiac, or brain hypoxia.

5. The method of claim 1, wherein circulating EETs are increased by administering an effective amount of an inhibitor of Soluble epoxide hydrolase.

6. A method, comprising:
a. obtaining a blood sample from a patient;
b. detecting whether amylin is present in erythrocytes from the blood sample by conducting an amylin enzyme-linked immunosorbent assay (ELISA);
c. measuring an amount of amylin present in the patient's erythrocytes, wherein the measured amount of amylin in the erythrocytes of the patient is greater than about 1.2 ng/g total protein and less than about 2 ng/g total protein; and
d. treating the patient, based on the measured amount of amylin in the patient's erythrocytes, for pre-diabetes with lifestyle changes or pharmacological intervention suitable for the treatment of pre-diabetes.

7. The method of claim 6, wherein the treatment increases circulating Epoxyeicosatrienoic acids (EETs) in the patient.

8. The method of claim 6, wherein the lifestyle changes comprises a change in diet, participation in an exercise regimen, or participation in a nutritional program suitable for the treatment of pre-diabetes, or combinations thereof, and
wherein the pharmacological intervention comprises administering insulin, metformin, a sulfonylurea, a meglitinide, a GLP-1 receptor agonist, a DPP-4 inhibitor, a SGLT2 inhibitor, combinations thereof, or an inhibitor of soluble epoxide hydrolase to the patient.

9. A method, comprising:
a. obtaining a blood sample from a patient;
b. detecting whether amylin is present in erythrocytes from the blood sample by conducting an amylin enzyme-linked immunosorbent assay (ELISA);
c. measuring an amount of amylin present in the patient's erythrocytes, wherein the measured amount of amylin in the erythrocytes of the patient is greater than or equal to about 2 ng/g total protein;
d. treating the patient, based on the measured amount of amylin in the patient's erythrocytes, for type-2 diabetes with a therapeutically effective amount of an inhibitor of soluble epoxide hydrolase or an anti-diabetic therapeutic.

10. The method of claim 9, wherein the inhibitor of soluble epoxide hydrolase or the anti-diabetic therapeutic increases circulating Epoxyeicosatrienoic acids (EETs) in the patient.

11. The method of claim 9, wherein the anti-diabetic therapeutic comprises insulin, metformin, a meglitinide, a GLP1 receptor agonist, a DPP-4 inhibitor, an SGLT2 inhibitor, or combinations thereof.

* * * * *

SEQUENCE LISTING

<160> NUMBER OF SEQ ID NOS: 7

<210> SEQ ID NO 1
<211> LENGTH: 3125
<212> TYPE: PRT
<213> ORGANISM: Megathura crenulata

<400> SEQUENCE: 1

```
Leu Ser Val Arg Leu Leu Ile Val Val Leu Ala Leu Ala Asn Ala Glu
1               5                   10                  15

Asn Leu Val Arg Lys Ser Val Glu His Leu Thr Gln Glu Glu Thr Leu
            20                  25                  30

Asp Leu Gln Ala Ala Leu Arg Glu Leu Gln Met Asp Ser Ser Ser Ile
        35                  40                  45
```

```
Gly Phe Gln Lys Ile Ala Ala His Gly Ala Pro Ala Ser Cys Val
 50                  55                  60

His Lys Asp Thr Ser Ile Ala Cys Cys Ile His Gly Met Pro Thr Phe
 65                  70                  75                  80

Pro His Trp His Arg Ala Tyr Val Val His Met Glu Arg Ala Leu Gln
                     85                  90                  95

Thr Lys Arg Arg Thr Ser Gly Leu Pro Tyr Trp Asp Trp Thr Glu Pro
                100                 105                 110

Ile Thr Gln Leu Pro Ser Leu Ala Ala Asp Pro Val Tyr Ile Asp Ser
                115                 120                 125

Gln Gly Gly Lys Ala His Thr Asn Tyr Trp Tyr Arg Gly Asn Ile Asp
                130                 135                 140

Phe Leu Asp Lys Lys Thr Asn Arg Ala Val Asp Asp Arg Leu Phe Glu
145                 150                 155                 160

Lys Val Lys Pro Gly Gln His Thr His Leu Met Glu Ser Val Leu Asp
                165                 170                 175

Ala Leu Glu Gln Asp Glu Phe Cys Lys Phe Glu Ile Gln Phe Glu Leu
                180                 185                 190

Ala His Asn Ala Ile His Tyr Leu Val Gly Gly Lys His Asp Tyr Ser
                195                 200                 205

Met Ala Asn Leu Glu Tyr Thr Ala Tyr Asp Pro Ile Phe Phe Leu His
                210                 215                 220

His Ser Asn Val Asp Arg Ile Phe Ala Ile Trp Gln Arg Leu Gln Glu
225                 230                 235                 240

Leu Arg Asn Lys Asp Pro Lys Ala Met Asp Cys Ala Gln Glu Leu Leu
                245                 250                 255

His Gln Lys Met Glu Pro Phe Ser Trp Glu Asp Asn Asp Ile Pro Leu
                260                 265                 270

Thr Asn Glu His Ser Thr Pro Ala Asp Leu Phe Asp Tyr Cys Glu Leu
                275                 280                 285

His Tyr Asp Tyr Asp Thr Leu Asn Leu Asn Gly Met Thr Pro Glu Glu
                290                 295                 300

Leu Lys Thr Tyr Leu Asp Glu Arg Ser Ser Arg Ala Arg Ala Phe Ala
305                 310                 315                 320

Ser Phe Arg Leu Lys Gly Phe Gly Gly Ser Ala Asn Val Phe Val Tyr
                325                 330                 335

Val Cys Ile Pro Asp Asp Asn Asp Arg Asn Asp Asp His Cys Glu Lys
                340                 345                 350

Ala Gly Asp Phe Phe Val Leu Gly Gly Pro Ser Glu Met Lys Trp Gln
                355                 360                 365

Phe Tyr Arg Pro Tyr Leu Phe Asp Leu Ser Asp Thr Val His Lys Met
                370                 375                 380

Gly Met Lys Leu Asp Gly His Tyr Thr Val Lys Ala Glu Leu Phe Ser
385                 390                 395                 400

Val Asn Gly Thr Ala Leu Pro Asp Asp Leu Leu Pro His Pro Val Val
                405                 410                 415

Val His His Pro Glu Lys Gly Phe Thr Asp Pro Pro Val Lys His His
                420                 425                 430

Gln Ser Ala Asn Leu Leu Val Arg Lys Asn Ile Asn Asp Leu Thr Arg
                435                 440                 445

Glu Glu Val Leu Asn Leu Arg Glu Ala Phe His Lys Phe Gln Glu Asp
                450                 455                 460
```

```
Arg Ser Val Asp Gly Tyr Gln Ala Thr Ala Glu Tyr His Gly Leu Pro
465                 470                 475                 480

Ala Arg Cys Pro Arg Pro Asp Ala Lys Asp Arg Tyr Ala Cys Cys Val
                485                 490                 495

His Gly Met Pro Ile Phe Pro His Trp His Arg Leu Phe Val Thr Gln
                500                 505                 510

Val Glu Asp Ala Leu Val Gly Arg Gly Ala Thr Ile Gly Ile Pro Tyr
                515                 520                 525

Trp Asp Trp Thr Glu Pro Met Thr His Ile Pro Gly Leu Ala Gly Asn
530                 535                 540

Lys Thr Tyr Val Asp Ser His Gly Ala Ser His Thr Asn Pro Phe His
545                 550                 555                 560

Ser Ser Val Ile Ala Phe Glu Glu Asn Ala Pro His Thr Lys Arg Gln
                565                 570                 575

Ile Asp Gln Arg Leu Phe Lys Pro Ala Thr Phe Gly His His Thr Asp
                580                 585                 590

Leu Phe Asn Gln Ile Leu Tyr Ala Phe Glu Gln Glu Asp Tyr Cys Asp
            595                 600                 605

Phe Glu Val Gln Phe Glu Ile Thr His Asn Thr Ile His Ala Trp Thr
610                 615                 620

Gly Gly Ser Glu His Phe Ser Met Ser Ser Leu His Tyr Thr Ala Phe
625                 630                 635                 640

Asp Pro Leu Phe Tyr Phe His His Ser Asn Val Asp Arg Leu Trp Ala
                645                 650                 655

Val Trp Gln Ala Leu Gln Met Arg Arg His Lys Pro Tyr Arg Ala His
                660                 665                 670

Cys Ala Ile Ser Leu Glu His Met His Leu Lys Pro Phe Ala Phe Ser
                675                 680                 685

Ser Pro Leu Asn Asn Asn Glu Lys Thr His Ala Asn Ala Met Pro Asn
            690                 695                 700

Lys Ile Tyr Asp Tyr Glu Asn Val Leu His Tyr Thr Tyr Glu Asp Leu
705                 710                 715                 720

Thr Phe Gly Gly Ile Ser Leu Glu Asn Ile Glu Lys Met Ile His Glu
                725                 730                 735

Asn Gln Gln Glu Asp Arg Ile Tyr Ala Gly Phe Leu Leu Ala Gly Ile
                740                 745                 750

Arg Thr Ser Ala Asn Val Asp Ile Phe Ile Lys Thr Thr Asp Ser Val
            755                 760                 765

Gln His Lys Ala Gly Thr Phe Ala Val Leu Gly Gly Ser Lys Glu Met
            770                 775                 780

Lys Trp Gly Phe Asp Arg Val Phe Lys Phe Asp Ile Thr His Val Leu
785                 790                 795                 800

Lys Asp Leu Asp Leu Thr Ala Asp Gly Asp Phe Glu Val Thr Val Asp
                805                 810                 815

Ile Thr Glu Val Asp Gly Thr Lys Leu Ala Ser Ser Leu Ile Pro His
                820                 825                 830

Ala Ser Val Ile Arg Glu His Ala Arg Val Lys Phe Asp Lys Val Pro
                835                 840                 845

Arg Ser Arg Leu Ile Arg Lys Asn Val Asp Arg Leu Ser Pro Glu Glu
                850                 855                 860

Met Asn Glu Leu Arg Lys Ala Leu Ala Leu Leu Lys Glu Asp Lys Ser
865                 870                 875                 880

Ala Gly Gly Phe Gln Gln Leu Gly Ala Phe His Gly Glu Pro Lys Trp
```

-continued

```
                885                 890                 895
Cys Pro Ser Pro Glu Ala Ser Lys Lys Phe Ala Cys Cys Val His Gly
                900                 905                 910
Met Ser Val Phe Pro His Trp His Arg Leu Leu Thr Val Gln Ser Glu
                915                 920                 925
Asn Ala Leu Arg Arg His Gly Tyr Asp Gly Ala Leu Pro Tyr Trp Asp
                930                 935                 940
Trp Thr Ser Pro Leu Asn His Leu Pro Glu Leu Ala Asp His Glu Lys
945                 950                 955                 960
Tyr Val Asp Pro Glu Asp Gly Val Glu Lys His Asn Pro Trp Phe Asp
                965                 970                 975
Gly His Ile Asp Thr Val Asp Lys Thr Thr Arg Ser Val Gln Asn
                980                 985                 990
Lys Leu Phe Glu Gln Pro Glu Phe Gly His Tyr Thr Ser Ile Ala Lys
                995                 1000                1005
Gln Val Leu Leu Ala Leu Glu Gln Asp Asn Phe Cys Asp Phe Glu
        1010                1015                1020
Ile Gln Tyr Glu Ile Ala His Asn Tyr Ile His Ala Leu Val Gly
        1025                1030                1035
Gly Ala Gln Pro Tyr Gly Met Ala Ser Leu Arg Tyr Thr Ala Phe
        1040                1045                1050
Asp Pro Leu Phe Tyr Leu His Ser Asn Thr Asp Arg Ile Trp
        1055                1060                1065
Ala Ile Trp Gln Ala Leu Gln Lys Tyr Arg Gly Lys Pro Tyr Asn
        1070                1075                1080
Val Ala Asn Cys Ala Val Thr Ser Met Arg Glu Pro Leu Gln Pro
        1085                1090                1095
Phe Gly Leu Ser Ala Asn Ile Asn Thr Asp His Val Thr Lys Glu
        1100                1105                1110
His Ser Val Pro Phe Asn Val Phe Asp Tyr Lys Thr Asn Phe Asn
        1115                1120                1125
Tyr Glu Tyr Asp Thr Leu Glu Phe Asn Gly Leu Ser Ile Ser Gln
        1130                1135                1140
Leu Asn Lys Lys Leu Glu Ala Ile Lys Ser Gln Asp Arg Phe Phe
        1145                1150                1155
Ala Gly Phe Leu Leu Ser Gly Phe Lys Lys Ser Ser Leu Val Lys
        1160                1165                1170
Phe Asn Ile Cys Thr Asp Ser Ser Asn Cys His Pro Ala Gly Glu
        1175                1180                1185
Phe Tyr Leu Leu Gly Asp Glu Asn Glu Met Pro Trp Ala Tyr Asp
        1190                1195                1200
Arg Val Phe Lys Tyr Asp Ile Thr Glu Lys Leu His Asp Leu Lys
        1205                1210                1215
Leu His Ala Glu Asp His Phe Tyr Ile Asp Tyr Glu Val Phe Asp
        1220                1225                1230
Leu Lys Pro Ala Ser Leu Gly Lys Asp Leu Phe Lys Gln Pro Ser
        1235                1240                1245
Val Ile His Glu Pro Arg Ile Gly His His Glu Gly Glu Val Tyr
        1250                1255                1260
Gln Ala Glu Val Thr Ser Ala Asn Arg Ile Arg Lys Asn Ile Glu
        1265                1270                1275
Asn Leu Ser Leu Gly Glu Leu Glu Ser Leu Arg Ala Ala Phe Leu
        1280                1285                1290
```

-continued

Glu Ile Glu Asn Asp Gly Thr Tyr Glu Ser Ile Ala Lys Phe His
    1295            1300            1305

Gly Ser Pro Gly Leu Cys Gln Leu Asn Gly Asn Pro Ile Ser Cys
    1310            1315            1320

Cys Val His Gly Met Pro Thr Phe Pro His Trp His Arg Leu Tyr
    1325            1330            1335

Val Val Val Val Glu Asn Ala Leu Leu Lys Lys Gly Ser Ser Val
    1340            1345            1350

Ala Val Pro Tyr Trp Asp Trp Thr Lys Arg Ile Glu His Leu Pro
    1355            1360            1365

His Leu Ile Ser Asp Ala Thr Tyr Tyr Asn Ser Arg Gln His His
    1370            1375            1380

Tyr Glu Thr Asn Pro Phe His His Gly Lys Ile Thr His Glu Asn
    1385            1390            1395

Glu Ile Thr Thr Arg Asp Pro Lys Asp Ser Leu Phe His Ser Asp
    1400            1405            1410

Tyr Phe Tyr Glu Gln Val Leu Tyr Ala Leu Glu Gln Asp Asn Phe
    1415            1420            1425

Cys Asp Phe Glu Ile Gln Leu Glu Ile Leu His Asn Ala Leu His
    1430            1435            1440

Ser Leu Leu Gly Gly Lys Gly Lys Tyr Ser Met Ser Asn Leu Asp
    1445            1450            1455

Tyr Ala Ala Phe Asp Pro Val Phe Phe Leu His His Ala Thr Thr
    1460            1465            1470

Asp Arg Ile Trp Ala Ile Trp Gln Asp Leu Gln Arg Phe Arg Lys
    1475            1480            1485

Arg Pro Tyr Arg Glu Ala Asn Cys Ala Ile Gln Leu Met His Thr
    1490            1495            1500

Pro Leu Gln Pro Phe Asp Lys Ser Asp Asn Asn Asp Glu Ala Thr
    1505            1510            1515

Lys Thr His Ala Thr Pro His Asp Gly Phe Glu Tyr Gln Asn Ser
    1520            1525            1530

Phe Gly Tyr Ala Tyr Asp Asn Leu Glu Leu Asn His Tyr Ser Ile
    1535            1540            1545

Pro Gln Leu Asp His Met Leu Gln Glu Arg Lys Arg His Asp Arg
    1550            1555            1560

Val Phe Ala Gly Phe Leu Leu His Asn Ile Gly Thr Ser Ala Asp
    1565            1570            1575

Gly His Val Phe Val Cys Leu Pro Thr Gly Glu His Thr Lys Asp
    1580            1585            1590

Cys Ser His Glu Ala Gly Met Phe Ser Ile Leu Gly Gly Gln Thr
    1595            1600            1605

Glu Met Ser Phe Val Phe Asp Arg Leu Tyr Lys Leu Asp Ile Thr
    1610            1615            1620

Lys Ala Leu Lys Lys Asn Gly Val His Leu Gln Gly Asp Phe Asp
    1625            1630            1635

Leu Glu Ile Glu Ile Thr Ala Val Asn Gly Ser His Leu Asp Ser
    1640            1645            1650

His Val Ile His Ser Pro Thr Ile Leu Phe Glu Ala Gly Thr Asp
    1655            1660            1665

Ser Ala His Thr Asp Asp Gly His Thr Glu Pro Val Met Ile Arg
    1670            1675            1680

-continued

Lys Asp Ile Thr Gln Leu Asp Lys Arg Gln Gln Leu Ser Leu Val
1685                1690                1695

Lys Ala Leu Glu Ser Met Lys Ala Asp His Ser Ser Asp Gly Phe
1700                1705                1710

Gln Ala Ile Ala Ser Phe His Ala Leu Pro Pro Leu Cys Pro Ser
1715                1720                1725

Pro Ala Ala Ser Lys Arg Phe Ala Cys Cys Val His Gly Met Ala
1730                1735                1740

Thr Phe Pro Gln Trp His Arg Leu Tyr Thr Val Gln Phe Gln Asp
1745                1750                1755

Ser Leu Arg Lys His Gly Ala Val Val Gly Leu Pro Tyr Trp Asp
1760                1765                1770

Trp Thr Leu Pro Arg Ser Glu Leu Pro Glu Leu Leu Thr Val Ser
1775                1780                1785

Thr Ile His Asp Pro Glu Thr Gly Arg Asp Ile Pro Asn Pro Phe
1790                1795                1800

Ile Gly Ser Lys Ile Glu Phe Glu Gly Glu Asn Val His Thr Lys
1805                1810                1815

Arg Asp Ile Asn Arg Asp Arg Leu Phe Gln Gly Ser Thr Lys Thr
1820                1825                1830

His His Asn Trp Phe Ile Glu Gln Ala Leu Leu Ala Leu Glu Gln
1835                1840                1845

Thr Asn Tyr Cys Asp Phe Glu Val Gln Phe Glu Ile Met His Asn
1850                1855                1860

Gly Val His Thr Trp Val Gly Gly Lys Glu Pro Tyr Gly Ile Gly
1865                1870                1875

His Leu His Tyr Ala Ser Tyr Asp Pro Leu Phe Tyr Ile His His
1880                1885                1890

Ser Gln Thr Asp Arg Ile Trp Ala Ile Trp Gln Ser Leu Gln Arg
1895                1900                1905

Phe Arg Gly Leu Ser Gly Ser Glu Ala Asn Cys Ala Val Asn Leu
1910                1915                1920

Met Lys Thr Pro Leu Lys Pro Phe Ser Phe Gly Ala Pro Tyr Asn
1925                1930                1935

Leu Asn Asp His Thr His Asp Phe Ser Lys Pro Glu Asp Thr Phe
1940                1945                1950

Asp Tyr Gln Lys Phe Gly Tyr Ile Tyr Asp Thr Leu Glu Phe Ala
1955                1960                1965

Gly Trp Ser Ile Arg Gly Ile Asp His Ile Val Arg Asn Arg Gln
1970                1975                1980

Glu His Ser Arg Val Phe Ala Gly Phe Leu Leu Glu Gly Phe Gly
1985                1990                1995

Thr Ser Ala Thr Val Asp Phe Gln Val Cys Arg Thr Ala Gly Asp
2000                2005                2010

Cys Glu Asp Ala Gly Tyr Phe Thr Val Leu Gly Gly Glu Lys Glu
2015                2020                2025

Met Pro Trp Ala Phe Asp Arg Leu Tyr Lys Tyr Asp Ile Thr Glu
2030                2035                2040

Thr Leu Asp Lys Met Asn Leu Arg His Asp Glu Ile Phe Gln Ile
2045                2050                2055

Glu Val Thr Ile Thr Ser Tyr Asp Gly Thr Val Leu Asp Ser Gly
2060                2065                2070

Leu Ile Pro Thr Pro Ser Ile Ile Tyr Asp Pro Ala His His Asp

-continued

```
                2075                2080                2085
Ile Ser Ser His His Leu Ser Leu Asn Lys Val Arg His Asp Leu
        2090                2095                2100
Ser Thr Leu Ser Glu Arg Asp Ile Gly Ser Leu Lys Tyr Ala Leu
        2105                2110                2115
Ser Ser Leu Gln Ala Asp Thr Ser Ala Asp Gly Phe Ala Ala Ile
        2120                2125                2130
Ala Ser Phe His Gly Leu Pro Ala Lys Cys Asn Asp Ser His Asn
        2135                2140                2145
Asn Glu Val Ala Cys Cys Ile His Gly Met Pro Thr Phe Pro His
        2150                2155                2160
Trp His Arg Leu Tyr Thr Leu Gln Phe Glu Gln Ala Leu Arg Arg
        2165                2170                2175
His Gly Ser Ser Val Ala Val Pro Tyr Trp Asp Trp Thr Lys Pro
        2180                2185                2190
Ile His Asn Ile Pro His Leu Phe Thr Asp Lys Glu Tyr Tyr Asp
        2195                2200                2205
Val Trp Arg Asn Lys Val Met Pro Asn Pro Phe Ala Arg Gly Tyr
        2210                2215                2220
Val Pro Ser His Asp Thr Tyr Thr Val Arg Asp Val Gln Glu Gly
        2225                2230                2235
Leu Phe His Leu Thr Ser Thr Gly Glu His Ser Ala Leu Leu Asn
        2240                2245                2250
Gln Ala Leu Leu Ala Leu Glu Gln His Asp Tyr Cys Asp Phe Ala
        2255                2260                2265
Val Gln Phe Glu Val Met His Asn Thr Ile His Tyr Leu Val Gly
        2270                2275                2280
Gly Pro Gln Val Tyr Ser Leu Ser Ser Leu His Tyr Ala Ser Tyr
        2285                2290                2295
Asp Pro Ile Phe Phe Ile His His Ser Phe Val Asp Lys Val Trp
        2300                2305                2310
Ala Val Trp Gln Ala Leu Gln Glu Lys Arg Gly Leu Pro Ser Asp
        2315                2320                2325
Arg Ala Asp Cys Ala Val Ser Leu Met Thr Gln Asn Met Arg Pro
        2330                2335                2340
Phe His Tyr Glu Ile Asn His Asn Gln Phe Thr Lys Lys His Ala
        2345                2350                2355
Val Pro Asn Asp Val Phe Lys Tyr Glu Leu Leu Gly Tyr Arg Tyr
        2360                2365                2370
Asp Asn Leu Glu Ile Gly Gly Met Asn Leu His Glu Ile Glu Lys
        2375                2380                2385
Glu Ile Lys Asp Lys Gln His His Val Arg Val Phe Ala Gly Phe
        2390                2395                2400
Leu Leu His Gly Ile Arg Thr Ser Ala Asp Val Gln Phe Gln Ile
        2405                2410                2415
Cys Lys Thr Ser Glu Asp Cys His His Gly Gly Gln Ile Phe Val
        2420                2425                2430
Leu Gly Gly Thr Lys Glu Met Ala Trp Ala Tyr Asn Arg Leu Phe
        2435                2440                2445
Lys Tyr Asp Ile Thr His Ala Leu His Asp Ala His Ile Thr Pro
        2450                2455                2460
Glu Asp Val Phe His Pro Ser Glu Pro Phe Phe Ile Lys Val Ser
        2465                2470                2475
```

-continued

Val Thr Ala Val Asn Gly Thr Val Leu Pro Ala Ser Ile Leu His
            2480            2485            2490

Ala Pro Thr Ile Ile Tyr Glu Pro Gly Leu Asp His His Glu Asp
    2495            2500            2505

His His Ser Ser Ser Met Ala Gly His Gly Val Arg Lys Glu Ile
    2510            2515            2520

Asn Thr Leu Thr Thr Ala Glu Val Asp Asn Leu Lys Asp Ala Met
    2525            2530            2535

Arg Ala Val Met Ala Asp His Gly Pro Asn Gly Tyr Gln Ala Ile
    2540            2545            2550

Ala Ala Phe His Gly Asn Pro Pro Met Cys Pro Met Pro Asp Gly
    2555            2560            2565

Lys Asn Tyr Ser Cys Cys Thr His Gly Met Ala Thr Phe Pro His
    2570            2575            2580

Trp His Arg Leu Tyr Thr Lys Gln Met Glu Asp Ala Leu Thr Ala
    2585            2590            2595

His Gly Ala Arg Val Gly Leu Pro Tyr Trp Asp Gly Thr Thr Ala
    2600            2605            2610

Phe Thr Ala Leu Pro Thr Phe Val Thr Asp Glu Glu Asp Asn Pro
    2615            2620            2625

Phe His His Gly His Ile Asp Tyr Leu Gly Val Asp Thr Thr Arg
    2630            2635            2640

Ser Pro Arg Asp Lys Leu Phe Asn Asp Pro Glu Arg Gly Ser Glu
    2645            2650            2655

Ser Phe Phe Tyr Arg Gln Val Leu Leu Ala Leu Glu Gln Thr Asp
    2660            2665            2670

Phe Cys Gln Phe Glu Val Gln Phe Glu Ile Thr His Asn Ala Ile
    2675            2680            2685

His Ser Trp Thr Gly Gly Leu Thr Pro Tyr Gly Met Ser Thr Leu
    2690            2695            2700

Glu Tyr Thr Thr Tyr Asp Pro Leu Phe Trp Leu His His Ala Asn
    2705            2710            2715

Thr Asp Arg Ile Trp Ala Ile Trp Gln Ala Leu Gln Glu Tyr Arg
    2720            2725            2730

Gly Leu Pro Tyr Asp His Ala Asn Cys Glu Ile Gln Ala Met Lys
    2735            2740            2745

Arg Pro Leu Arg Pro Phe Ser Asp Pro Ile Asn His Asn Ala Phe
    2750            2755            2760

Thr His Ser Asn Ala Lys Pro Thr Asp Val Phe Glu Tyr Ser Arg
    2765            2770            2775

Phe Asn Phe Gln Tyr Asp Asn Leu Arg Phe His Gly Met Thr Ile
    2780            2785            2790

Lys Lys Leu Glu His Glu Leu Glu Lys Gln Lys Glu Glu Asp Arg
    2795            2800            2805

Thr Phe Ala Ala Phe Leu Leu His Gly Ile Lys Lys Ser Ala Asp
    2810            2815            2820

Val Ser Phe Asp Val Cys Asn His Asp Gly Glu Cys His Phe Ala
    2825            2830            2835

Gly Thr Phe Ala Ile Leu Gly Gly Glu His Glu Met Pro Trp Ser
    2840            2845            2850

Phe Asp Arg Leu Phe Arg Tyr Asp Ile Thr Gln Val Leu Lys Gln
    2855            2860            2865

```
Met His Leu Glu Tyr Asp Ser Asp Phe Thr Phe His Met Arg Ile
    2870                2875                2880

Ile Asp Thr Ser Gly Lys Gln Leu Pro Ser Asp Leu Ile Lys Met
    2885                2890                2895

Pro Thr Val Glu His Ser Pro Gly Gly Lys His Glu Lys His
    2900                2905                2910

His Glu Asp His His Glu Asp Ile Leu Val Arg Lys Asn Ile His
    2915                2920                2925

Ser Leu Ser His His Glu Ala Glu Glu Leu Arg Asp Ala Leu Tyr
    2930                2935                2940

Lys Leu Gln Asn Asp Glu Ser His Gly Gly Tyr Glu His Ile Ala
    2945                2950                2955

Gly Phe His Gly Tyr Pro Asn Leu Cys Pro Glu Lys Gly Asp Glu
    2960                2965                2970

Lys Tyr Pro Cys Cys Val His Gly Met Ser Ile Phe Pro His Trp
    2975                2980                2985

His Arg Leu His Thr Ile Gln Phe Glu Arg Ala Leu Lys Lys His
    2990                2995                3000

Gly Ser His Leu Gly Ile Pro Tyr Trp Asp Trp Thr Gln Thr Ile
    3005                3010                3015

Ser Ser Leu Pro Thr Phe Phe Ala Asp Ser Gly Asn Asn Asn Pro
    3020                3025                3030

Phe Phe Lys Tyr His Ile Arg Ser Ile Asn Gln Asp Thr Val Arg
    3035                3040                3045

Asp Val Asn Glu Ala Ile Phe Gln Gln Thr Lys Phe Gly Glu Phe
    3050                3055                3060

Ser Ser Ile Phe Tyr Leu Ala Leu Gln Ala Leu Glu Glu Asp Asn
    3065                3070                3075

Tyr Cys Asp Phe Glu Val Gln Tyr Glu Ile Leu His Asn Glu Val
    3080                3085                3090

His Ala Leu Ile Gly Gly Ala Glu Lys Tyr Ser Met Ser Thr Leu
    3095                3100                3105

Glu Tyr Ser Ala Phe Asp Pro Tyr Phe Met Ile His His Ala Ser
    3110                3115                3120

Leu Asp
    3125

<210> SEQ ID NO 2
<211> LENGTH: 37
<212> TYPE: PRT
<213> ORGANISM: Artificial Sequence
<220> FEATURE:
<223> OTHER INFORMATION: Amylin Peptide

<400> SEQUENCE: 2

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 3
<211> LENGTH: 16
<212> TYPE: PRT
<213> ORGANISM: Artificial Sequence
<220> FEATURE:
```

```
<223> OTHER INFORMATION: Amylin C

<400> SEQUENCE: 3

Cys Asn Asn Phe Gly Ala Ile Leu Ser Ser Thr Asn Val Gly Ser Asn
1               5                   10                  15

<210> SEQ ID NO 4
<211> LENGTH: 21
<212> TYPE: PRT
<213> ORGANISM: Artificial Sequence
<220> FEATURE:
<223> OTHER INFORMATION: Amylin N

<400> SEQUENCE: 4

Cys Lys Cys Asn Thr Ala Thr Cys Ala Thr Gln Arg Leu Ala Asn Phe
1               5                   10                  15

Leu Val His Ser Ser
            20

<210> SEQ ID NO 5
<211> LENGTH: 42
<212> TYPE: PRT
<213> ORGANISM: Artificial Sequence
<220> FEATURE:
<223> OTHER INFORMATION: Amyloid beta

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 6
<211> LENGTH: 16
<212> TYPE: PRT
<213> ORGANISM: Artificial Sequence
<220> FEATURE:
<223> OTHER INFORMATION: Abeta N

<400> SEQUENCE: 6

Cys Asp Ala Glu Phe Arg His Asp Ser Gly Tyr Glu Val His His Gln
1               5                   10                  15

<210> SEQ ID NO 7
<211> LENGTH: 28
<212> TYPE: PRT
<213> ORGANISM: Artificial Sequence
<220> FEATURE:
<223> OTHER INFORMATION: Abeta C

<400> SEQUENCE: 7

Cys Lys Leu Val Phe Phe Ala Glu Asp Val Gly Ser Asn Lys Gly Ala
1               5                   10                  15

Ile Ile Gly Leu Met Val Gly Gly Val Val Ile Ala
            20                  25
```